(12) United States Patent
Karmarkar

(10) Patent No.: US 10,888,374 B2
(45) Date of Patent: Jan. 12, 2021

(54) TISSUE ABLATION AND ASSESSMENT SYSTEM AND METHOD OF USE THEREOF

(71) Applicant: The Johns Hopkins University, Baltimore, MD (US)

(72) Inventor: Parag Karmarkar, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 321 days.

(21) Appl. No.: 15/742,470

(22) PCT Filed: Jul. 8, 2016

(86) PCT No.: PCT/US2016/041522
§ 371 (c)(1),
(2) Date: Jan. 5, 2018

(87) PCT Pub. No.: WO2017/008020
PCT Pub. Date: Jan. 12, 2017

(65) Prior Publication Data
US 2018/0214204 A1    Aug. 2, 2018

Related U.S. Application Data

(60) Provisional application No. 62/341,071, filed on May 25, 2016, provisional application No. 62/301,453, (Continued)

(51) Int. Cl.
*A61B 18/18* (2006.01)
*A61B 5/05* (2006.01)
(Continued)

(52) U.S. Cl.
CPC ........ *A61B 18/1815* (2013.01); *A61B 5/0093* (2013.01); *A61B 5/05* (2013.01);
(Continued)

(58) Field of Classification Search
CPC ............ A61B 18/1492; A61B 18/1815; A61B 2018/00023; A61B 2018/00029;
(Continued)

(56) References Cited

U.S. PATENT DOCUMENTS

| | | | | |
|---|---|---|---|---|
| 6,190,382 B1 * | 2/2001 | Ormsby | ............. | A61B 18/1492 606/33 |
| 7,070,595 B2 * | 7/2006 | Ormsby | ............. | A61B 18/1492 606/33 |

(Continued)

FOREIGN PATENT DOCUMENTS

EP    2 168 519 A2    3/2010

OTHER PUBLICATIONS

Neuzil et al. "Electrical Reconnection after pulmonary vein isolation is contingent on contact force during initial treatment." Circ Arrhythm Electrophysiol. 2013;6:327-333.
(Continued)

*Primary Examiner* — Michael F Peffley
(74) *Attorney, Agent, or Firm* — DLA Piper LLP (US)

(57) ABSTRACT

The present disclosure provides a system with an innovative electrode designed as an RF/microwave antenna as well as methods to monitor/assess biological tissue and perform surgical procedures.

18 Claims, 69 Drawing Sheets

Related U.S. Application Data filed on Feb. 29, 2016, provisional application No. 62/189,793, filed on Jul. 8, 2015.

(51) Int. Cl.
| | |
|---|---|
| *A61B 5/053* | (2006.01) |
| *A61B 18/14* | (2006.01) |
| *A61B 5/00* | (2006.01) |
| *A61B 17/00* | (2006.01) |
| *A61B 18/00* | (2006.01) |
| *A61B 90/00* | (2016.01) |

(52) U.S. Cl.
CPC .......... *A61B 5/0507* (2013.01); *A61B 5/0538* (2013.01); *A61B 18/1492* (2013.01); *A61B 2017/00026* (2013.01); *A61B 2017/00039* (2013.01); *A61B 2017/00084* (2013.01); *A61B 2017/00106* (2013.01); *A61B 2018/00023* (2013.01); *A61B 2018/00029* (2013.01); *A61B 2018/00351* (2013.01); *A61B 2018/00577* (2013.01); *A61B 2018/00636* (2013.01); *A61B 2018/00702* (2013.01); *A61B 2018/00773* (2013.01); *A61B 2018/00785* (2013.01); *A61B 2018/00791* (2013.01); *A61B 2018/00827* (2013.01); *A61B 2018/00875* (2013.01); *A61B 2018/1435* (2013.01); *A61B 2018/183* (2013.01); *A61B 2018/1823* (2013.01); *A61B 2018/1838* (2013.01); *A61B 2018/1846* (2013.01); *A61B 2018/1853* (2013.01); *A61B 2018/1861* (2013.01); *A61B 2018/1892* (2013.01); *A61B 2090/065* (2016.02); *A61B 2218/002* (2013.01); *A61B 2576/023* (2013.01)

(58) Field of Classification Search
CPC ........... A61B 2018/00351; A61B 2018/00577; A61B 2018/00636; A61B 2018/00702; A61B 2018/00773; A61B 2018/00785; A61B 2018/1435; A61B 2018/1823; A61B 2018/183; A61B 2018/1861; A61B 2018/1876; A61B 2018/1892; A61B 5/0093; A61B 5/05; A61B 5/0507; A61B 5/0538

See application file for complete search history.

(56) References Cited

U.S. PATENT DOCUMENTS

| | | | |
|---|---|---|---|
| 7,311,702 B2 * | 12/2007 | Tallarida | A61B 18/1492 600/373 |
| 7,699,841 B2 * | 4/2010 | Carr | A61B 18/18 606/33 |
| 7,998,139 B2 * | 8/2011 | Rossetto | A61B 18/18 606/33 |
| 8,099,151 B2 | 1/2012 | Halperin et al. | |
| 8,242,782 B2 * | 8/2012 | Brannan | A61B 18/18 324/415 |
| 8,246,615 B2 * | 8/2012 | Behnke | A61B 18/1815 606/33 |
| 8,721,559 B2 | 5/2014 | Peterson et al. | |
| 9,526,438 B2 | 12/2016 | Iskander et al. | |
| 2002/0091427 A1 | 7/2002 | Rappaport et al. | |
| 2004/0106971 A1 | 6/2004 | Ormsby et al. | |
| 2010/0087808 A1 * | 4/2010 | Paulus | A61B 18/1815 606/33 |
| 2014/0323823 A1 | 10/2014 | Iskander et al. | |

OTHER PUBLICATIONS

Reddy et al., "The relationship between contact force and clinical outcome during radiofrequency catheter ablation of atrial fibrillation in the TOCCATA study". Heart Rhythm 2012;9:1789-1795.

Extended European Search Report dated Mar. 20, 2019, regarding EP 16 82 2043.2.

Extended European Search Report dated Nov. 24, 2020, regarding EP 20 17 3496.9.

* cited by examiner

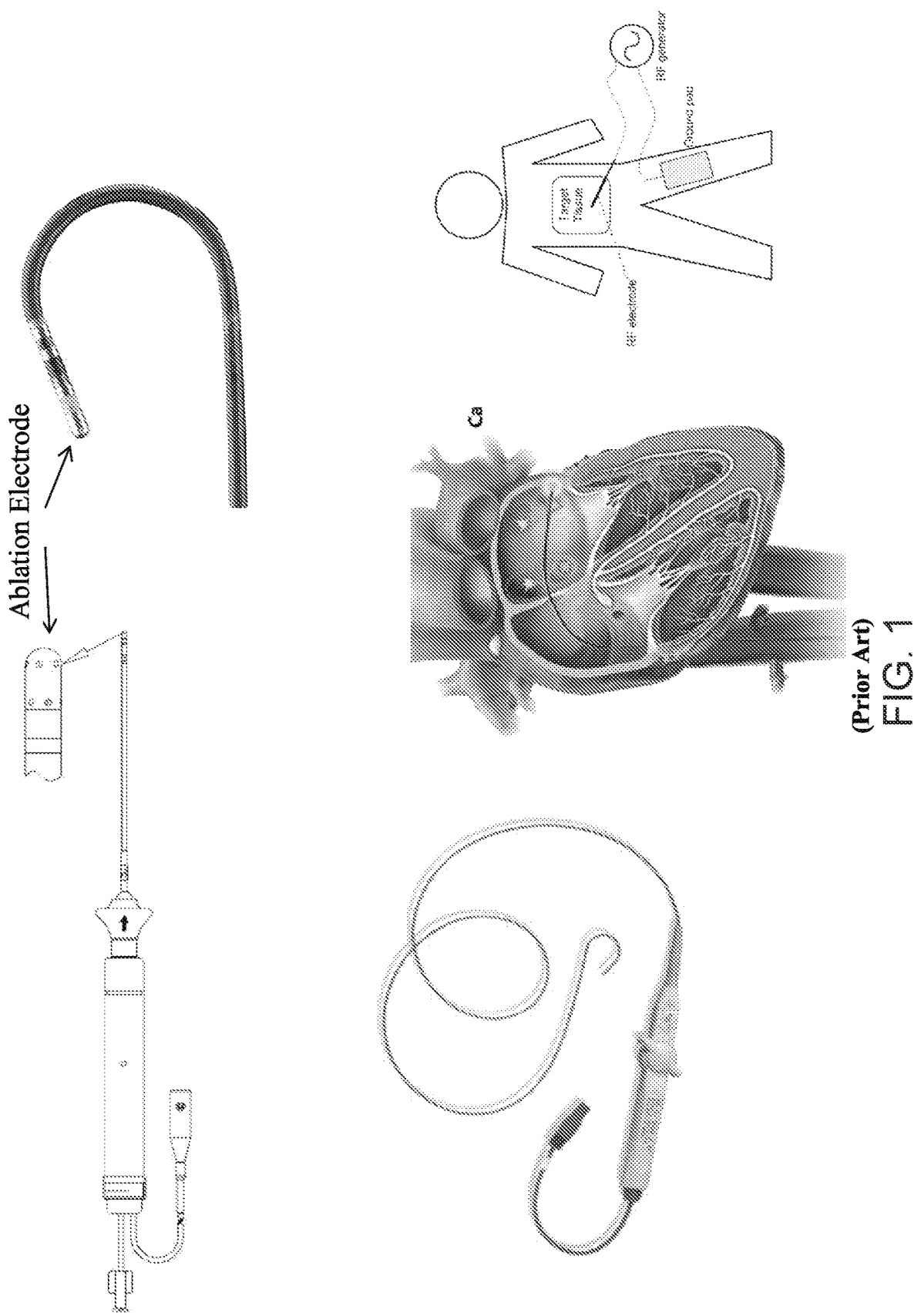

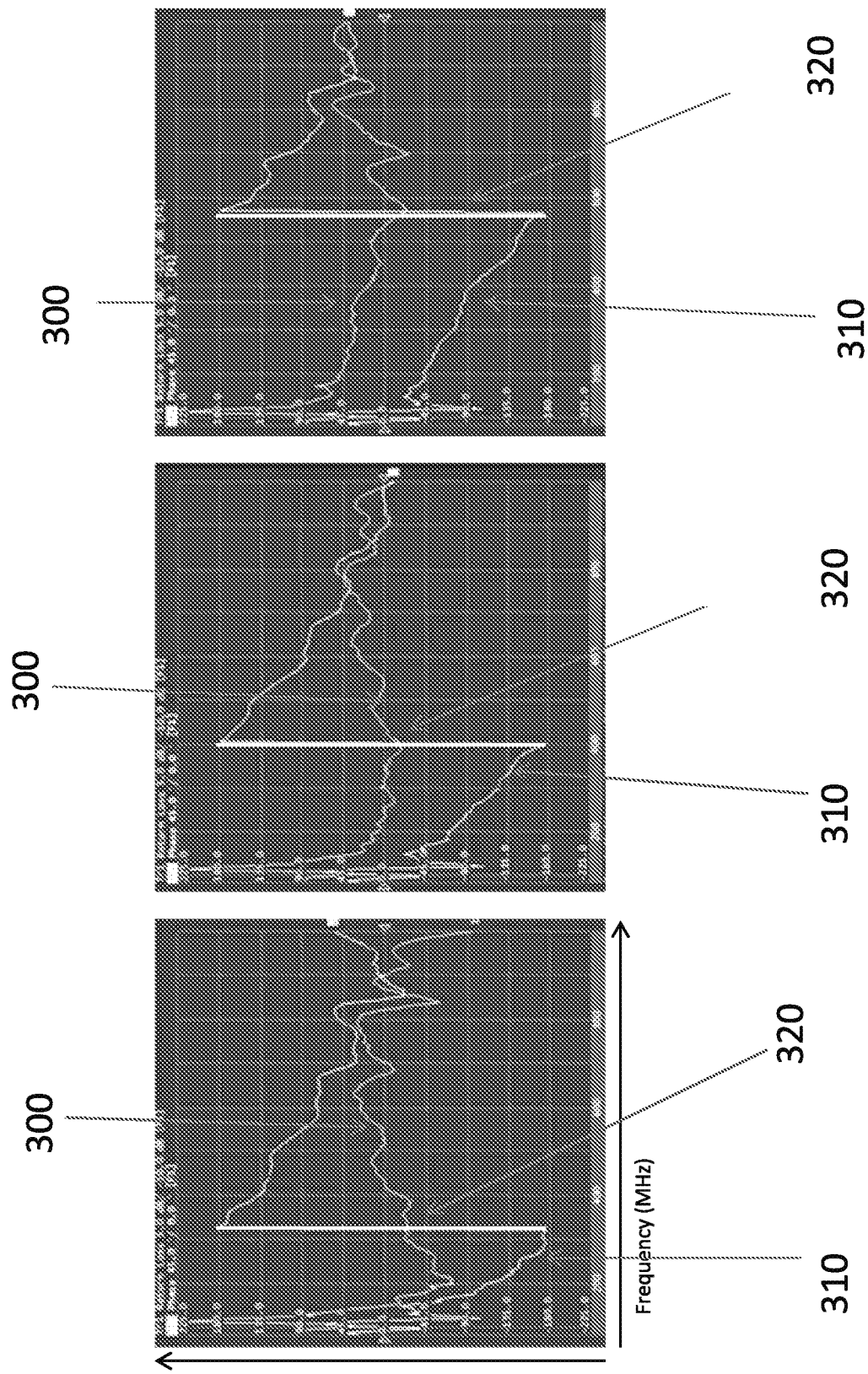

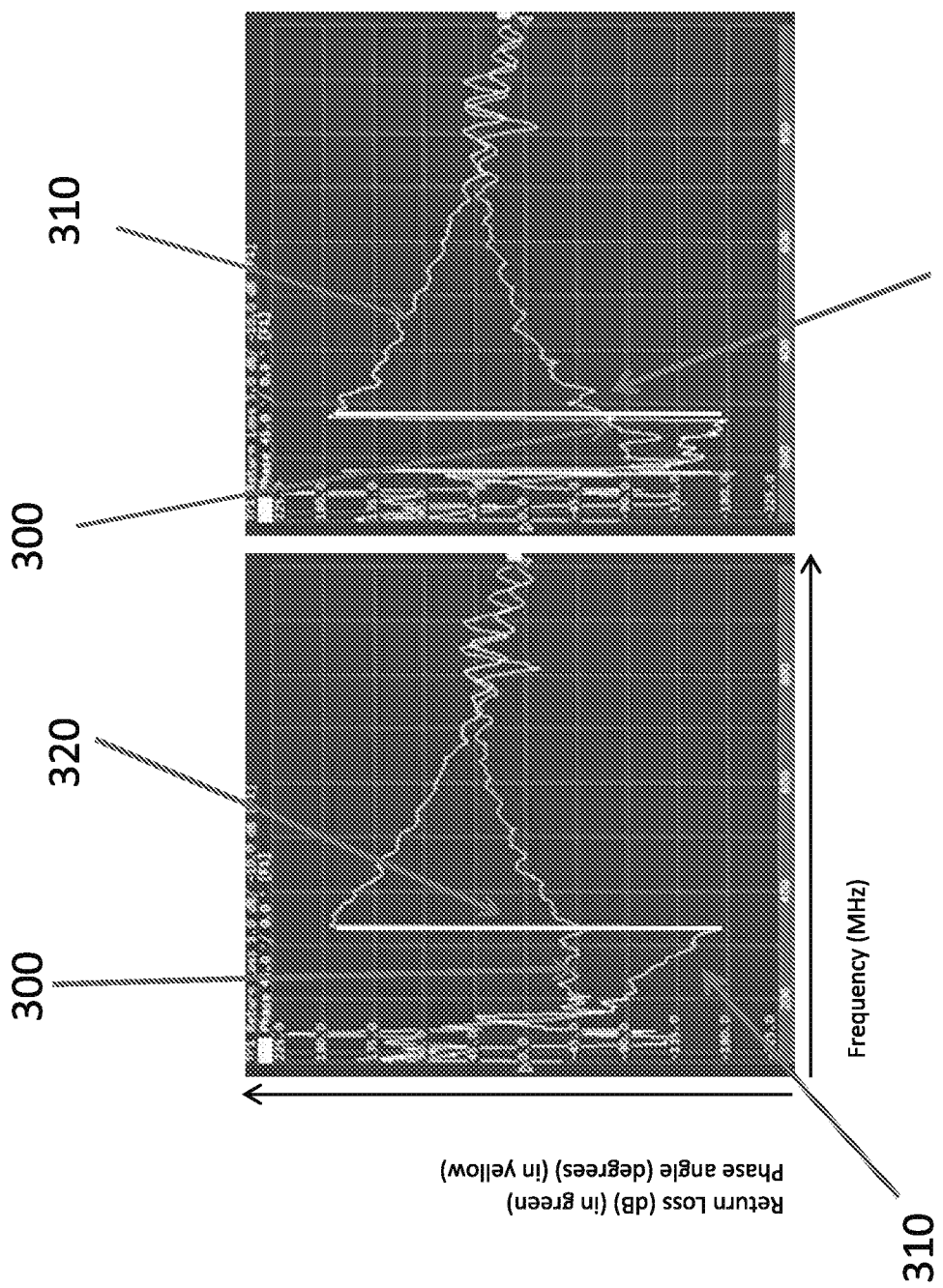

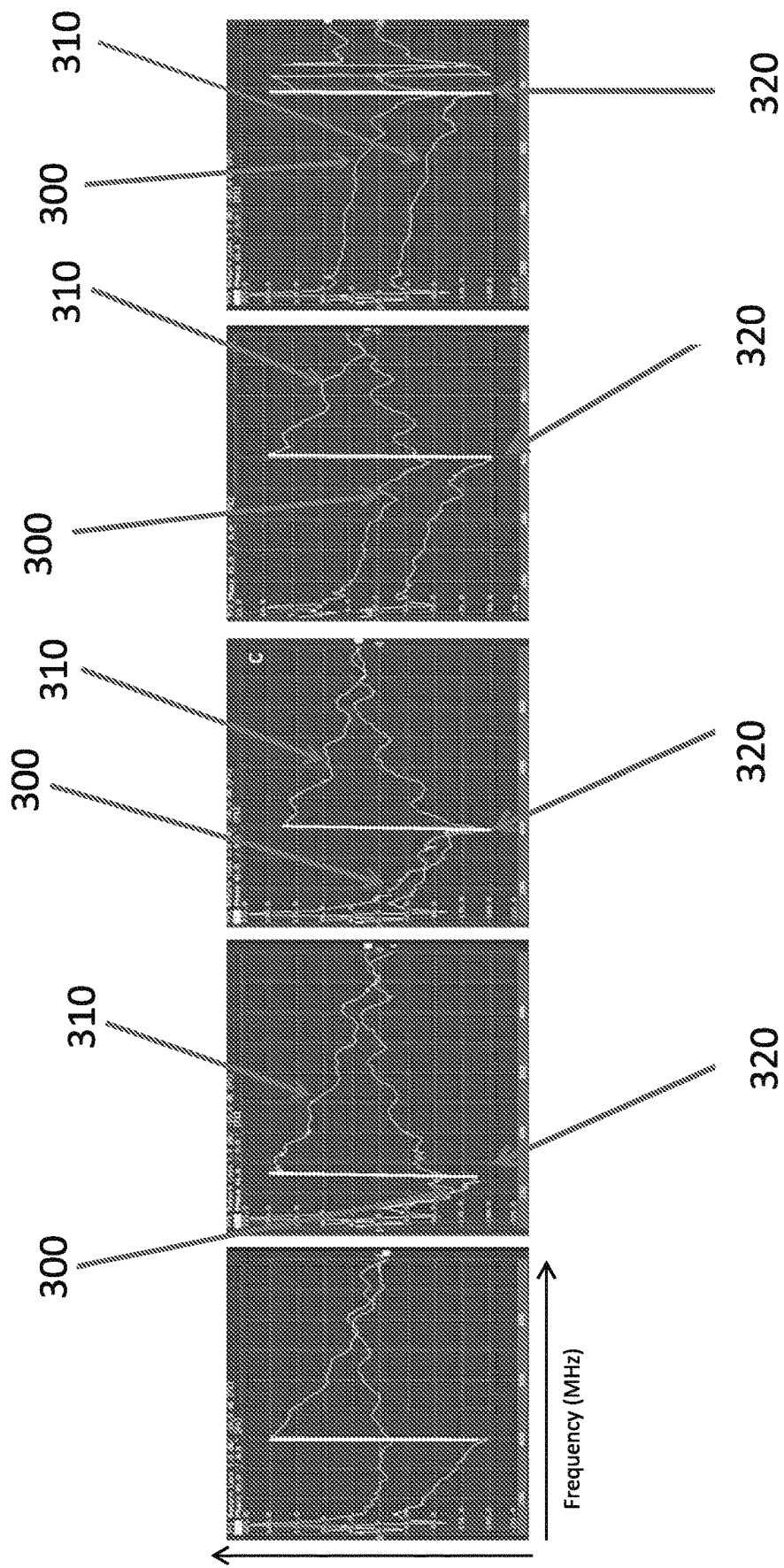

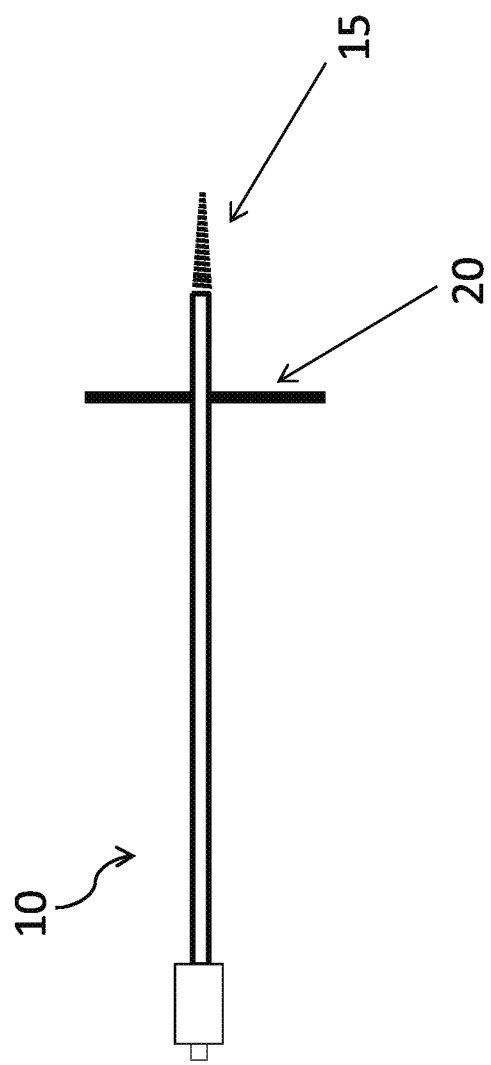

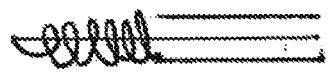
FIG. 22E
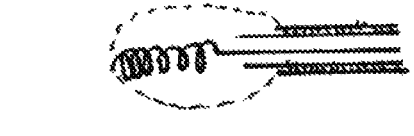
FIG. 22C
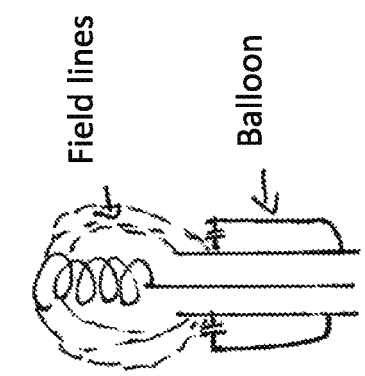
FIG. 22F
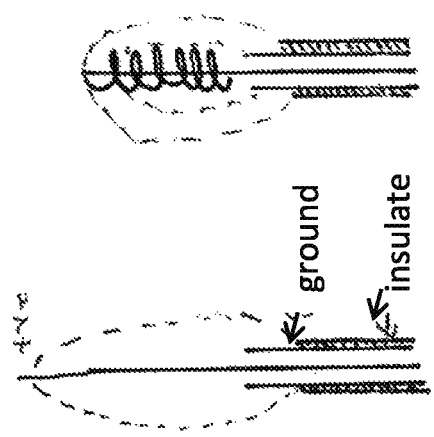
FIG. 22B
FIG. 22A
FIG. 22D

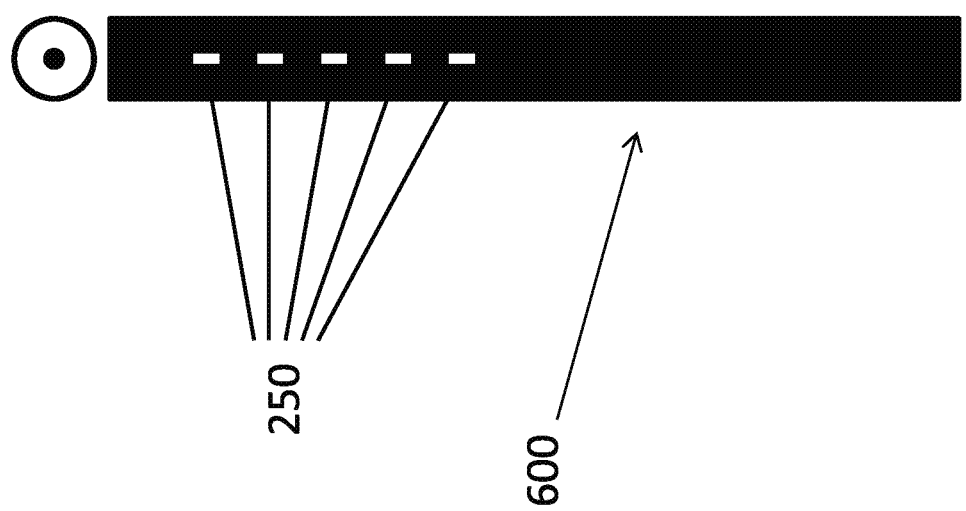

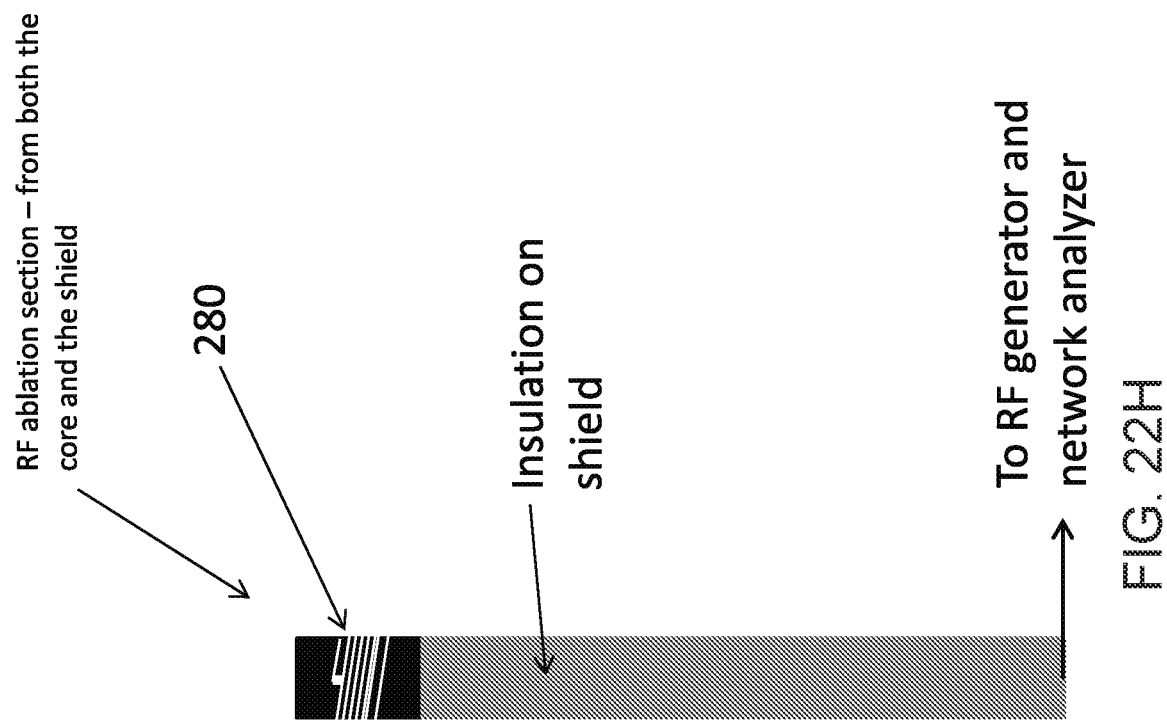

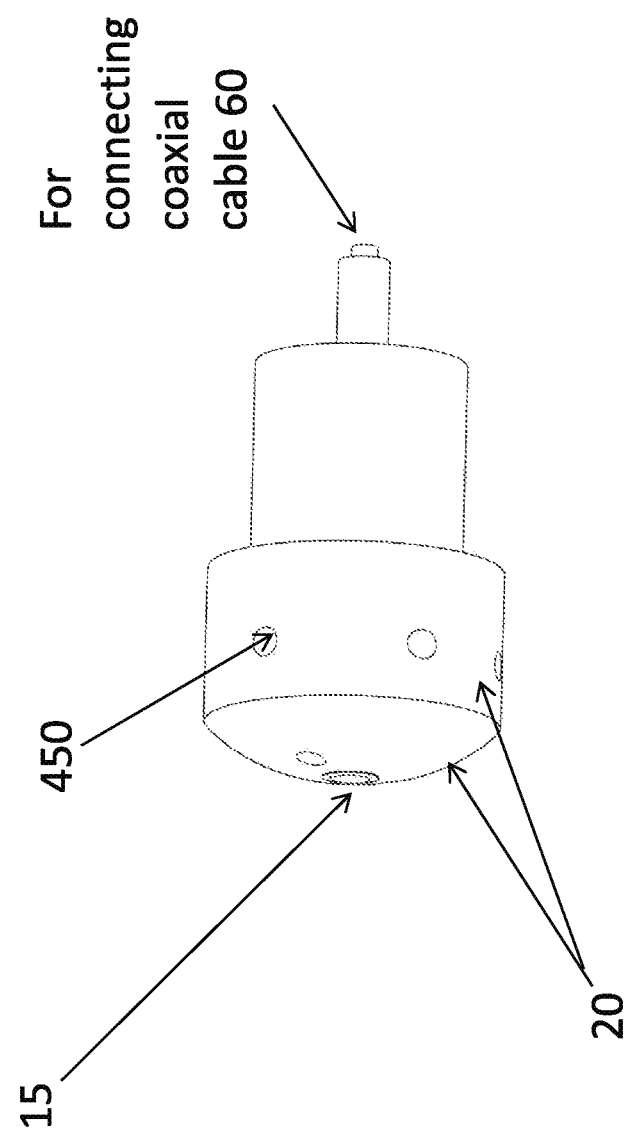

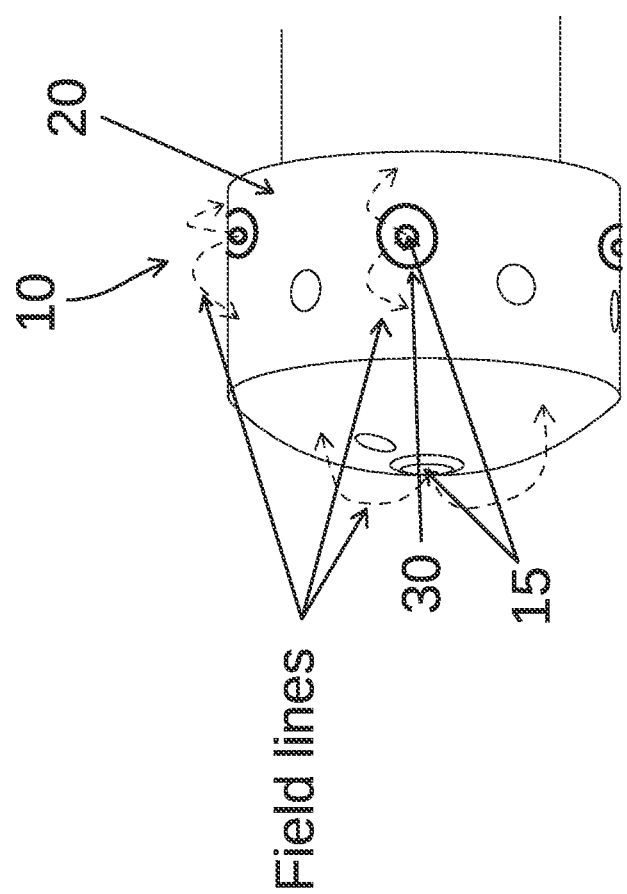

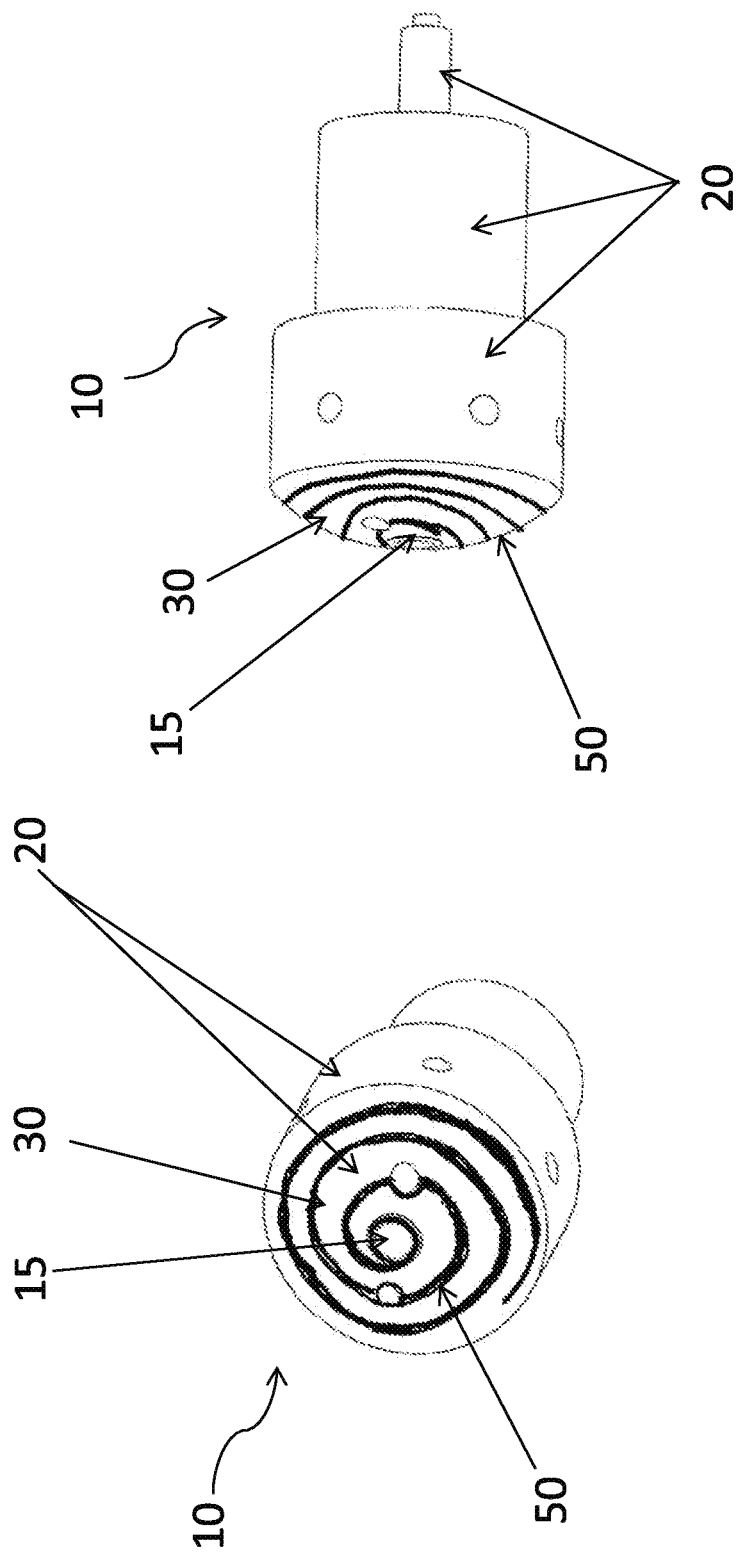

TISSUE ABLATION AND ASSESSMENT SYSTEM AND METHOD OF USE THEREOF

CROSS-REFERENCE TO RELATED APPLICATIONS

This application is a 35 USC § 371 National Stage application of International Application No. PCT/US2016/041522 filed Jul. 8, 2016, which claims the benefit under 35 USC § 119(e) to U.S. Application Ser. No. 62/341,071 filed May 25, 2016, U.S. Application Ser. No. 62/301,453 filed Feb. 29, 2016 and U.S. Application Ser. No. 62/189,793 filed Jul. 8, 2015. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under EB007829 awarded by the National Institutes of Health. The government has certain rights in the invention.

BACKGROUND OF THE DISCLOSURE

Field of the Invention

The invention relates generally to medical devices and more specifically to a system for tissue ablation and methods of use thereof.

Background Information

The electrical characteristics of an RF/microwave antenna in the frequency domain e.g. reflection coefficient v/s frequency, are a function of the antenna design, electrical properties (e.g. conductivity, relative permittivity, and the like) and the temperature of the medium surrounding the antenna. During RF ablation procedures, the tissue properties including conductivity, permittivity, and tissue temperature change significantly. These changes in the tissue can be monitored by detecting the changes in frequency domain electrical properties of antennas placed in direct contact with the tissue being ablated, and used to quantify extent of ablation and progression of lesion formation.

The characteristic electrical properties of an RF/microwave antenna in the frequency domain (e.g. reflection coefficient or return loss v/s frequency), as measured by a vector impedance network analyzer during a reflection/S11 measurement, are a function of the antenna design, electrical properties of the medium (e.g. conductivity, permittivity, and the like) and temperature of the medium surrounding the antenna. For a given antenna, the characteristic reflection electrical properties of the antenna, i.e. magnitude of impedance, return loss, reflection coefficient, phase angle, resonant frequency, and the like, will change in the frequency domain depending on the physical properties of tissue/medium surrounding the antenna. Thus monitoring the change in characteristic reflection electrical properties of an antenna in the frequency domain, the properties of the tissue/medium surrounding the antenna can be inferred via a S11 measurement on a frequency sweep vector network analyzer.

Similarly, transmission of electromagnetic waves between two antennas or coupling of two antennas through a medium is a function of antenna designs and electrical properties and temperature of the medium between the two antennas. Monitoring the change in transmission characteristic between two antennas, as measured during a S21/S12 measurement, can be used to infer the change in electrical properties of the tissue between the antennas.

The RF ablation processes changes the state of free or bound water in the tissue and denatures cell membrane proteins, this changes dielectric relaxation of proteins, cell membranes, and the like, resulting in a change in dielectric properties of the tissue. These changes between ablated and non-ablated tissue should provide sufficient dielectric contrast to distinguish extent of ablation by monitoring time domain reflection coefficient peaks of the electrode-antenna or monitoring the transmission/coupling characteristics of two antennae Since the measurements are carried out in a wide frequency range, and the tissue penetration depth are different at various frequencies; ablated tissue thickness will influence electrical properties of the antenna-electrode (staying with convention which used later).

During RF ablation (RFA) procedures e.g. cardiac ablation, typically low frequency RF (300-700 KHz) is delivered into the tissue via the electrode, resulting in ohmic heating of the tissue at the electrode tissue interface. The inventors propose to redesign the electrode of the RF ablation catheters/devices as a RF/microwave antenna or antennae and measure the electrical properties of the electrode antenna or antennae via S11 and/or S21 measurements in real-time during ablation as a method to monitor/assess extent of ablation/lesion formation. By detecting the changes in the characteristic electrical properties of the antenna or antennae during the ablation process (which are in the high frequency range 1 MHz-4 GHz or higher), we can infer the changes in the electrical properties of the tissue being ablated. Since the RF energy penetration varies with frequency, measurement of the antenna electrical properties in the frequency domain will enable infer tissue electrical properties along the thickness, and monitoring changes in the time domain during the ablation process will enable infer ablation lesion extent, quality and progression.

The electrical characteristics e.g. return loss v/s frequency of the antenna electrode is a function of the physical and electrical properties of the tissue in vicinity of the antenna electrode. The electrical characteristics of the antenna electrode, i.e. time domain frequency dips/peaks in return loss/reflection coefficient; are a function of dielectric properties, e.g. conductivity, relative permittivity and temperature of the tissue in contact. Thus changes to the time domain frequency dips/peaks in return loss/reflection. Similarly, coupling or electromagnetic (EM) transmission characteristic changes between two antennas can be used to infer changes in tissue properties between two antennas.

Conventional ablation systems lack a significant capacity to accurately assess lesion formation and characterize tissue in real-time during an ablation procedure. As such, there exists a need for an ablation catheter system with an electrode designed as an RF/microwave antenna as well as methods to monitor/assess lesion progression.

SUMMARY OF THE DISCLOSURE

The present disclosure provides a system with an innovative electrode designed as an RF/microwave antenna as well as methods to monitor/assess biological tissue and perform surgical procedures.

In one aspect, the disclosure provides an ablation device. The device includes at least one antenna configured to transmit and receive assessment signals having frequencies of at least 1 MHz to and from tissue; and a high frequency output configured to output the received assessment signal to a network analyzer and signal processing device, wherein the at least one antenna is further configured to transmit an ablation signal to the tissue.

In another aspect, the disclosure provides a device for assessing the state of a biological tissue. The device includes at least one antenna configured to transmit and receive assessment signals having frequencies of at least 1 MHz to and from tissue; and a high frequency output configured to output the received assessment signal to a network analyzer and signal processing device.

In yet another aspect, the invention provides a system for assessing the state of a biological tissue. The system includes a network analyzer and signal processing device including a high frequency input configured to receive a received assessment signal from tissue via a catheter, the received assessment signal having a frequency of at least 1 MHz; and a processor configured to detect an electrical property of the received assessment signal and determine a property of the tissue based on the detected electrical property of the received assessment signal.

In still another aspect, the disclosure provides a method for determining a property of a tissue. The method includes:

transmitting, with at least one antenna of a catheter, a transmitted assessment signal having a frequency of at least 1 MHz to tissue;

receiving, with the at least one antenna, a received assessment signal having a frequency of at least 1 MHz from the tissue;

detecting, with a processor of a network analyzer and signal processing device, an electrical property of the received assessment signal; and determining, with the processor, a property of the tissue based on the detected electrical property of the received assessment signal.

In yet another aspect, the invention provides a method of performing a surgical procedure using the device of the disclosure. In embodiments, the procedure includes ablation of tissue.

These and other embodiments are described in greater detail below, in reference to the attached drawings.

BRIEF DESCRIPTION OF THE DRAWINGS

FIG. 1 is an illustration depicting a conventional cardiac RF ablation catheter and electrode as well as anatomic representations of an ablation catheter in cardiac tissue and use on a patient.

FIG. 8A is a graph illustrating a return loss versus frequency profile.

FIG. 8B is a graph illustrating a return loss versus frequency profile.

FIG. 8C is a graph illustrating a return loss versus frequency profile.

FIG. 10A is a graph illustrating a return loss versus frequency profile.

FIG. 10B is a graph illustrating a return loss versus frequency profile.

FIG. 11A is a graph illustrating a return loss versus frequency profile.

FIG. 11B is a graph illustrating a return loss versus frequency profile.

FIG. 11C is a graph illustrating a return loss versus frequency profile.

FIG. 11D is a graph illustrating a return loss versus frequency profile.

FIG. 11E is a graph illustrating a return loss versus frequency profile.

FIG. 15A is a schematic view of an ablation needle electrode in one embodiment of the invention.

FIG. 22A is a schematic view of an antenna configuration which may be utilized in the needle electrode of the invention in one embodiment.

FIG. 22B is a schematic view of an antenna configuration which may be utilized in the needle electrode of the invention in one embodiment.

FIG. 22C is a schematic view of an antenna configuration which may be utilized in the needle electrode of the invention in one embodiment.

FIG. 22D is a schematic view of an antenna configuration which may be utilized in the needle electrode of the invention in one embodiment.

FIG. 22E is a schematic view of an antenna configuration which may be utilized in the needle electrode of the invention in one embodiment.

FIG. 22F is a schematic view of an antenna configuration which may be utilized in the needle electrode of the invention in one embodiment.

FIG. 22G is a schematic view of an antenna configuration which may be utilized in the needle electrode of the invention in one embodiment.

FIG. 22H is a schematic view of an antenna confiugration which may be utilized in the needle electrode of the invention in one embodiment.

FIG. 23B is a schematic view of the antenna electrode of FIG. 23A.

FIG. 24C is an expanded view of the tip of the antenna electrode of FIG. 23A.

FIG. 25A is a schematic view of an antenna electrode in one embodiment of the invention.

FIG. 25B is a schematic view of the antenna electrode of FIG. 25A.

DETAILED DESCRIPTION OF THE DISCLOSURE

Figure 2A:
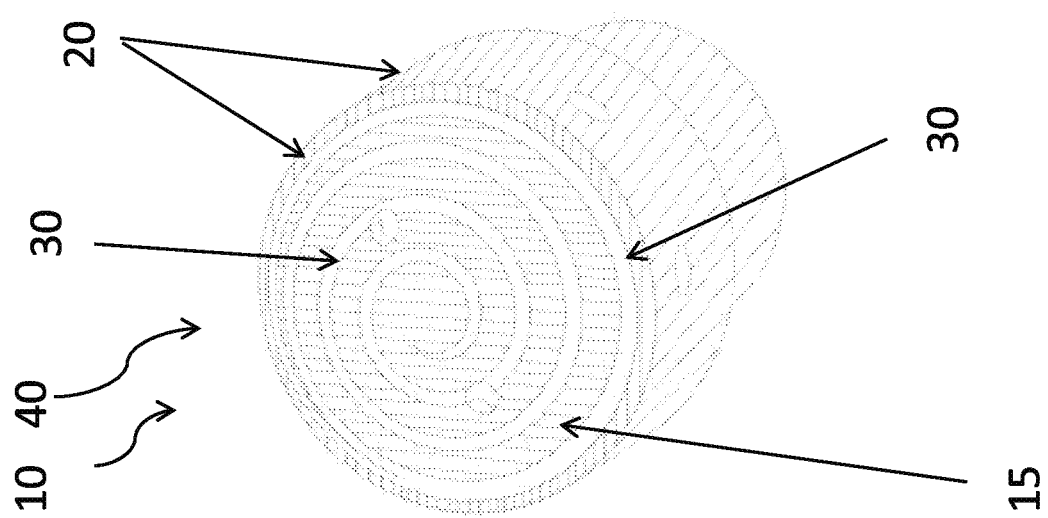
FIG. 2A is a schematic view of an antenna electrode in one embodiment of the invention.

In one aspect, the present disclosure provides a system for assessment of biological tissue by measuring/monitoring characteristics of electromagnetic radiation on biological tissue. The includes a device having at least one antenna configured to transmit and receive assessment signals having frequencies of at least 1 MHz to and from tissue; and a high frequency output configured to output the received assessment signal to a network analyzer and signal processing device.

In one embodiment the system is an ablation lesion assessment system. In embodiments, the system includes an RF ablation catheter with an antenna electrode, and optionally a vector network analyzer connected to the antenna electrode to enable reflection transmission measurements in a frequency range, i.e. S parameter measurements (S11 and S21/S12), data acquisition and an analysis interface which predicts extent of tissue-electrode contact and lesion progression in real-time is described.

In addition to measuring endocardial potential and delivering ablation RF (300-900 KHz range), the electrode of the RF ablation catheter is designed to have an additional functionality of an RF/microwave antenna. This enables the electrode to transmit and receive electromagnetic energy/frequencies in DC to GHz frequency range to the tissue being ablated, thus transmitting ablation energy at 100-700 KHz, sensing endocardial potential, as well as measuring S parameters in the KHz-GHz frequency range.

The present disclosure provides various embodiments of the antenna electrode of the invention. In various embodiments, the antenna electrode is described as being incorporated in various devices, such as, RF ablation catheters, microwave ablation catheters, intramyocardial injection catheters, thermoacoustic imaging catheters, magnetic resonance imaging (MRI) catheters which enable delivery of ablation energy and transmission/receiving of MR signals, all of which have the ability to enable monitor lesion assessment in real-time. However, the device of the invention need not be configured to ablate tissue but rather solely monitor the state of biological tissue.

This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. References to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the invention, the preferred methods and materials are now described.

FIG. 1 illustrates a conventional steerable cardiac RF ablation catheter with the ablation electrode at the distal end and handle at the proximal end. During an intracardiac RF ablation procedure for treatment of cardiac arrhythmias, an ablation catheter is introduced in the cardiac chamber via the venous approach and a ground pad is placed on the skin to complete the RF circuit. The ablation electrode is placed in contact with the cardiac tissue to be ablated and RF energy is delivered to the tissue to be ablated. Passage of a high frequency alternating current into the tissue causes local thermal injury, killing the tissue in contact with the electrode to create an ablation lesion, which results in conduction blocks. To ensure controlled thermal injury to the myocardial tissue, the ablation electrode needs to be in good electrical contact with the myocardial tissue and the ablation procedure needs to be monitored till desired depth of tissue is ablated. To monitor the cardiac ablation procedure, the inventors have redesigned the ablation electrode of the cardiac ablation catheter as a RF/microwave antenna. The reflection transmission electrical properties of the antenna electrode of the disclosure in the frequency domain during the duration of the ablation procedure is assessed to monitor procedure parameters and assess lesion formation, i.e., confirm electrode-tissue contact, confirm RF energy delivery to tissue, and confirm and assess lesion formation, i.e. depth of the lesion/tissue ablated, rate of ablation to ensure safe ablation and avoid excessive RF ablation.

Figure 2B:
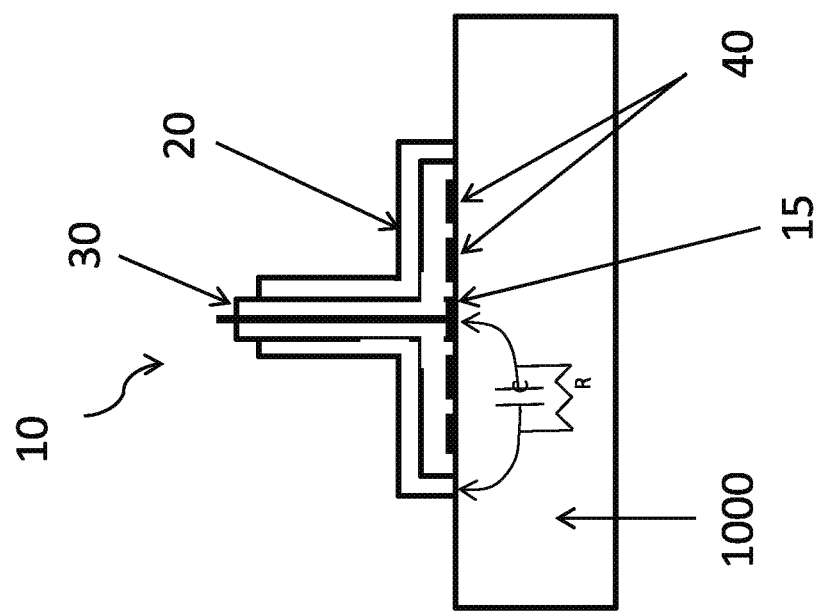
FIG. 2B is a cross-sectional view of the antenna electrode of FIG. 2A.
Figure 2C:
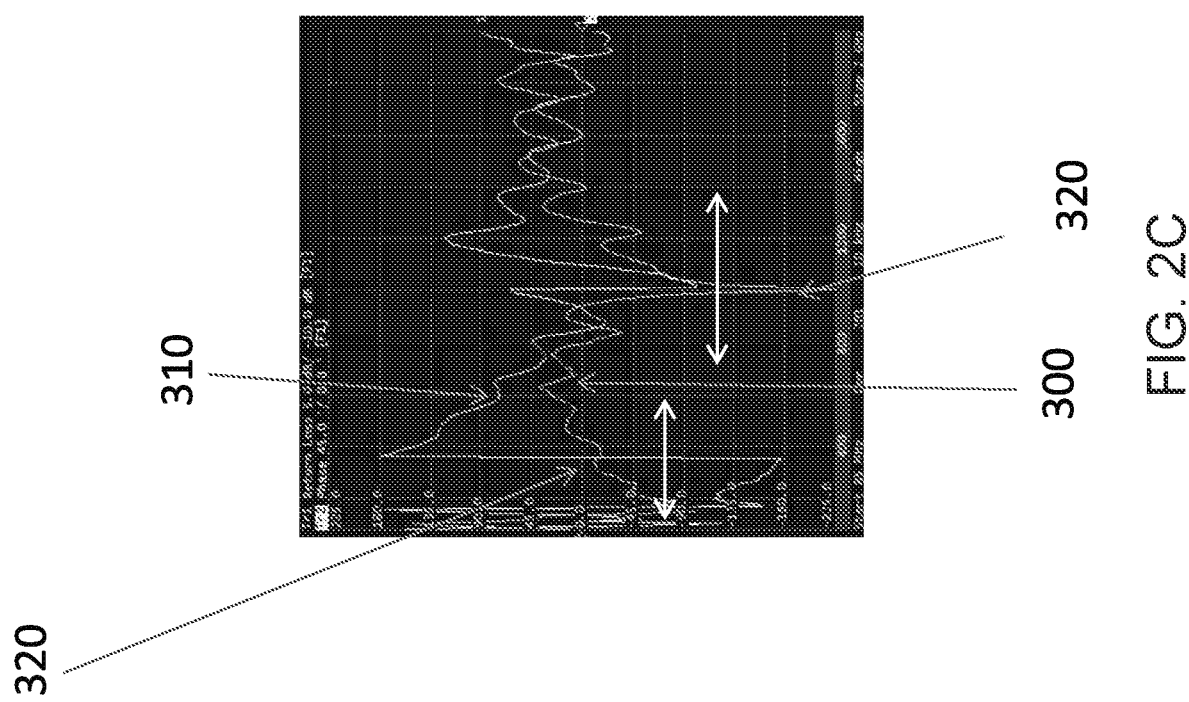
FIG. 2C is a graphic showing data generated using the antenna electrode of FIG. 2A.

FIG. 2A is a schematic of an antenna electrode 10 in one embodiment of the invention where the antenna electrode is a spiral antenna electrode 40. The spiral antenna electrode has a spiral positive plane 15 which is a helical spiral with each spiral separated by a dielectric 30. The positive spiral 15 is surrounded by a ground plane 20 separated by a dielectric 30. FIG. 2B shows a schematic of the spiral antenna electrode 40 on a tissue 1000 and electromagnetic model of tissue being ablated. FIG. 2C shows characteristic return loss 300 and phase angle 310 response in the frequency domain from 85 MHz to 2 GHz in a physiological saline solution using antenna electrode 10. Note the 180° phase shift that occurs at the resonant frequencies 320 at 350 MHz and 1000 MHz. As the dielectric properties of the medium surrounding the antenna changes, the return loss and phase angle profiles in the frequency domain change, and the resonant frequencies change as well. White arrows indicate the direction of shift in resonant frequencies as the dielectric properties of the medium change. By monitoring the return loss, phase angle profiles of the antenna electrode in the frequency domain and changes in resonant frequencies during the ablation procedures, the procedure parameters can be inferred and lesion formation can be monitored and assessed.

Figure 3:
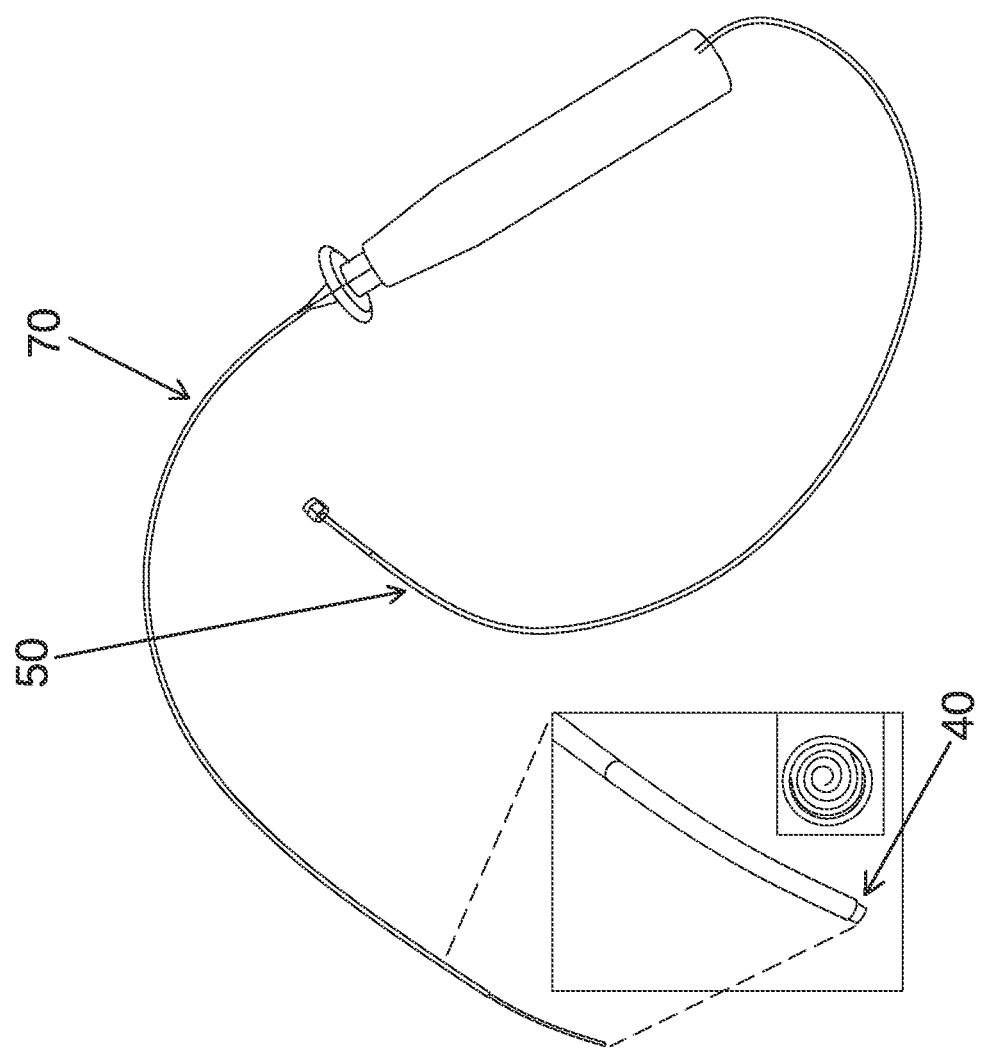
FIG. 3 is an illustration of an antenna electrode incorporated into a steerable catheter in one embodiment of the invention.

FIG. 3 illustrates a prototype spiral antenna electrode 40 incorporated into a steerable catheter 70 for performing percutaneous intracardiac RF ablations. The distal deflectable section and spiral antenna sensor electrode are shown in the inset. A coaxial cable 50 runs along the length of the catheter 70 and connects to the interface circuit including low pass filters, high pass filters, RF generator and vector impedance network analyzer, to simultaneously deliver high frequency sensing signals (MHz-GHz) to and from the antenna electrode and low frequency ablation RF (KHz) to the tissue via the electrode, and a very low frequency (DC) endomyocardial electrogram (EEG) signal from the myocardium to the EEG recording system.

The antenna electrode of the invention is configured to output energy that ablates tissue. The terms "ablate" or "ablation", including derivatives thereof, include, without limitation, substantial altering of electrical properties, mechanical properties, chemical properties or other properties of tissue. The term electrode within the context of "antenna electrode" includes a discrete element, such as an electrode, or a plurality of discrete elements, such as a plurality of spaced apart electrodes, which are positioned so as to collectively treat a region of tissue or discrete sites. One embodiment of an antenna electrode emits energy that ablates tissue, i.e., cardiac tissue, when the element is coupled to and energized by an energy source. Examples of energy emitting ablation electrodes include, without limitation, electrode elements coupled to direct current (DC) sources or alternating current (AC) sources (e.g., radiofrequency, RF, current sources), antenna elements energizable by microwave energy sources, pulsed high voltage sources, heating elements (e.g., metallic elements or other thermal conductors which are energized to emit heat via convective heat transfer, conductive heat transfer, and the like), light emitting elements (e.g., fiber optics capable of transmitting light sufficient to ablate tissue when the fiber optics are coupled to a light source), light sources (e.g., lasers, light emitting diodes, and the like), ultrasonic elements such as ultrasound transducers adapted to emit ultrasound waves sufficient to ablate tissue when coupled to suitable excitation sources), combinations thereof and the like.

As used herein, the term "ablate," including variations thereof, is construed to include, without limitation, to destroy or to permanently damage, injure, or traumatize tissue. For example, ablation may include localized tissue destruction, cell lysis, cell size reduction, necrosis, or combinations thereof.

In some embodiments, the ablation device may be connected to an energy generator (e.g., RF) by electrical conductors within the shaft of the ablation device or otherwise incorporated into the ablation system. RF energy may be outputted to a desired frequency based on the treatment. Example frequencies include, without limitation, frequencies in the range of about 50 kHz to about 1000 MHz (e.g., 300 to 700 kHz). When the RF energy is directed into tissue, the energy is converted within the tissue into heat allowing the temperature of the tissue to be increased, for example to a range of 40° C. to about 99° C. In some embodiments, a temperature sensor may be used to monitor the temperature of the target tissue to confirm therapeutic delivery of RF. A temperature sensor may also be used to monitor temperature of non-target tissue to reduce or avoid iatrogenic injury.

While the device of the antenna electrode of the invention is described generally with reference to use of RF, the antenna electrode described herein can be used for Microwave Radiometry applications and therefor may be connected to an energy generator that generates microwave energy, e.g., energy having a frequency of between about 300 MHz and 300 GHz.

In some embodiments the ablation electrode may be an RF electrode in monopolar configuration with a dispersive grounding pad on the patient's skin to complete the electrical circuit. In other embodiments, the configuration of the RF electrode may be bipolar. Ablation energy may be radiofrequency electrical current having a frequency up to 1 MHz, 50 MHz or 100 MHz or in a range of about 300 to 1 MHz or about 300 to 700 kHz and a power in a range of about 1 to 50 W. The delivery of RF energy may be controlled by an energy generator associated with a controller that uses temperature feedback from a sensor associated with the system. In some embodiments the antenna electrode functions to emit a substance as an ablation agent. In such embodiments the system may further comprise a means to inject the substance such as a manually operated syringe or automatically controlled pump. The emitted substance may be saline, phenol, ethanol, botulinum toxin or other neurotoxins, anesthetic agent, including but not limited to depolarizing or non-depolarizing agents, such as marcaine, bupivacaine, lidocaine, or other anesthetic agents, and other agents capable of reducing nerve signal transmission.

Figure 4A:
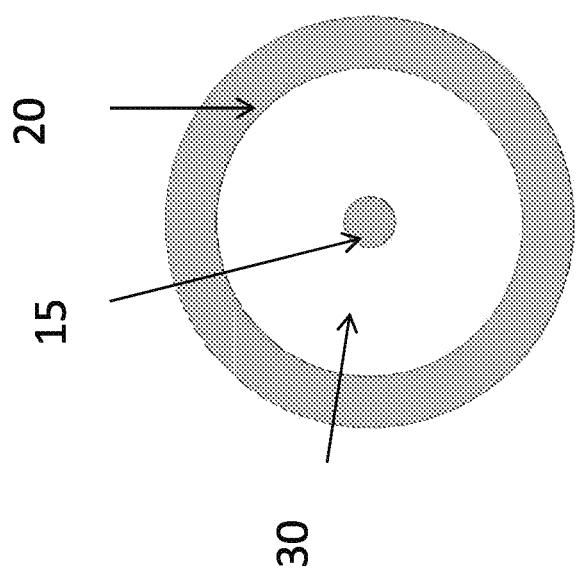
FIG. 4A is a cross-sectional view of a coaxial sensor on one configuration.
Figure 4B:
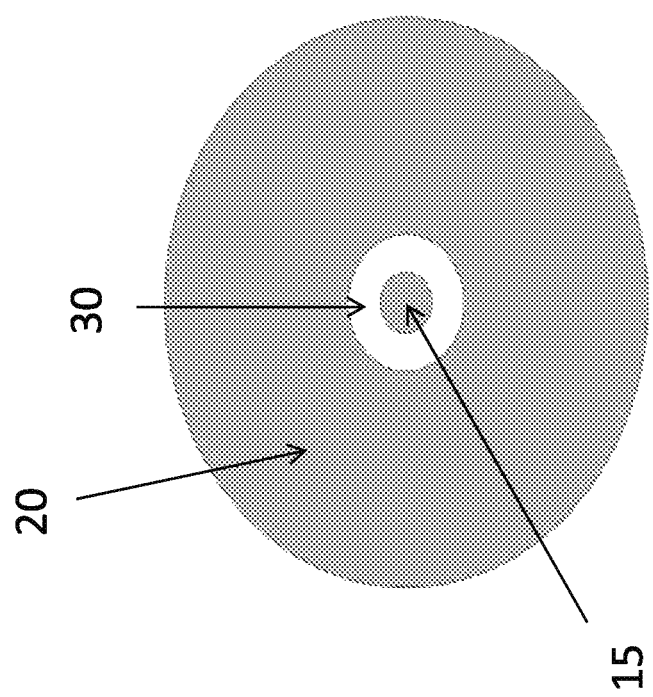
FIG. 4B is a cross-sectional view of a coaxial sensor on one configuration.
Figure 4C:
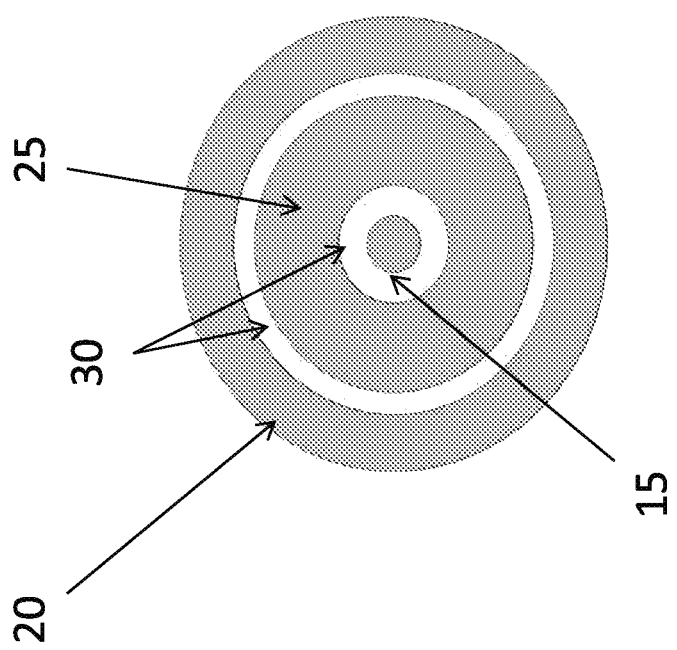
FIG. 4C is a cross-sectional view of a coaxial sensor on one configuration.
Figure 4D:
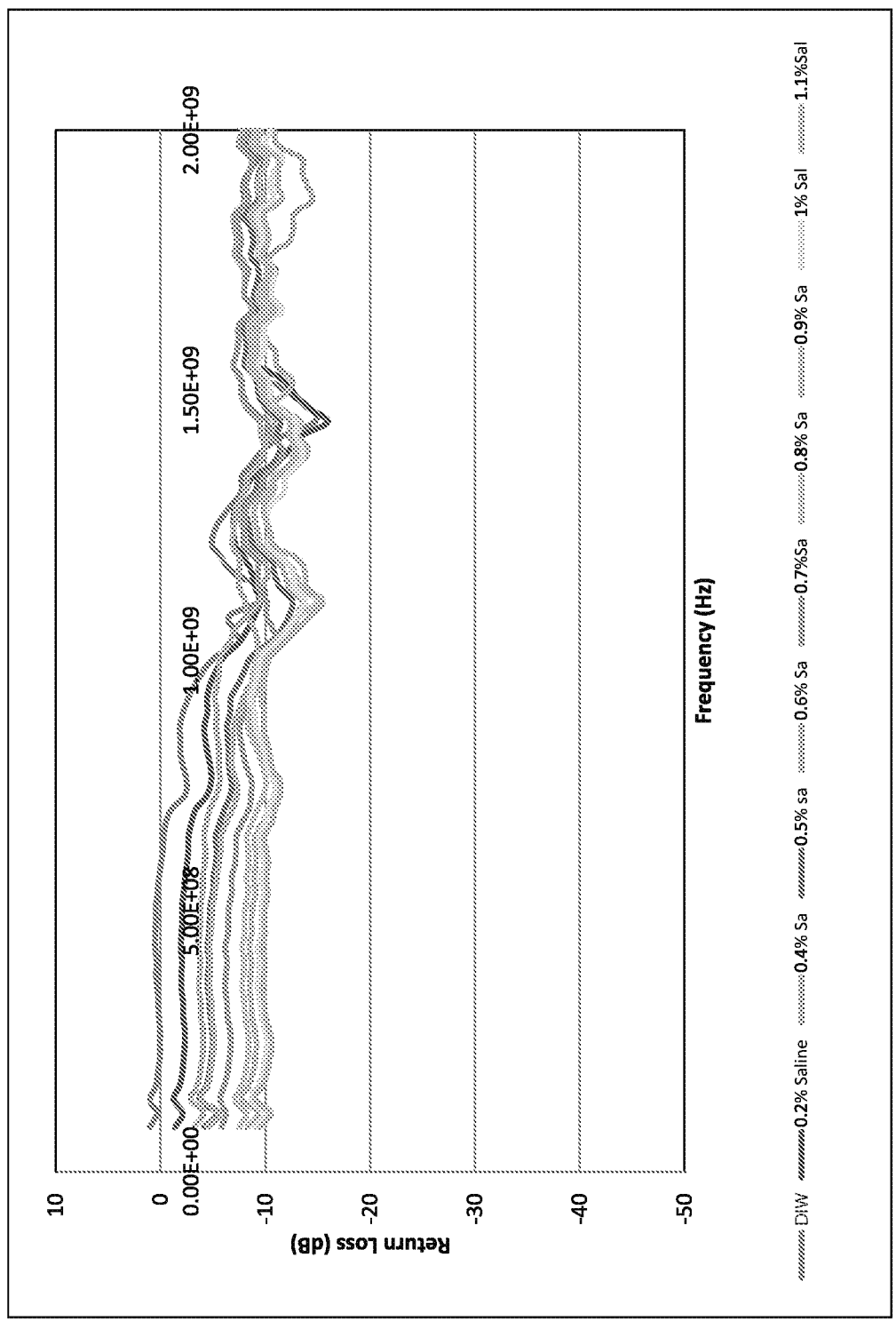
FIG. 4D is a graph illustrating a return loss versus frequency profile generated via the sensor of FIG. 4B.

FIGS. 4A-C provide schematics of various configuration of coaxial sensors. Schematics shown in FIGS. 4A and B depict positive plane 15 and circular ground plane 20 of the coaxial sensor separated by dielectric 30. The surface areas of the positive plane, ground plane and the separation between them can be varied which affects the return loss characteristics in the frequency domain. FIG. 4C shows a coaxial sensor with an intermediate floating plane 25 which is not connected to either. FIG. 4D shows characteristic return loss versus frequency profiles for the coaxial antenna sensor electrode of FIG. 4B in saline solutions of concentrations ranging from DI water to 1.1% saline. No distinct resonant frequencies can be seen, making it difficult to implement this design in an antenna electrode configuration.

Figure 5A:
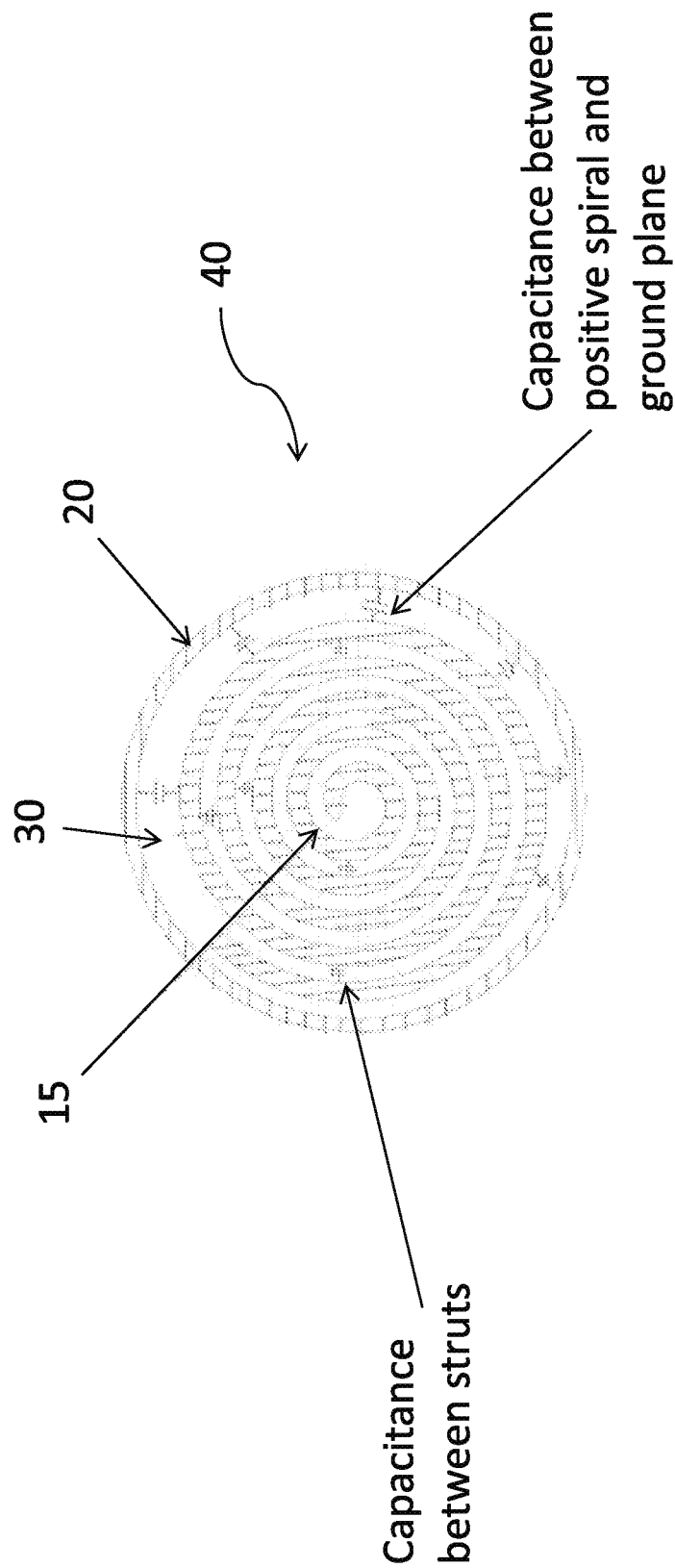
FIG. 5A is a schematic view of a spiral antenna electrode in one embodiment of the invention.
Figure 5B:
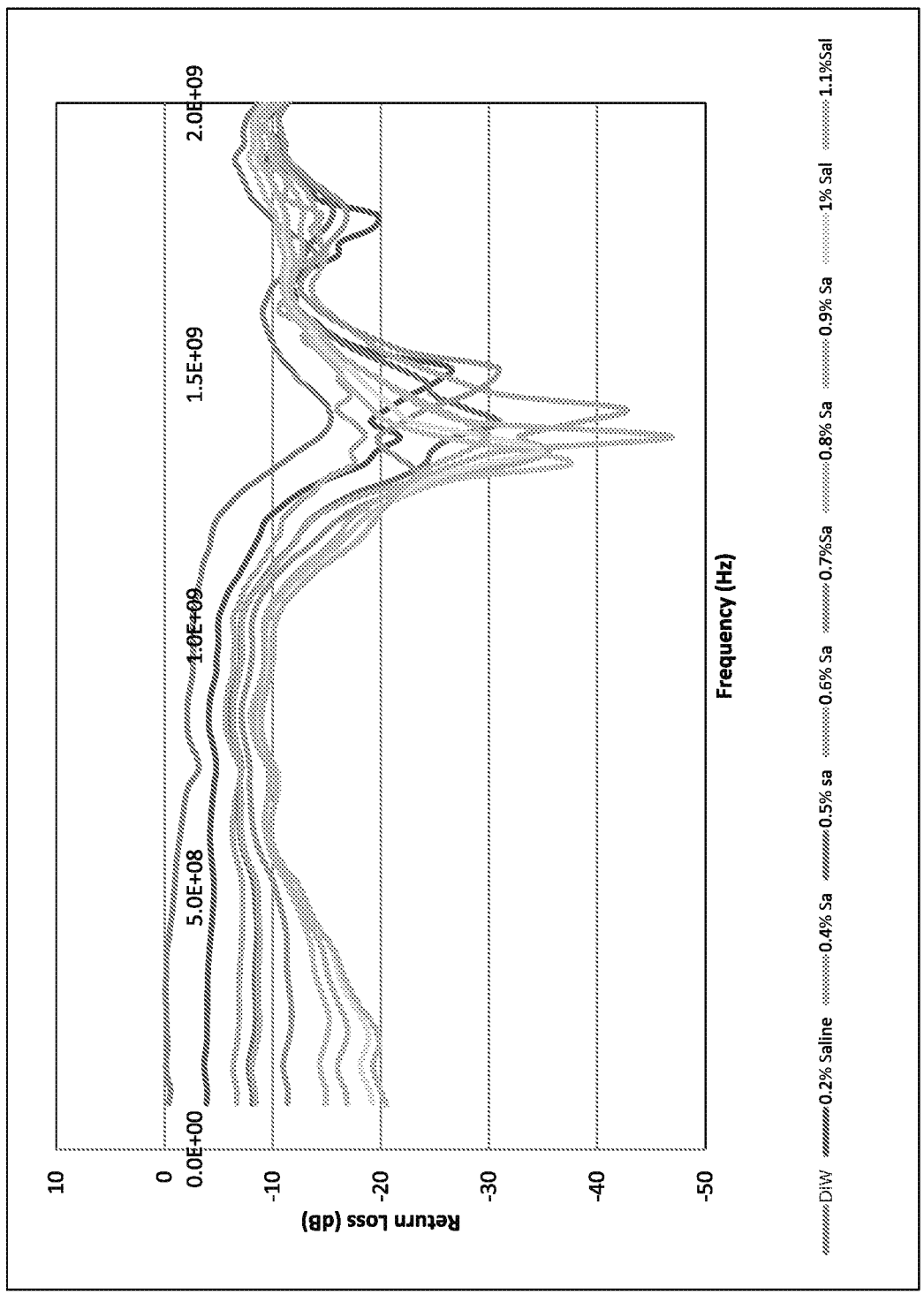
FIG. 5B is a graph illustrating a return loss versus frequency profile generated via the antenna of FIG. 5A.

FIG. 5A is a schematic of a spiral antenna electrode 40 with a spiral positive plane 15 where each strut is separated by a dielectric 30 and surrounded by a ground plane 20; again separating the ground plane and the spiral is a dielectric. The spiral acts as an inductor and the stray capacitance between the struts and between the positive plane and the ground plane, results in giving this antenna a characteristic return loss profile with a resonant frequency. FIG. 5B shows the return loss versus frequency profiles for the spiral antenna electrode 40 in saline solutions of concentrations ranging from DI water to 1.1% saline. The spiral antenna electrode of this design has a distinct resonant frequency at about 1400 MHz for all concentrations of saline solution. However, as the saline concentration increases the return loss decreases at lower frequencies; particularly between 10-500 MHz. The spiral antenna electrode's reflection properties in the frequency domain are a function of electrical properties of the medium, i.e. conductivity and permittivity of the medium can be used to monitor RF ablation procedures and assess lesion formation in embodiments of the invention.

Figure 6:
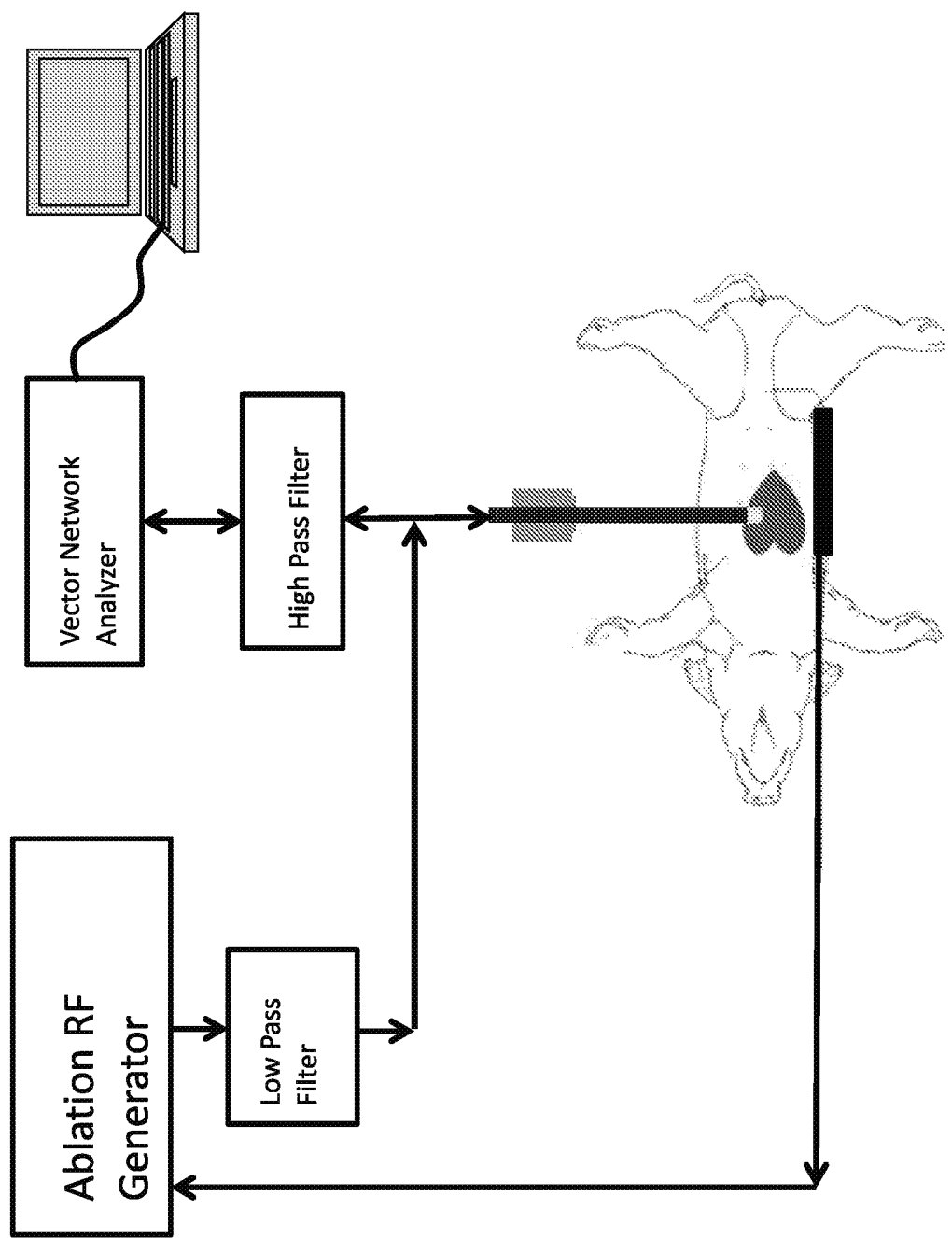
FIG. 6 is an illustration showing the layout of an experimental setup used to evaluate lesion assessment performance of an antenna electrode catheter of the invention in an animal.

FIG. 6 shows the schematic setup of the system of the invention used to evaluate ablation lesion assessment performance of an antenna electrode disposed in a catheter in an animal.

Figure 7:
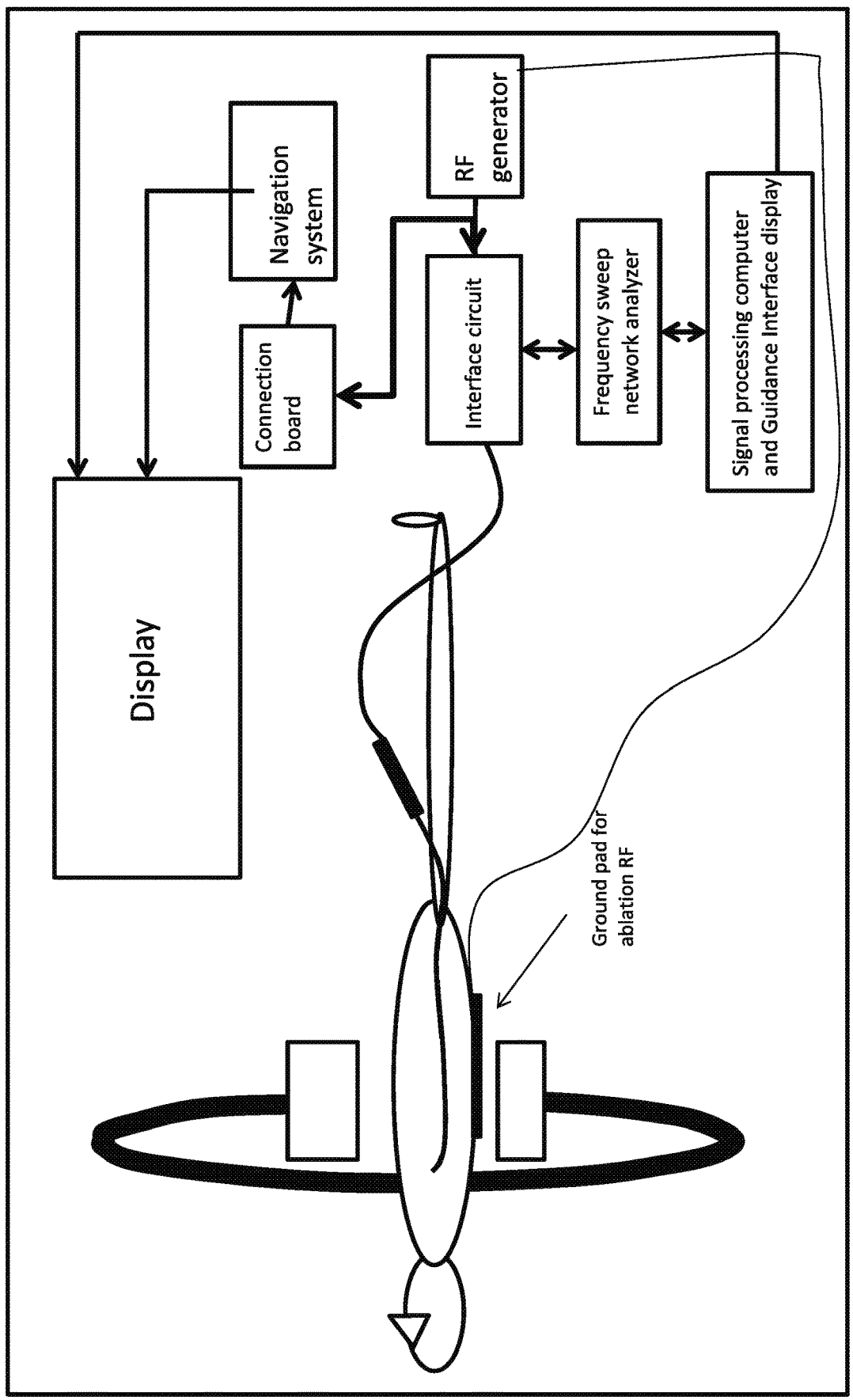
FIG. 7 is an illustration showing the layout of an ablation lesion assessment system of the invention for performing intracardiac ablation procedures.

FIG. 7 show the schematic of the RF ablation lesion assessment system of the invention for performing intracardiac RF ablation procedures. The ablation RF generator provides ablation RF energy in the 1 KHz to 1 MHz range. The network analyzer measures the reflection electrical properties of the antenna electrode in MHz and GHz ranges. Interface circuit comprises a low pass and a high pass filter. The output of the RF generator passes thru a RF low pass filter or a band pass filter to allow only the ablation frequencies to pass through and attenuates all other frequencies by over 40 dB, thus preventing transmitting frequencies which interfere with high frequency network analyzer signals and measurements. The input and output of the network analyzer passes thru a high pass filter or a suitable band stop filter, which attenuates the ablating frequency by over 40 dB thus preventing any damage to the sensing hardware and has minimal insertion loss at all other frequencies. The vector network analyzer sends an incident signal to the antenna electrode in the MHz-GHz frequency range; the difference in amplitude and phase of the transmitted and reflected signals are used to compute the return loss and phase angle properties of the antenna electrode in the frequency domain. These are processed and recorded via a computer or other hardware, and displayed during clinical use to monitor the procedure and assess and monitor lesion formation.

In various embodiments, the system includes a low pass and high pass filter which may be band pass/band stop filters and an RF generator that has a range of about 10 Hz to 100 MHz.

FIG. 8 shows the return loss and phase angle responses of the spiral antenna electrode 40 in the frequency domain when in blood (FIG. 8A), in contact with epicardial tissue (FIG. 8B) and in contact with fatty tissue section on the epicardium (FIG. 8C). During clinical use the catheter with the antenna electrode 40 is advanced in the cardiac chambers. When the electrode is in blood, the characteristic return loss profile 300, phase angle profile 310, and resonant frequency 320, at ~325 Hz, as shown in FIG. 8A, are dependent on antenna electrode design and can change from one design to another. Depending on extent of tissue contact and orientation of contact; this changes as shown in FIG. 8B with a flattening of the return loss profile 300 and shift in resonant frequency 320 to about ~400 MHz. Depending on the nature of tissue, i.e. fatty or ablated tissue or scar tissue, further increase in resonant frequency might be exhibited.

Figure 9C:
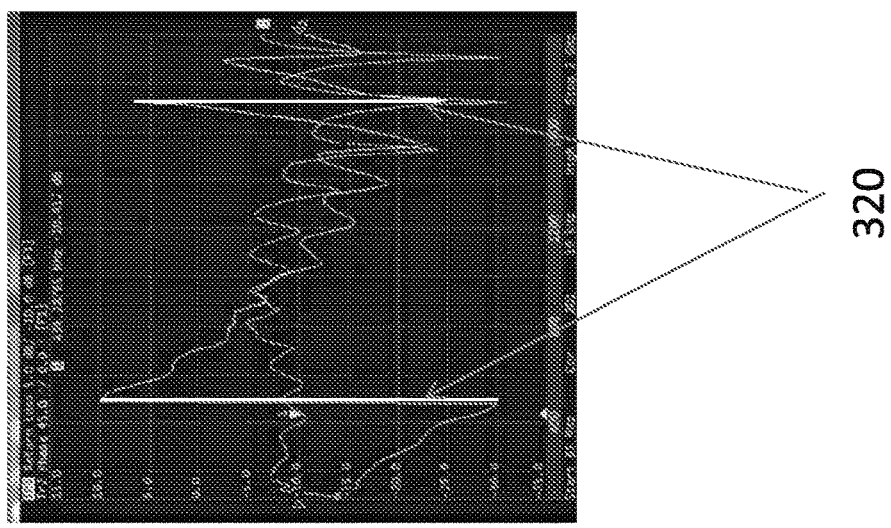
FIG. 9C is a graph illustrating a return loss versus frequency profile.
Figure 9B:
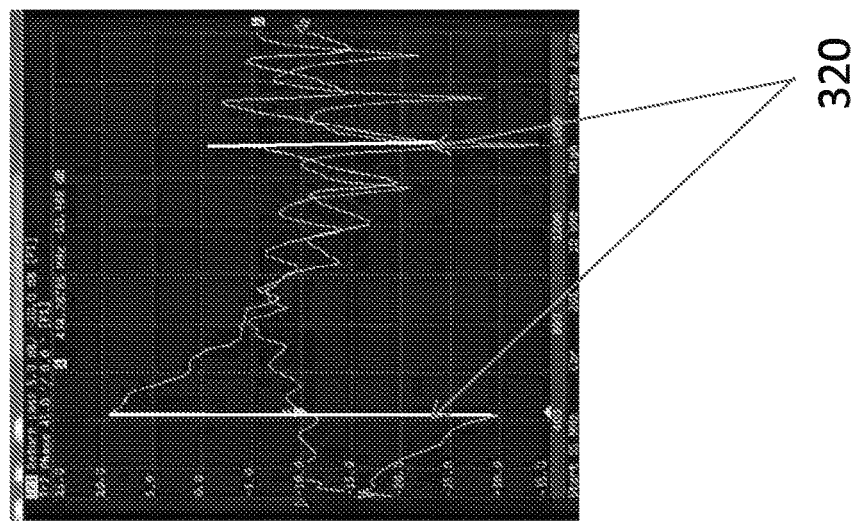
FIG. 9B is a graph illustrating a return loss versus frequency profile.
Figure 9A:
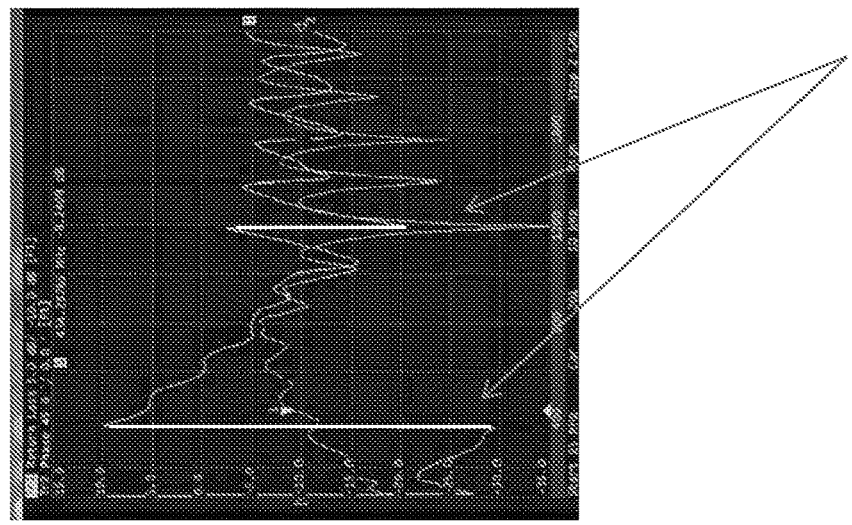
FIG. 9A is a graph illustrating a return loss versus frequency profile.

FIG. 9 shows return loss, phase angle characteristic of the antenna electrode 40 in a wider frequency range, i.e. 100 MHz to 2 GHz. In this frequency range two distinct resonant frequencies can be observed. Extent of electrode tissue contact may be assessed using one or more resonant frequencies 320, e.g. at ~350 MHz and 1200 MHz (FIG. 9A) when the electrode is in blood or saline, which then shifts to 400 and 1500 MHz (FIG. 9) depending on extent of electrode-tissue contact. If the electrode is fully in contact with ablated tissue, the resonant frequency 320 may shift to 525 and 1700 MHz (FIG. 9C). The shift in resonant frequency from antenna-electrode in blood, to antenna-electrode on tissue can be used to determine the antenna-electrode surface area in contact with tissue.

During the ablation procedure, it is important to maintain good electrode contact with tissue to ensure RF energy deposition in the tissue. With a moving heart wall this can be difficult and it is important for the physician to confirm RF energy deposition in the tissue. The antenna electrode 40 shows characteristic return loss and phase angle profiles when RF energy delivery is in blood. FIG. 10A shows a return loss and phase angle profile when antenna electrode is in blood and 10B shows the same when ablation RF is turned on (with electrode in blood). When the electrode is in blood, the phase angle reversal/resonant frequency is ~325 MHz (FIG. 10A); when RF ablation is turned on, this phase angle reversal/resonant frequency drops to ~200 MHz and stays there. This distinct characteristic return loss 300, phase angle 310 and resonant frequency 320 response (FIG. 10B) when RF energy is delivered in blood notifies the physician of the loss of electrode-tissue contact.

With reference to FIG. 11, progression of lesion formation is indicated by the return loss profiles 300 and phase angle profiles 310 in the frequency domain at different time points in the ablation procedure. When RF energy deposition in tissue is translated into tissue temperature rise and thermal tissue damage, an ablation lesion is created. This lesion formation process can be discerned by monitoring return loss profiles 300, phase angle profiles 310 and phase reversal frequencies 320 in the frequency domain during the ablation procedure (FIGS. 11A-E). The return loss 300 profile is flat when the electrode is in contact with tissue and phase reversal frequency is ~400 MHz (FIG. 11A), on onset of RF ablation phase reversal frequency 320 drops to 250 MHz and a dip in return loss 300 is seen at ~200 MHz (FIG. 11B); as ablation progresses phase reversal frequency 320 increases gradually to 400, 600 and steadies at 800 MHz for this antenna electrode design (FIGS. 11C-E). By monitoring the change in phase reversal frequency 320 and return loss profiles 300, thermal tissue damage can be confirmed. Thus, the return loss profile 300, phase angle profile 310 and resonant frequency/phase reversal frequency 320 can be used to infer electrode-tissue contact, confirm RF energy delivery to the wall and assess lesion formation.

Figure 12:
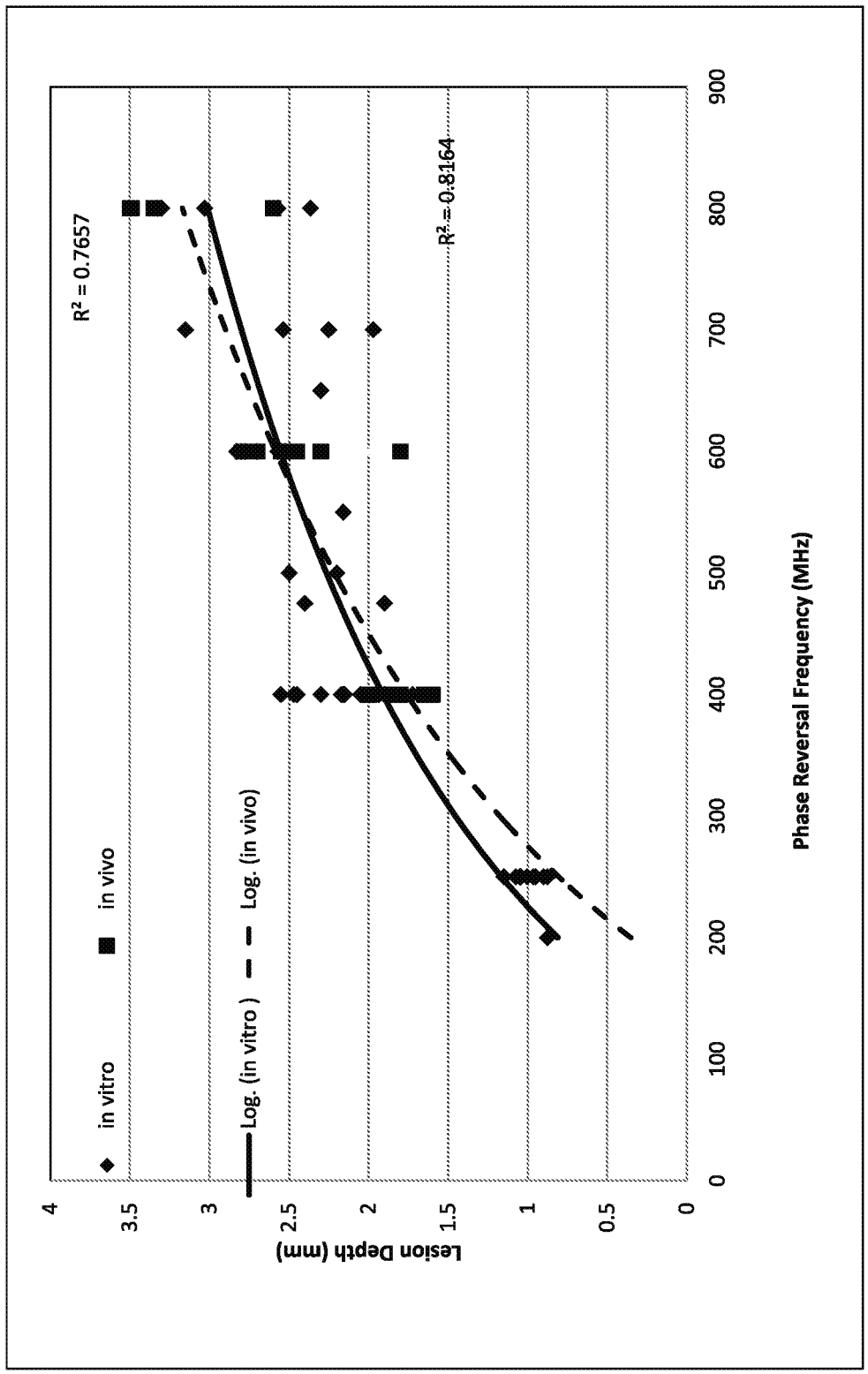
FIG. 12 is a graph illustrating the relationship between phase reversal frequency/resonant frequency and lesion depth.

FIG. 12 shows the relationship between phase reversal frequency/resonant frequency 320 and lesion depth. The resonant frequency/phase reversal frequency 320 observed during RF ablation procedure correlates to the depth of the lesion formed (FIG. 12) and the nature of the surface of the lesion. The phase reversal frequency observed during ablation can be used to estimate lesion depth under optimized conditions of saline flush irrigation, applied power and estimated electrode-tissue contact surface area. This methodology of using the return loss profiles 300, phase angle profile 310 of the antenna electrode to infer lesion depth can be implemented clinically to monitor and assess lesion formation in the system of the invention.

As it can be evidenced FIGS. 8-12 the return loss profile 300, the phase angle profile 320, the resonant frequency/phase angle reversal frequency 320 of the antenna electrode can be used to monitor cardiac RF ablation procedure parameters e.g. confirm and quantify electrode tissue contact, confirm RF energy deposition in blood, confirm lesion formation and assess lesion depth during the procedure. In a typical intracardiac ablation procedure the RF ablation catheter with the antenna electrode of the invention is advanced in the cardiac chambers using x-ray fluoroscopy guidance, with preoperative CT or MRI images. A baseline return loss, phase angle, resonant frequency data set is obtained with the antenna electrode in blood. Then the antenna electrode is contacted to the cardiac tissue in different orientations to get another baseline return loss, phase angle and resonant frequency data set with antenna electrode in contact with tissue. With the baseline data acquired and properties recorded, the physician gets the information on the return loss, phase angle and resonant frequencies that are needed to confirm contact and to quantify the extent of electrode-tissue contact i.e. surface area of electrode in contact with tissue. The ablation catheter is then steered to the anatomical region of interest to be ablated. Using the baseline data when antenna electrode was in blood and tissue, the physician confirms electrode-tissue contact, adjusts the catheter to maximize the contact; and delivers the ablation current into the tissue. Monitoring the resonant frequency changes, ensures that the electrode-tissue contact is maintained for the duration of ablation. By monitoring the resonant frequency progression, lesion formation is confirmed and ablation is stopped when resonant frequency reaches a desired set-point indicative of the lesion depth required at ablation location. Thus the RF ablation lesion assessment system of the invention including an ablation catheter with an antenna electrode, can be used to monitor cardiac RF ablation procedure and assess lesion formation by monitoring the reflection characteristics in the frequency domain via a vector network analyzer.

The purpose of the cardiac RF ablation procedure is to create a permanent conduction block. To achieve this it is important to ablate the entire wall thickness of the atria or ventricle safely, i.e. no excessive power during ablation which will cause steam pops or excessive duration of ablation which may cause perforation. To enable this, the RF energy input needs to be closely regulated throughout the procedure and electrode tissue-contact needs to be maintained. RF ablation primarily occurs by ohmic heating, where the tissue in contact with the electrode heats due to the current which passes thru it. This heat is then conducted deeper in the tissue, creating a deeper lesion. If the local tissue impedance rises significantly higher e.g. when tissue is charred, the RF power delivered by the electrode in the tissue is not effectively converted to heat and superficial lesions are created. For better clinical outcomes entire wall thickness of the atria needs to be ablated, e.g. 3-4 mm. To achieve this, local tissue impedance and temperature needs to be regulated at an optimum level i.e. the amplitude of power applied needs to be regulated. The rate of change of phase reversal (from 400 MHz to 250 MHz back to 400 MHz and higher) observed during the ablation procedure is a measure of the impedance of the tissue in contact with the electrode; to make deeper lesions the power level/wattage of RF deposition in the tissue and can be adjusted to hold the phase reversal frequency steady at 400-600 MHz by regulating the power applied. Thus deeper lesions can be created without causing excessive tissue heating, which results in surface charring or steam pops. Since the resonant frequency is held constant between a certain frequency range, resonant frequency alone cannot be used to assess lesion depth. Since lesion depth is also directly proportional to the total energy deposited in the tissue, the total power applied during the entire procedure or the total power applied when the resonant frequency was held constant in the selected frequency range, e.g. 400-600 MHz, may be used to estimate the lesion depth.

The complications during the procedure are caused by excessive ablation, i.e. excessively longer duration of ablation and/or by applying excessively high power. The rate of resonant frequency change during RF ablation is an indication of the dielectric properties change and temperature of the tissue in contact with the electrode. During the ablation procedure, there is a significant change in resonant frequency as ablation progresses, and the rate of resonant frequency/phase reversal frequency change is an indication of the rate of change of tissue electrical properties and tissue temperature; which is also a measure of amplitude of power applied. To create deeper lesions safely, the power input rate needs to be titrated which can be accomplished by a controller which monitors the rate of resonant frequency change and accordingly adjusts the power input. Alternately, the power input can be adjusted manually to maintain an optimum resonant frequency change rate.

The objective of the cardiac ablation procedure for treatment of complex arrhythmias e.g. atrial fibrillation, is to create contiguous transmural lesions within anatomical boundaries, e.g. around pulmonary vein ostia. The methods described earlier disclose using the RF ablation lesion assessment system of the invention to create lesions of known depths, thus transmural lesions may be created. To create contiguous lesions, the antenna electrode catheter needs to differentiate between ablated tissue and non-ablated tissue. In FIG. 9, the distinctly different return loss, phase angle and resonant frequency characteristics of the antenna electrode when in contact with blood, tissue and ablated tissue are shown. This feature can be used to identify the tissue type in contact with the catheter. This can be done in a clinical setting by steering the catheter to different points to create electrode-tissue contact, monitoring its return loss phase angle profiles and phase reversal/resonant frequencies to assess tissue type. The RF ablation lesion assessment system may be configured to have two modes, assessment mode and the ablation mode. Since adding RF filters in line will cause added electromagnetic system noise, a switch in the system will enable taking the filters off line and having the catheter directly connected to the network analyzer. The frequency range and amplitude of assessment/sensing signal could be higher for the purpose of assessment as well. The operator will have the option to select the modes; however, when ablation RF is turned on, the system will have an auto switch to ablation mode. To enable tissue assessment, the physician selects the assessment mode then obtains baseline data of return loss, phase angle and resonant frequency characteristics when the electrode is in blood, and contacting known healthy tissue in different orientations. Once this is done, the catheter is steered to the desired anatomical targets and return loss, phase angle, resonant frequency, and the like, properties are recorded; compared to the baseline data to infer tissue type in contact. The system can switch between assessment and ablation modes with a switch; or the ablation mode automatically engages when the RF switch is turned on.

Figure 13:
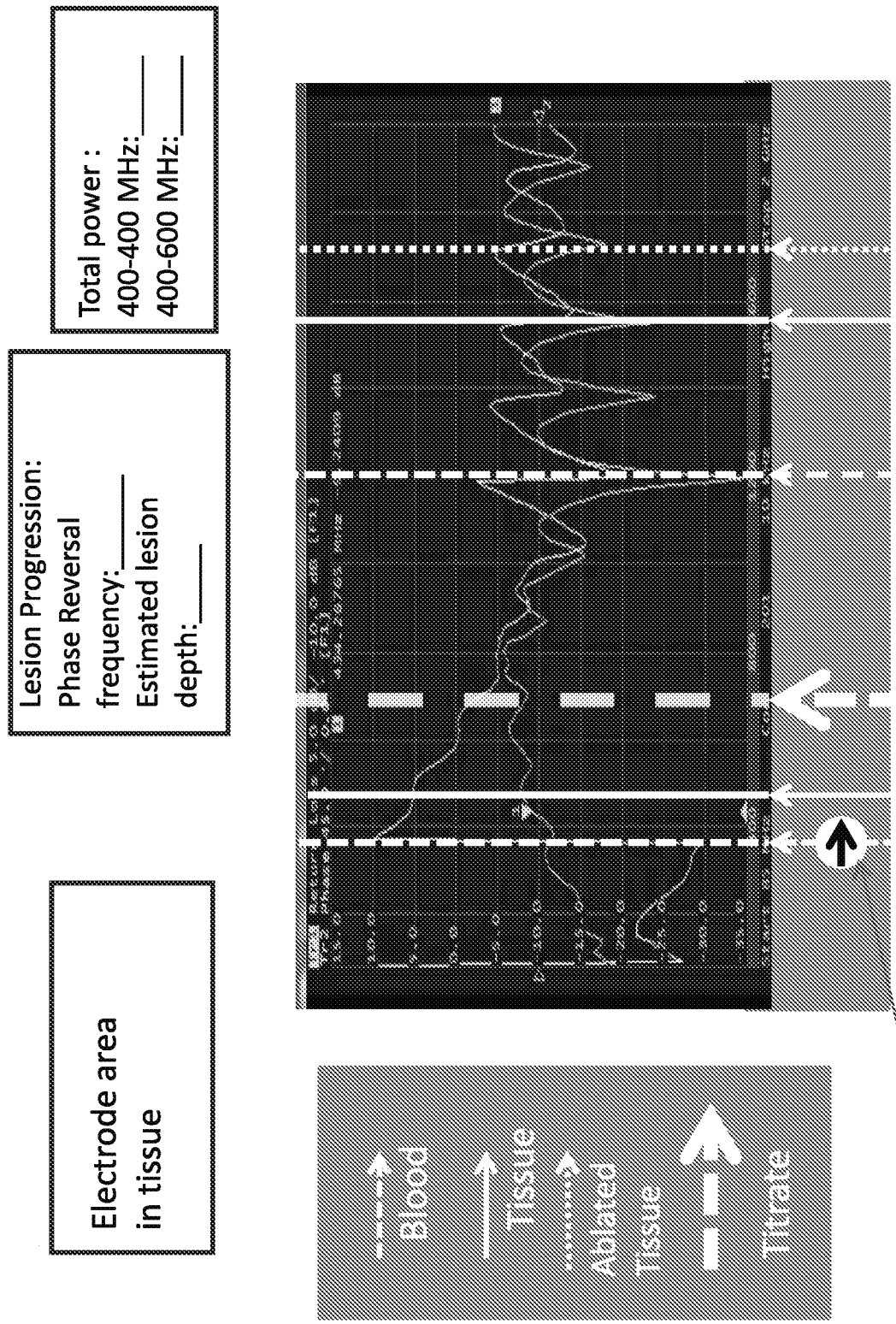
FIG. 13 is an illustration showing a user interface for monitoring an ablation procedure using the system of the invention.

FIG. 13 shows a graphical user interface which can be used to monitor ablation procedures and assess lesion formation. A suitable user interface indicates the different procedure parameters, i.e. area of tissue electrode contact, and the type of tissue in contact with electrode. Additionally, during RF ablation it includes an indication confirming RF deposition in tissue and assessment of lesion formation, i.e. rate of lesion formation and depth of lesion formation. Baseline/Benchmark assessment of different contact conditions are made prior to start of the procedure, e.g. electrode in blood, electrode in contact with tissue in different orientation, and the like. Before ablation, assessing the tissue type as ablated tissue, non-ablated tissue, blood, fatty tissue will be required. This will be done in the assessment mode. These can be indicated as a slide bar/graph with markings for blood, tissue, ablated tissue, and lesion depth are made on the scale, a sliding cursor/arrow indicates the position of the electrode at a given time. Area of electrode in contact with tissue before and during RF ablation needs to be continuously indicated. This can be the actual surface area, % of the area, and the like. During ablation, rate of RF input in terms applied wattage and saline flush rate may be entered in the system for estimating lesion depth and total power input. During the ablation process the rate of RF deposition in tissue will be displayed and quantified. This will be estimated on the total wattage applied, saline flush rate and shift in resonant frequency observed. Lesion progression will be displayed as an estimated lesion depth based on resonant frequency and total power deposited (as estimated from the electrode area in contact, saline flush rate and applied watts). Alerts indicating excessive ablation rate and unsafe surface conditions which will cause steam pops can be included.

Besides cardiac ablation, RF ablation is used for treatment of other clinical conditions e.g., nerve ablation for pain management, liver cancer tumor ablation, breast cancer tumor ablation, and the like. In these procedures a needle electrode/probe/device is placed in the tissue to be ablated using X-ray, ultrasound, CT or MRI guidance, it is then connected to the RF generator, a grounding pad is placed on the patient. RF wattage and time duration of RF application is based on physician experience and manufacturer provided estimates of ablation zone under given ablation conditions. The ablation needle-electrodes can be designed as RF/microwave antennae, and by monitoring the change in reflection transmission electrical properties in the frequency domain during the procedure enable infer ablation zone and extent of thermal injury. Devices and methods to intraoperatively access RF ablation zone/lesion, extent of thermal tissue damage and maximize ablation zone are described and included in the invention.

Figure 14A:
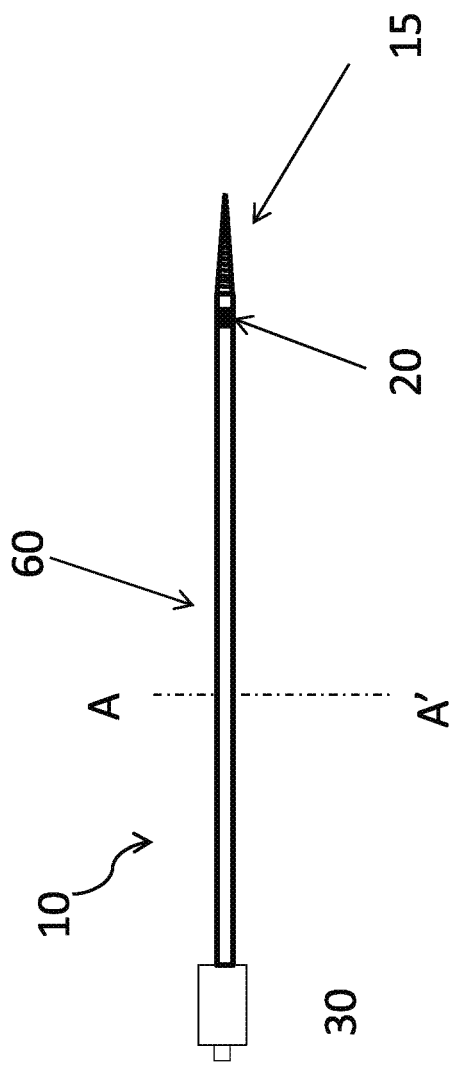
FIG. 14A is a schematic view of an ablation needle electrode in one embodiment of the invention.
Figure 14B:
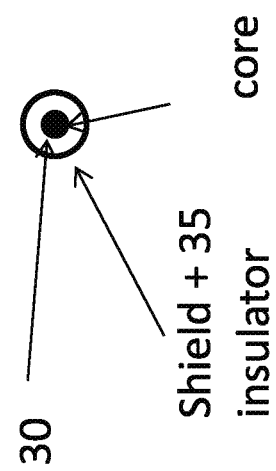
FIG. 14B is a cross-sectional view the electrode of FIG. 14A along line A-A'.

FIG. 14 shows the schematic of the RF ablation needle electrode of the invention as a modified dipole/monopole antenna. This configuration allows to transmit a broad range of frequencies form DC to few GHz to the antenna/tissue. The body of the ablation electrode 60 is configured as a coaxial cable in the proximal section (FIG. 14B) which comprises a core 'X' surrounded by a dielectric 30 with the shield 'X' and an outer insulator 35. The proximal section is insulated, in the distal end of the shield, e.g. few millimeters section, the insulator is removed, causing this section to acts as the ground plane 20 of the antenna. The distal section 15, is the positive of the antenna which is connected to the core of the coaxial cable at the distal tip of just distal to the ground plane of the antenna. The positive plane of the antenna comprises a helical coil wound on an insulator/dielectric material but has no dielectric or insulation covering the outer surface of the helical coil. The helical coil has closely wound pitch, and each turn is separated by a dielectric 30. The width of the turns of the helical coil may be uniform throughout the length of the coil or may vary from proximal to distal; which can potentially affect the sensitivity of the antenna electrode. In another configuration of the same design, the helical coil is replaced by a conductor wire or a tubing. The length of the helical coil and or the wire can vary from 2 mm to 15 cm. It can be straight, curved, shapeable or telescopic to adjust for different lengths and configurations. The ablation RF is delivered to the tissue from the positive plane of the antenna-needle but can be applied from both, the positive and the ground plane as well.

Figure 14C:
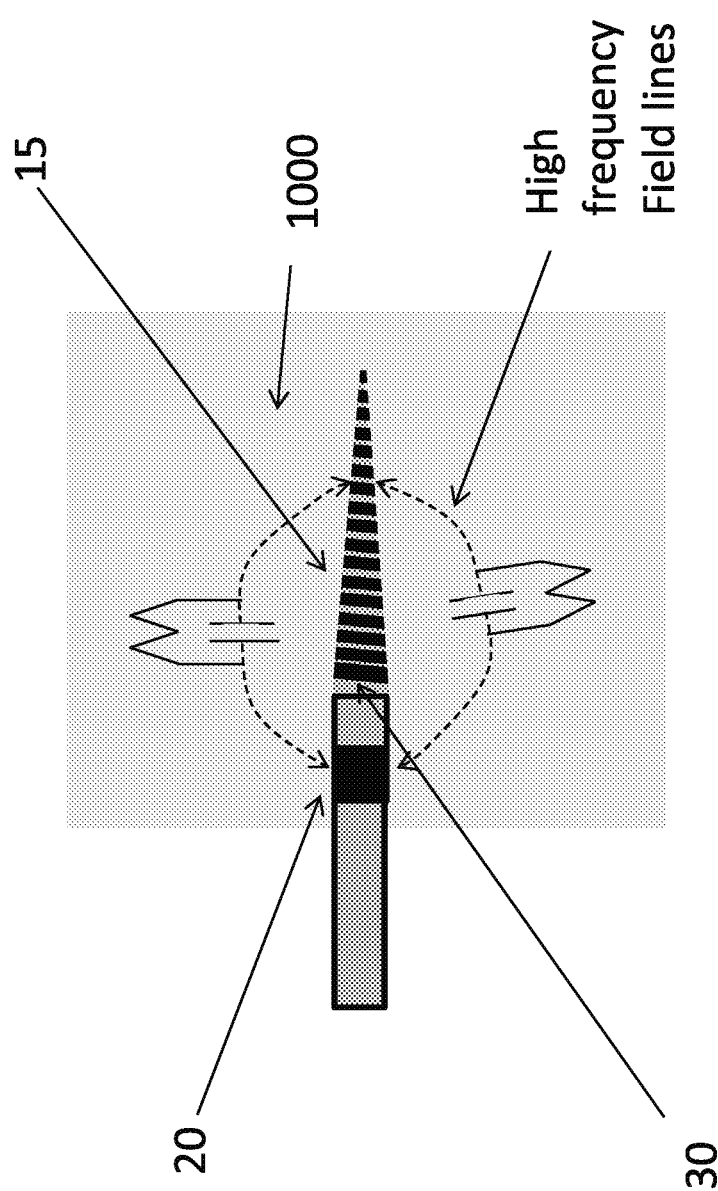
FIG. 14C is an expanded view of the tip of the ablation needle electrode of FIG. 14A.

FIG. 14C provides an electrical schematic of the antenna electrode when placed in a tissue. The tissue behaves as a capacitor and resistor in series. During the RF ablation procedure, as the dielectric properties of the tissue change, so do the reflection/transmission properties of the needle antenna electrode and the change used to quantify ablation zone and extent of thermal injury.

Figure 15B:
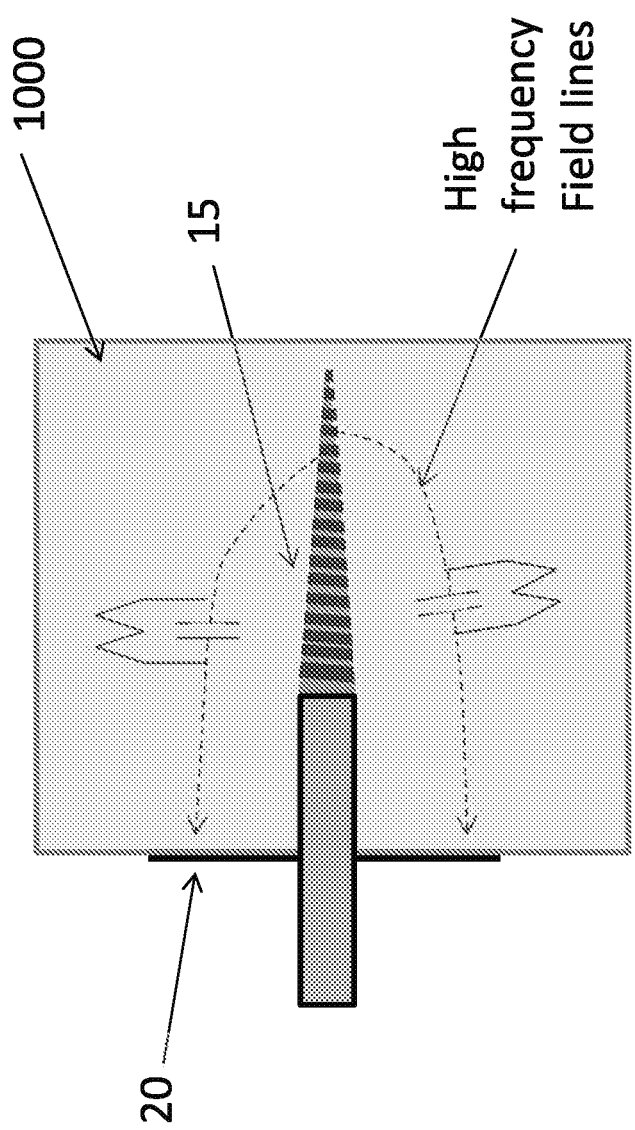
FIG. 15B is an expanded view of the tip of the ablation needle electrode of FIG. 15A.
Figure 15C:
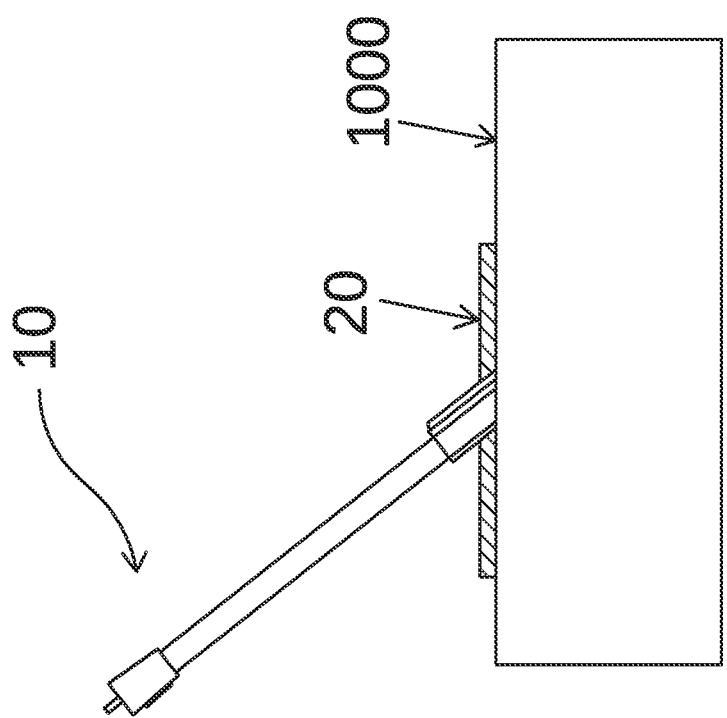
FIG. 15C is a schematic view of the ablation needle electrode of FIG. 15A inserted in tissue in one embodiment of the invention.
Figure 15D:
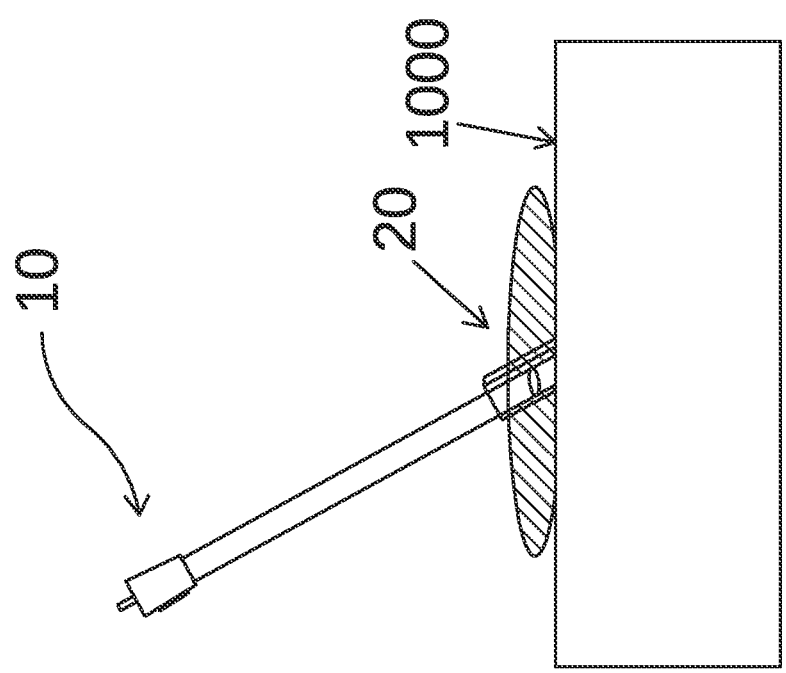
FIG. 15D is a schematic view of the ablation needle electrode of FIG. 15A inserted in tissue in one embodiment of the invention.

FIG. 15 shows a configuration for the RF ablation antenna needle electrode 10 with the ground plane 20 located on the outer surface of the body. This increases the sensing signal penetration, as shown by the field lines thru the entire thickness of the tissue (FIG. 15B and D). This is particularly useful for monitoring ablation of shallow lesions, not further out from the surface of the skin, where excessive ablation can cause burn wounds close to the surface of the skin. The ground plane 20 may be fixed to the electrode body or can be connected during the procedure by an number of external fixation methods, such as screw on attachments, gripper chucks, gripper jaws, and the like. The ground plane may be a conductor on a flexible dielectric surface, e.g. polymeric or fabric which is glued to the skin by an appropriate adhesive which does not attenuate conductivity.

Figure 16A:
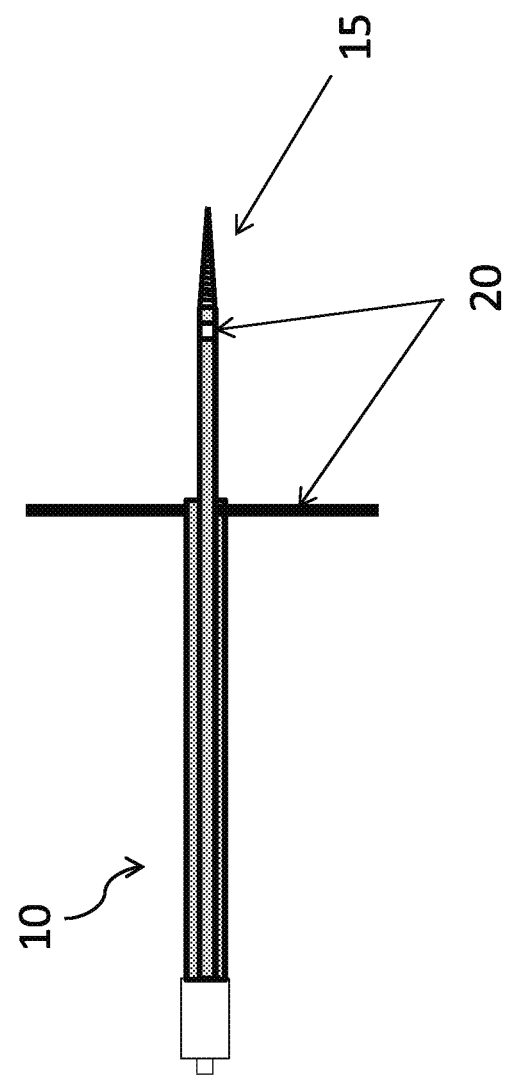
FIG. 16A is a schematic view of an ablation needle electrode in one embodiment of the invention.
Figure 16B:
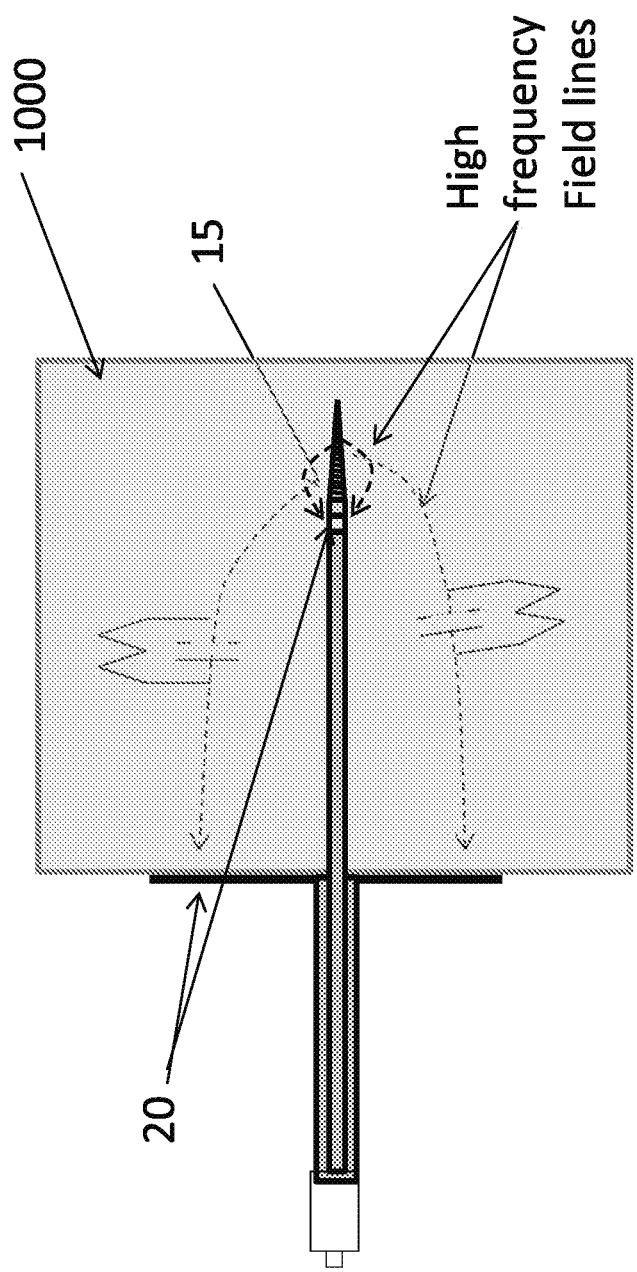
FIG. 16B is a schematic view of the ablation needle electrode of FIG. 16A inserted in tissue in one embodiment of the invention.

FIG. 16 shows an RF/microwave needle antenna electrode in one embodiment of the invention which is a combination of a monopole antenna and a dipole antenna with the ground plane of the dipole antenna placed outside the body. The body of the needle antenna electrode is a triaxial cable. This design has one positive 15 and two ground planes 20, one ground plane in close proximity to the positive and one ground outside the body. In one antenna electrode configuration, the core and the inner shield form a monopole/modified dipole antenna. RF for ablation may be delivered to the tissue by the positive plane/electrode or both the positive and ground plane/electrode. The ablation zone is monitored by reflection measurements between the inner monopole/modified dipole antenna and between the positive and the ground plane outside the body. As indicated by the field lines in FIG. 16B, this antenna configuration has a wider sensitive region and can be used for shallow and deeper anatomical locations. This configuration provides distinct return loss, phase angle profiles in the frequency domain to monitor local tissue changes between the two antenna combinations simultaneously. The outer ground plane can be made in different forms as described earlier for FIG. 15 and need not be fixed to the needle antenna electrode. Since in this configuration there are two antenna on a single device and two reflection measurements are made, these can be made intermittently using one or more reflection measurement setups. An analog or digital switch will enable measurements with the two antenna intermittently.

Figure 17:
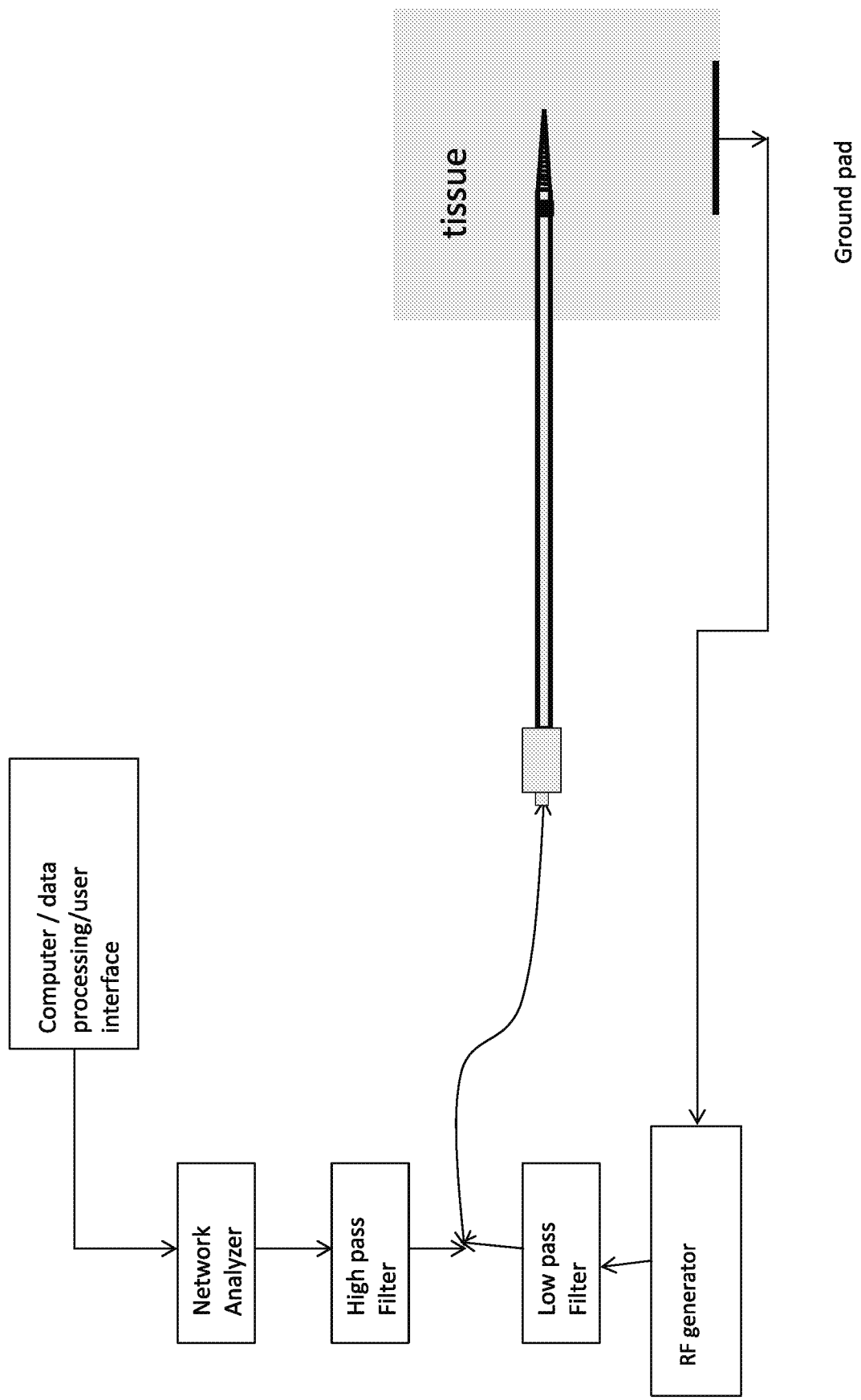
FIG. 17 is an illustration showing the layout of an ablation lesion assessment system of the invention.

FIG. 17 shows a schematic of the setup to monitor RF ablation zone with the needle antenna electrodes described in FIGS. 14-16. This is done by monitoring changes in magnitude and phase of incident and reflection signal, i.e. reflection properties of the needle antenna electrode, i.e. return loss, phase angle in the frequency domain, during the ablation procedure. The ablation RF (500 KHz) generated by the RF generator passes thru a low pass filter to attenuate all non-ablation frequencies, a ground pad placed on the patient completes the ablation circuit. The high pass filter prevents the ablation RF from entering the network analyzer and other measuring electronics, but allows the sensing RF/microwave frequencies to pass from and back to the network analyzer. The network analyzer measures and computes the difference in magnitude and phase of the incident and reflected signal and computes the return loss, phase angle, and the like, in the frequency domain during the procedure and displays the information on the computer/user interface.

The electrical properties of these antenna electrodes is a function of the tissue in which the antenna electrodes are placed and the antenna designs, i.e. number of turns, diameter, pitch, dielectric properties, length of the coil, spacing from the ground plane, and the like. As the tissue properties change during ablation, so do the characteristic resonant frequency/phase reversal frequencies, return loss profile and the phase angle profiles. After the RF ablation antenna electrode is placed in the tissue of interest under imaging guidance, the baseline return loss, phase angle and phase angle reversal frequency data is obtained. During ablation the changes to these characteristic properties is monitored and depth of lesion formed/ablation zone, rate of lesion formation is inferred and monitored. These devices will have limitations on depth assessment to a few mms 5-15 mm diameter based on change in resonant frequency changes. To further assess ablation zone, beyond the sensitivity offered by resonant frequency shift, other methods to estimate ablation zone based on total energy deposited are implemented. Namely, estimating the time duration and amplitude of RF energy (wattage) applied over the surface/volume of the tissue.

As described earlier, efficacy of RF ablation is a function of tissue properties at the electrode-tissue interface. A corresponding safe return loss, phase angle and resonant frequency conditions at which, there is minimal thermal tissue damage, is determined, and the ablation parameters adjusted to hold this state. This method can be used to ensure no excessive thermal damage occurs to the tissue at the electrode-tissue interface, e.g. charring, water boiling, and the like, which is needed in order to create deeper lesions. By titrating the input RF power levels such that an optimum interface tissue characteristics is maintained to create deep lesions. The total energy delivered to the tissue in these controlled conditions is used to estimate the ablation zone, where the ablation zone is proportional to the total energy deposited. However for this method to be effective, it is important to know if there are any blood vessels which will act as heat sinks.

This feature can be incorporated in the user interface depicted herein, where the physician sets the safe level of maximum resonant frequency or the resonant frequency range and time duration of ablation in that range. The controller hardware and software adjusts/titrates the RF input power applied by the RF generator to maintain the resonant frequency range.

The methods described above implement monitoring the reflection (S11) electrical properties of an antenna electrode in the frequency domain to monitor RF ablation procedure and assess lesion formation. One of the limitations of these systems is the limited depth of penetration and can be overcome by performing transmission measurements along with reflection measurements. Reflection measurements will be used to monitor rate of tissue property changes in contact to the RF applicator 10 and the transmission electrical properties will be measured to quantify ablation zone and extent of tissue thermal damage in the volume of tissue being ablated.

Figure 18:
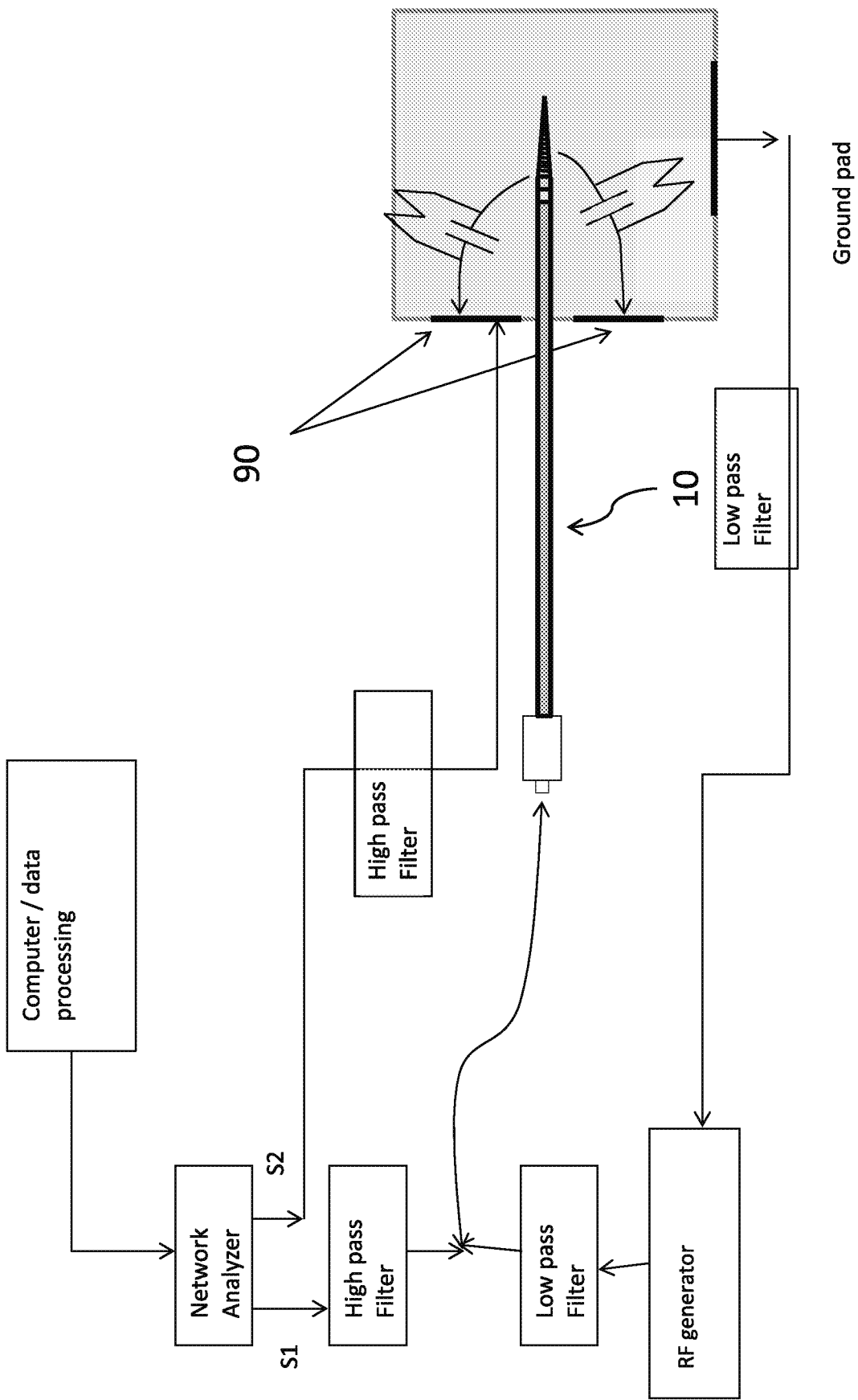
FIG. 18 is an illustration showing the layout of an ablation lesion assessment system of the invention.

FIG. 18 shows the schematic of a system of the invention which performs transmission (S12 and/or S21) and reflection (S11) measurements during RFA procedures to assess ablation zone. The system comprises a needle antenna electrode 10 which is placed in the tissue to be ablated and receiver coils 90 which are placed outside the body, e.g. on the surface of the skin. The needle antenna electrode may be a monopole/modified dipole antenna and transmits an electromagnetic signal in the frequency domain, which travels thru the tissue to the external receiver coils 90. S11 reflection measurement will provide assessment of tissue directly in contact with the electrode and the S12 transmission properties will provide assessment of the tissue thru which the signal travels to quantify ablation zone and extent of thermal injury. The ground pad to complete the ablation RF circuit is a high impedance pad to prevent high frequencies from coupling to it and getting grounded, or it has a low pass filter inline to the RF generator to prevent high frequency signals from being grounded.

Reflection electrical properties, e.g. return loss, phase angle, reflection coefficient, of the needle antenna electrode 10 will be measured in the frequency domain to assess tissue properties in contact with the needle antenna electrode. The transmission electrical properties between the needle antenna electrode and surface receiver coils, namely changes in amplitude and phase of the signal transmitted, before and during ablation are monitored to assess the ablation zone and extent of thermal tissue injury. The reflection and transmission assessment is performed by a vector network analyzer capable of both measurements. Also the transmitted signal can be measured by other equipment, e.g. spectrum analyzer, which will measure the amplitude and phase of the signals received by the surface receiver coils during the ablation procedure.

The receiver coil placed on the surface may be one or more receiver antenna coils, tuned to a broad frequency range. These can be simple loop coils, phased array loop coils, spiral antenna arrays, and the like. The signal received by these coils may be measured individually in intervals or as a combined output. Digital and analog switches enable select the receiver coils to be monitored and the time intervals at which the signals to be processed. In case a spectrum analyzer is used, a separate signal generator with an output in a broad range of frequencies can be used to measure transmission properties to assess lesion formation and confirm ablation of cancerous tissue, and the like.

It is known that different tumors absorb electromagnetic signals at different frequencies, e.g. breast cancer malignant tissue absorbs RF in the range between 180-400 MHz, which may change with antenna design. An electromagnetic signal in this frequency range may be transmitted by the ablation antenna electrode and the magnitude and phase change monitored during the ablation procedure will be used to ensure complete ablation of the tumor and the margin.

The receiver coils placed on the surface of the skin/body need to make good electrical contact with the surface of the skin, so appropriate conductive adhesive will be required. These coils can be various types including loop coils, archimedean spirals, and the like. The coils can be single coils, arrays, phased arrays, and the like designed to receive the high frequency signals transmitted by the ablation antenna electrodes thru the tissue. The output of the receiver coils can be connected to a network analyzer and/or a spectrum analyzer, via a switch where the signal from one or more coils at a time a received and processed.

Figure 19A:
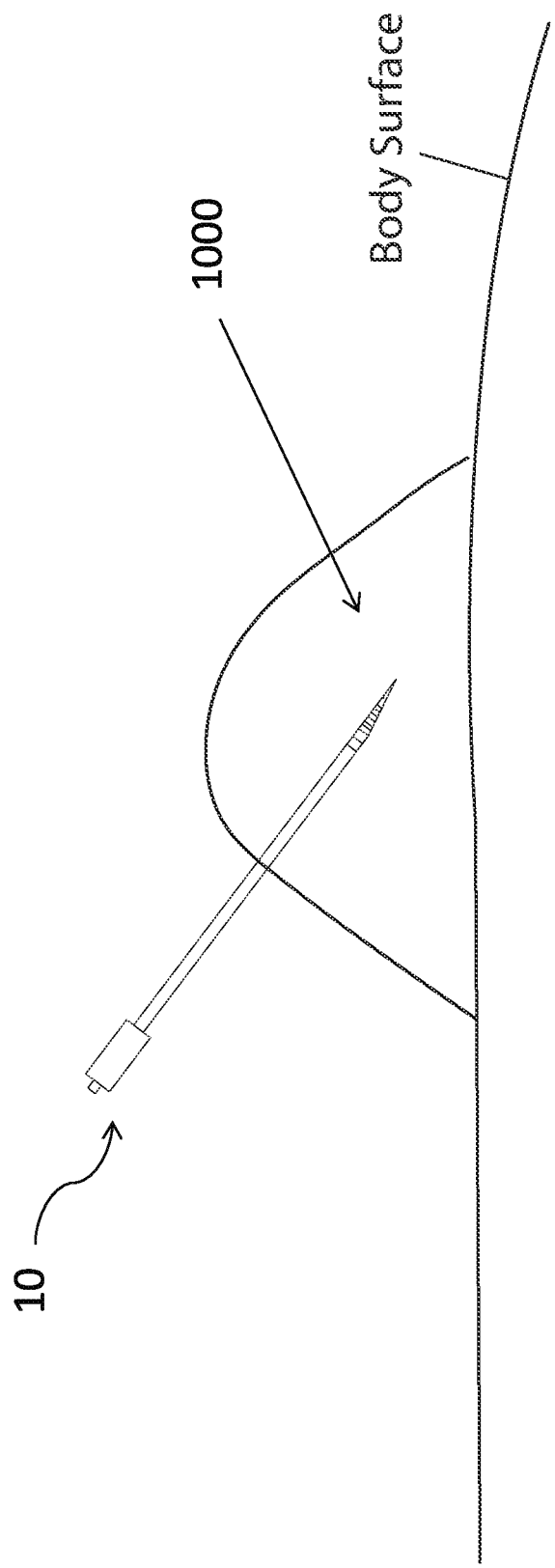
FIG. 19A is a schematic view of an ablation needle electrode in one embodiment of the invention inserted into tissue in an RFA procedure.
Figure 19B:
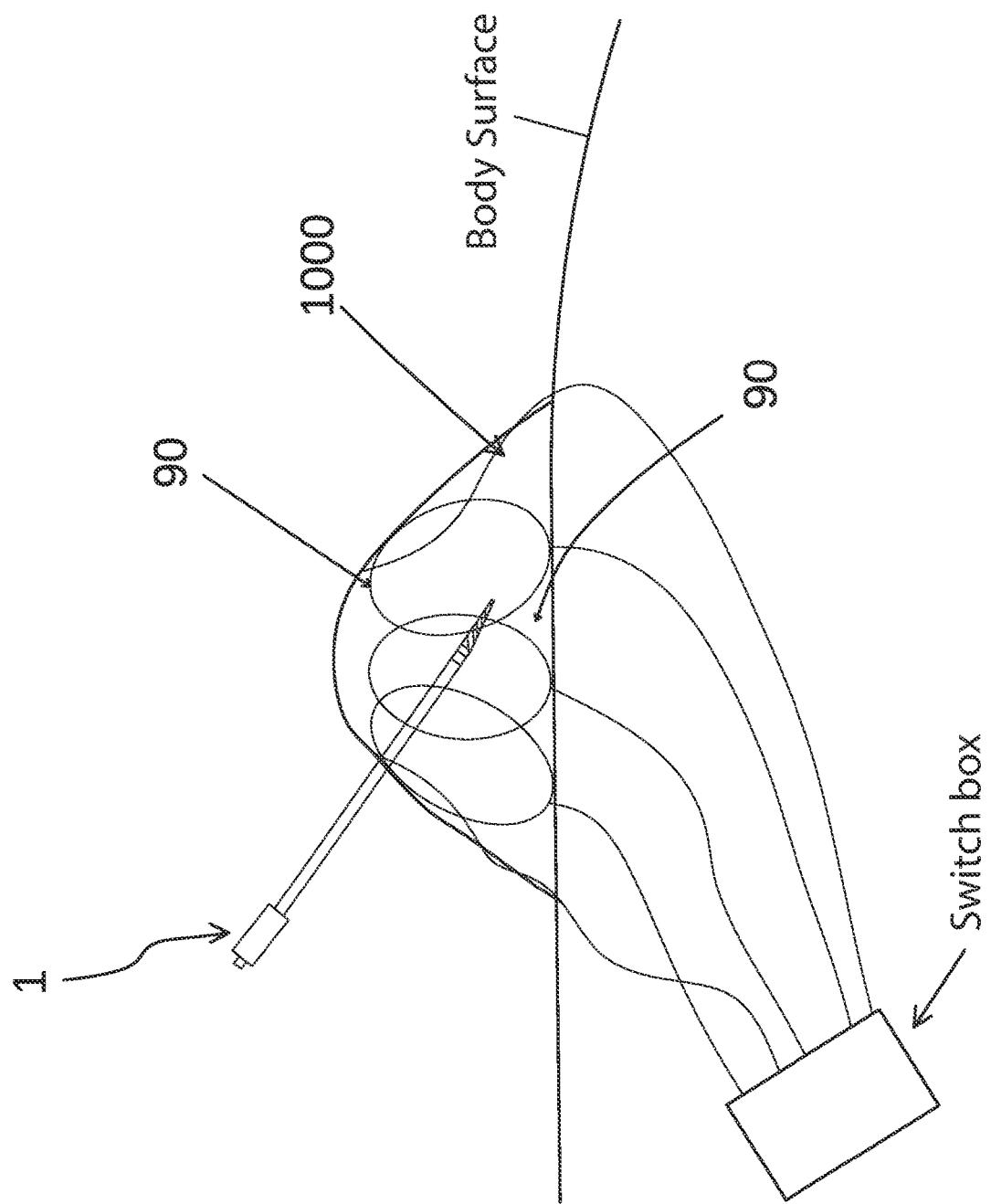
FIG. 19B is a schematic view of an ablation needle electrode in one embodiment of the invention inserted into tissue in an RFA procedure.
Figure 19C:
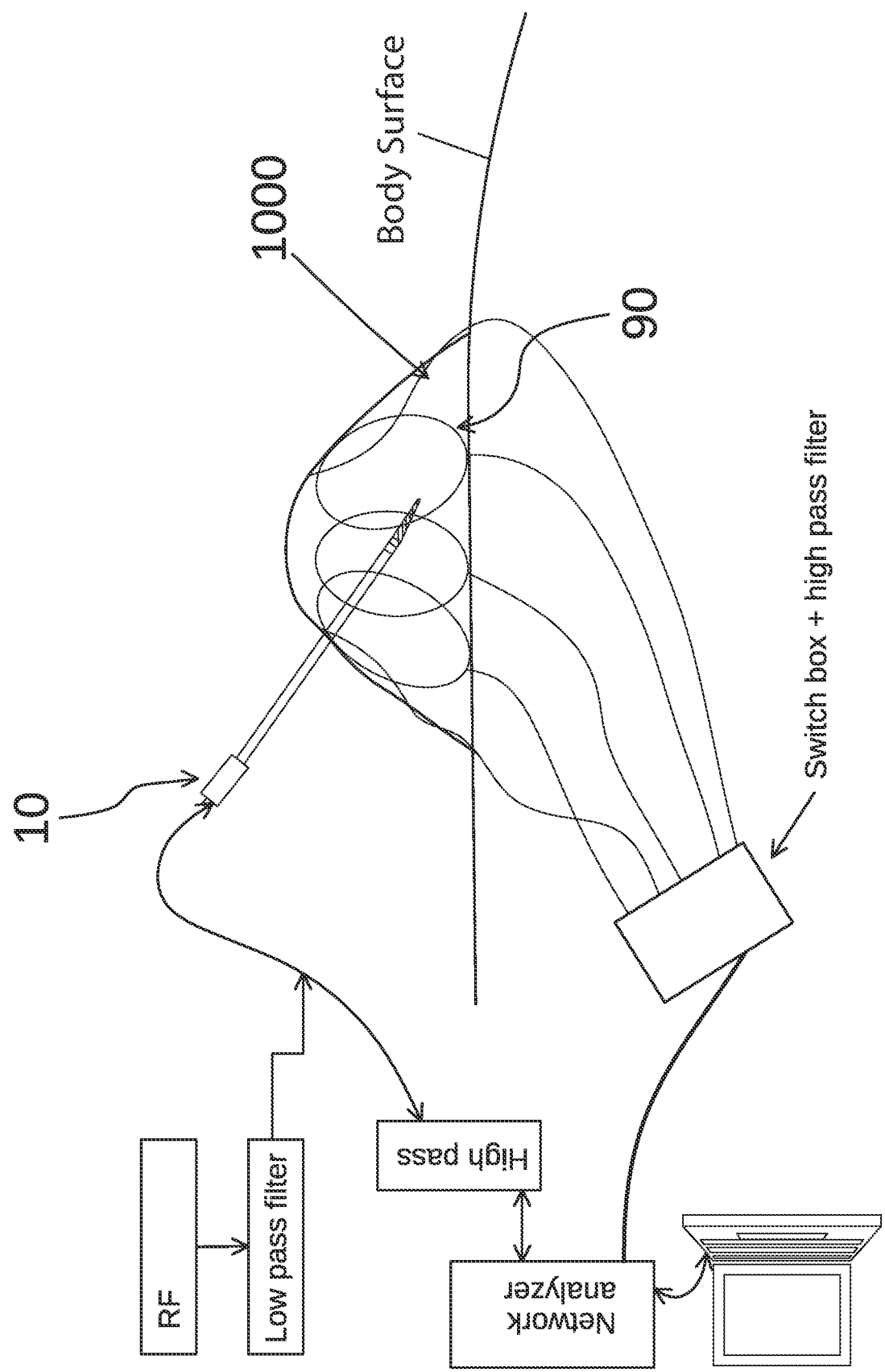
FIG. 19C is a schematic view of an ablation needle electrode in one embodiment of the invention inserted into tissue in an RFA procedure coupled with additional components of the system of the invention.

FIG. 19 shows the schematic of an RF ablation lesion assessment system of the invention implementing reflection and transmission measurement for ablation of anatomies such as breast cancer tumor ablation. During breast cancer tumor ablation procedure, a needle antenna electrode 10 will be placed in the tumor, at a predetermined location, using ultrasound, MRI or guidance modalities (FIG. 19A). The needle antenna electrode will be placed in the tumor such that the entire tumor can be ablated in a single insertion, but may be with retracting the needle to completely ablate the resection zone. The placement of the needle antenna electrode in the anatomy with respect to the tumor is recorded (preoperative or intraoperative images) and ablation zone determined. Presence of heat conducting anatomies such as blood vessels, glands, and the like is noted and recorded. External receiver coils 90, which are phased array coils will be placed around the breast, such that they are in good contact with the skin with minimal air pockets, which will affect signal reception (FIG. 19B). The needle antenna electrode and external coils are connected to the high frequency measurement equipment, e.g. vector network analyzer, spectrum analyzer, and the like via filter hardware (FIG. 19C). Baseline reflection transmission properties with the needle antenna electrode and surface receiver coils is obtained and recorded, which may include return loss, insertion loss, magnitude and phase measured in the frequency domain. The amplitude of the sensing signal for reflection and transmission is typically less than 1 W. After the baseline properties are obtained, RF ablation is turned on and the power level is adjusted such that the resonant frequency of the needle antenna electrode as measured by reflection properties is maintained in the safe mode not to cause excessive temperature rise in the vicinity of the needle electrode, thus maximize the ablation zone. The transmission electrical properties i.e. magnitude and phase of transmitted signal from the needle antenna electrode to the external receiver coils is recorded in the frequency domain during the ablation procedure. Preoperative ablation experiments will guide the ablation lesion/zone determination based on the shift in maximum insertion loss frequency and maximum return loss frequencies. In addition to the frequency sweep assessment, insertion loss in a narrow frequency range may be measured since the breast cancer tumors and other tumors absorb EM radiation in a frequency range of 100-500 MHz (this frequency may change depending on antenna design). Change in insertion loss of these frequencies may imply complete tumor ablation. Similar methods may be used to other ablations, e.g. nerve ablation for pain management, liver tumor ablation, and the like.

Figure 20:
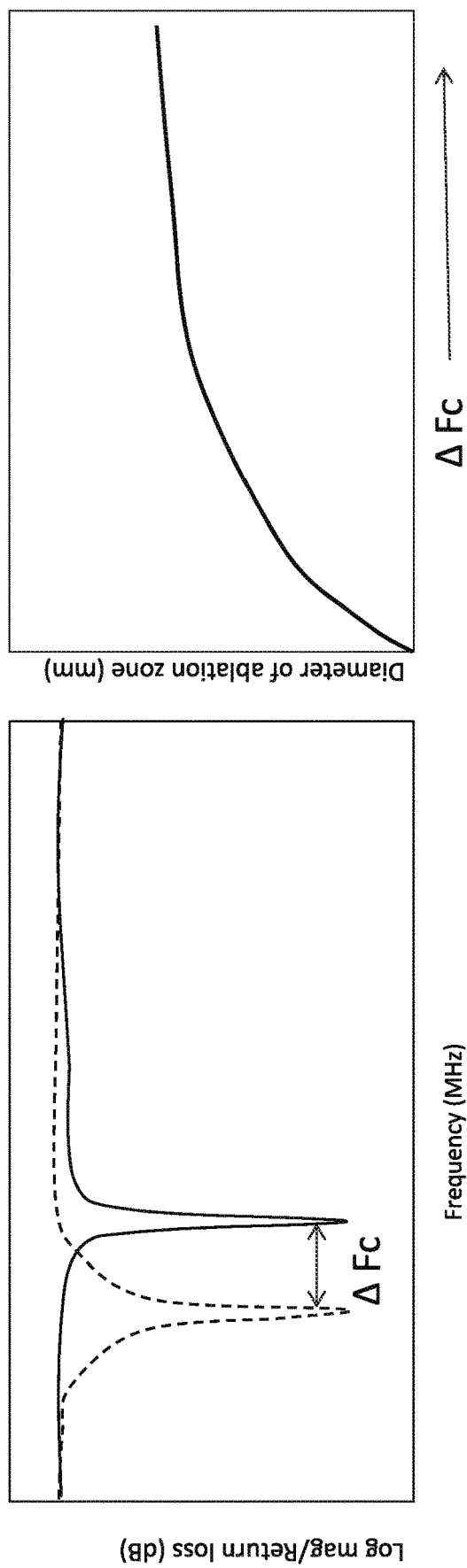
FIG. 20 is a set of graphs depicting data generated using the system of the invention.

FIG. 20 shows the characteristic amplitude profile of the insertion loss between the signal transmitted by the needle antenna electrode 10 and received by the receiver surface coils 90 in the frequency range. By monitoring the frequency/frequencies of maximum insertion loss and phase of the signal at the maximum loss frequency/frequencies; the ablation zone and extent of thermal injury is quantified. Return loss/log magnitude v/s frequency indicating coupling between the ablation needle antenna electrode 10 and the sensing antenna 90 on the surface. The differential in the coupling frequency from onset of ablation is used to determine ablation zone diameters.

Figure 21:
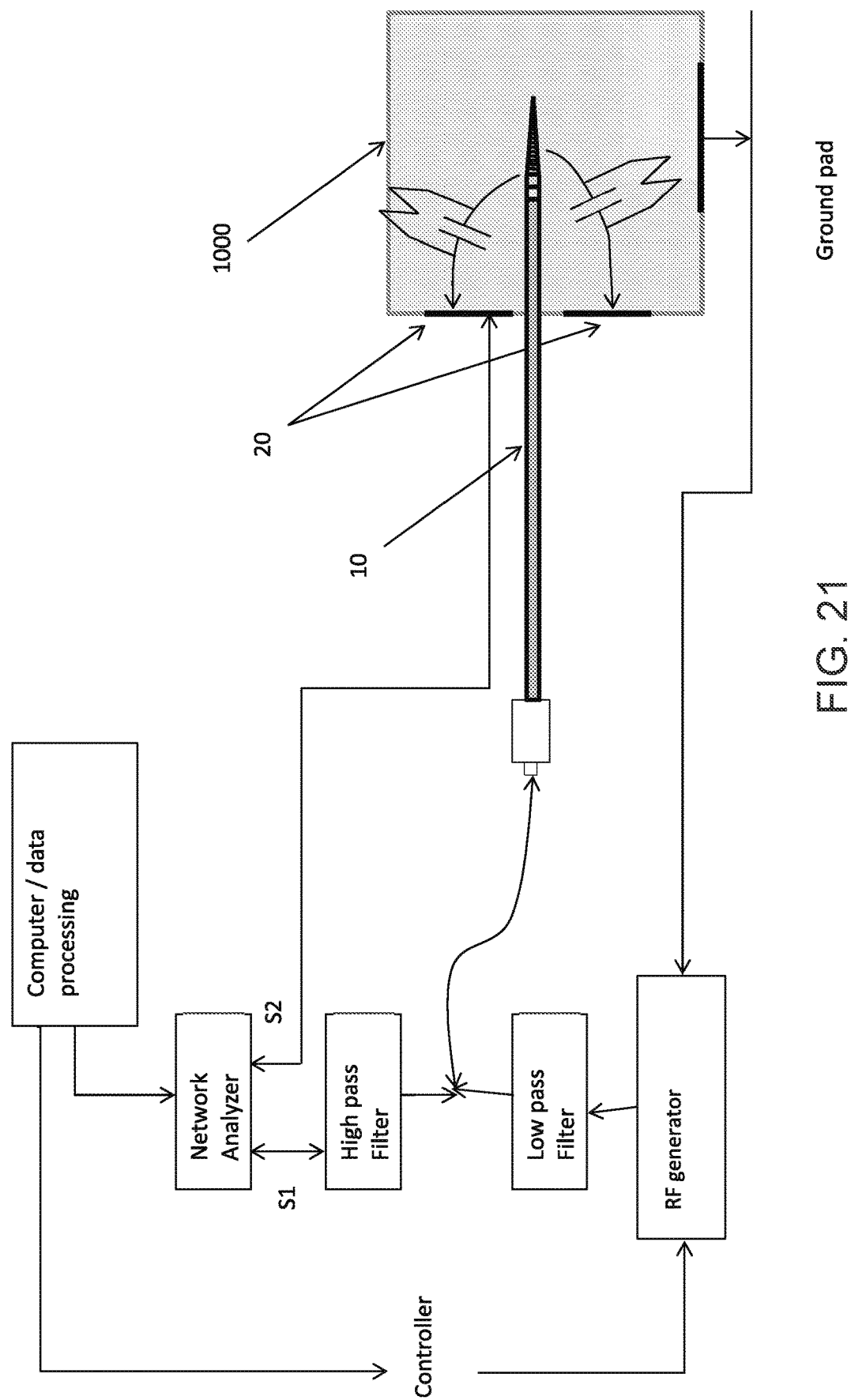
FIG. 21 is an illustration showing the layout of an ablation lesion assessment system of the invention.

FIG. 21 shows a system setup in one embodiment of the invention which can be implemented to create, monitor and maximize ablation lesions by controlling RF power applied during ablation. The system utilizes monitoring S11 reflection resonant frequency to continue ablating at a safe level and monitoring S12 transmission for assessing ablation zone and extent of tissue damage. The physician sets the safe level of ablation, i.e. the maximum resonant frequency or the resonant frequency range in which to maintain the ablation power input and time duration of ablation. The controller hardware and software adjusts/titrates the RF input power applied by the RF generator to maintain the resonant frequency range.

During clinical use the operator will place the needle antenna electrode device 10 in the anatomical region of interest guided by intraoperative or preoperative MRI, CT, X-ray or ultrasound imaging. Upon placing the needle antenna electrode 10 in the desired anatomical target, the needle antenna electrode 10 is connected to the interface circuit comprising RF filters, i.e. low pass and high pass filters, which are in turn connected to the RF ablation generator, network analyzer (or signal generator and amplifier). The surface receiver coils 90 are carefully placed on the surface of the skin making sure they are in good contact and there are minimal air gaps between the body and the receiver antenna 90, and connected to the network analyzer (or spectrum analyzer). A grounding pad is placed in a region away from the ablation zone to complete the RF ablation circuit pathway and connected to the RF generator via a low pass filter.

Upon completing the setup, the baseline reflection transmission measurements are performed and data is recorded. The safe ablation window in terms of resonant frequency range is set by the operator in the manual mode or auto control mode, and RF energy is applied. The input RF power levels are regulated/titrated by monitoring the S11 reflection properties of return loss, phase angle and resonant frequency. The ablation zone is assessed by the reflection properties as well as transmission properties (i.e. frequency and phase of maximum insertion loss), and the ablation is stopped after desired ablation target is achieved or a steady state of reflection transmission properties is reached, i.e. ablation zone has reached a steady state.

FIG. 22 sets forth different configurations of antenna designs that can be incorporated for needle antenna electrode configurations shown in FIGS. 14-21 in various embodiments of the invention.

FIG. 22A illustrates a loopless/monopole antenna with a straight positive section.

FIG. 22B illustrates loopless/monopole antenna with a backward coiled helical positive section.

FIG. 22C illustrates loopless/monopole antenna with a forward coiled helical positive.

FIG. 22D illustrates a dipole with positive and ground plane co-wound.

FIG. 22E illustrates a solenoid antenna with a helical coil connecting positive and the ground.

All the antennas from FIGS. 22A-E can be designed with a balun circuit on the shield as shown in FIG. 22F, which creates a high impedance and prevents the current leaking on to the shield; only the section of the shield distal to the balloon acts as the ground plane.

FIGS. 22G and H illustrate embodiments of the invention which include a slotted shield antenna and modification for an ablation antenna-electrode. The needle antenna electrode may be configured as a slotted shield antenna, with one or more slots 250 along the length of the ablation section of the electrode including coax cable 600. The shield extends to the distal end of the antenna electrode, and some sections of the shield are not insulated to allow for electrical contact with tissue. A coil 280 may be connected to the core of the coax thru the slots in the shield and the coil 280 wrapped around the shield with a dielectric between the coil and the shield. Coil 280 is attached to the core thru the slotted shield with no insulation being on coil 280 which acts as the positive of the antenna electrode. There is a dielectric under the coil over the shield to prevent direct electrical contact. Ablation RF is applied to both the core and the shield. With this design, the sensitive section of the antenna is in the middle of the ablation zone, and provide better assessment of the extent of ablation zone.

Different configurations of the cardiac RF ablation catheter antenna electrode of the invention are described below. Since the ablation antenna electrode has positive and ground planes of the antennae incorporated on the surface of the electrode in close proximity, the base of the antenna electrode is constructed out of dielectric materials. These can be polymeric materials, such as but in no way limited to polyether ether ketone (PEEK), polyimide, ceramic materials, such as alumina, aluminum nitride, and the like. These materials have poor electrical conductivity (very high electrical resistivity) and low dielectric constant (dielectric constant <20), to impart electric and magnetic field penetration in the medium surrounding the antennae. During the ablation procedure, as tissue in contact with the electrode heats, this thermal energy is conducted to the electrode as well, causing the electrode to heat. Electrode temperatures over 43° C. can cause blood coagulation on the surface of the electrode causing high impedance to RF current, preventing tissue ablation. To avoid blood coagulation on the electrode, the electrode needs to be cooled during RF ablation. This is achieved by closed loop saline irrigation or open flush saline irrigation. Open flush saline irrigation is preferred due to its relatively better temperature control due to constant saline flow, which also maintains the tissue surrounding the electrode cool, thus potentially increasing lesion depth.

Figure 23A:
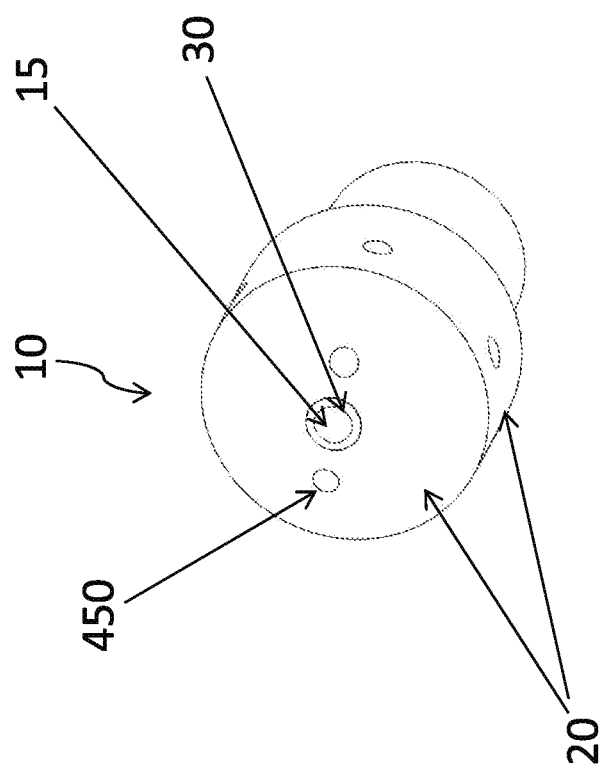
FIG. 23A is a schematic view of an antenna electrode in one embodiment of the invention.
Figure 23C:
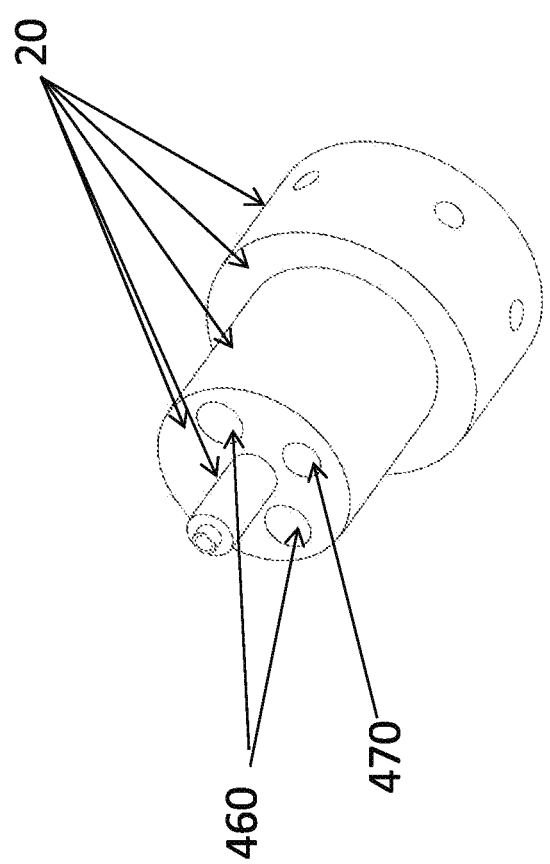
FIG. 23C is a schematic view of the antenna electrode of FIG. 23A.
Figure 23D:
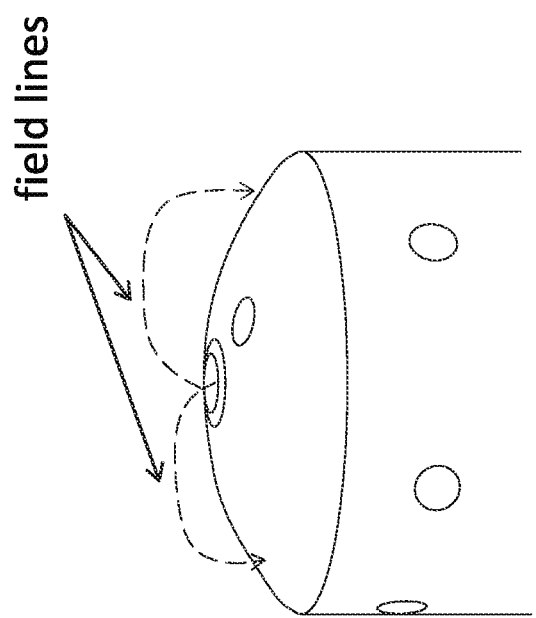
FIG. 23D is an expanded view of the tip of the antenna electrode of FIG. 23A.

FIG. 23 shows a configuration in one embodiment of the invention of a modified coaxial antenna electrode. The positive of the antenna electrode 15 is in the center of the distal surface of the electrode and is about 2-50% of the electrode surface area. The positive 15 is separated from the remaining electrode surface by dielectric 30 where the rest of the surface area of the electrode acts as the ground plane of the electrode 20. The distal hemispherical surface of the antenna electrode is the sensitive region of the electrode is as shown by the field lines in FIG. 23D. The outer surface on the whole, or in part, may be coated with a metallic conductive layer and will function as the ground plane 20 of the antenna electrode 10. This coaxial antenna electrode is sensitive only on the distal surface of the electrode and lacks sensitivity on the sides primarily due to the presence of the ground plane and the field lines from the positive will couple only to the ground plane on the hemispherical side. The ablation RF for the coaxial antenna electrode for this embodiment is delivered to the tissue from the ground plane of the antenna electrode, so the low pass filter circuit will be connected to the shield side of the cable, as opposed to the core.

Figure 24A:
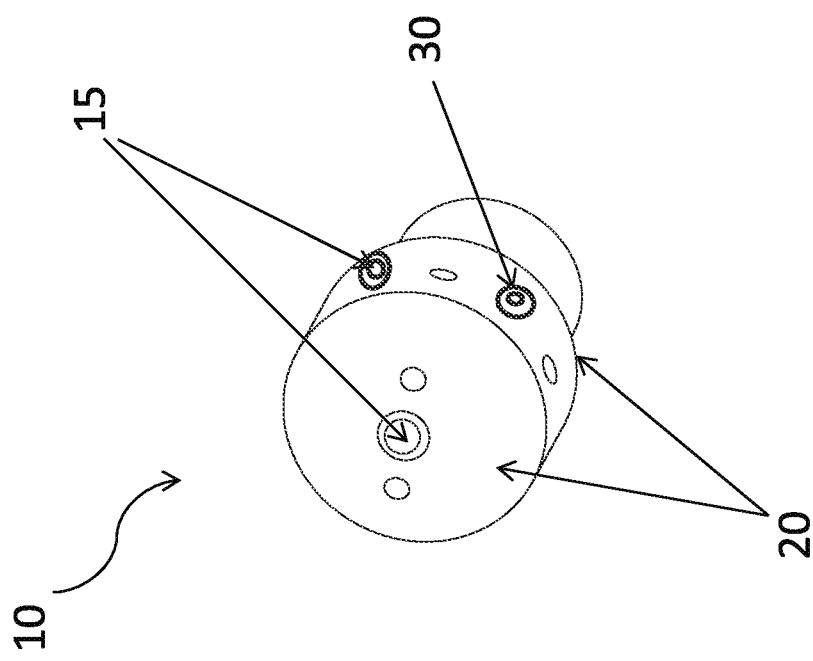
FIG. 24A is a schematic view of an antenna electrode in one embodiment of the invention.
Figure 24B:
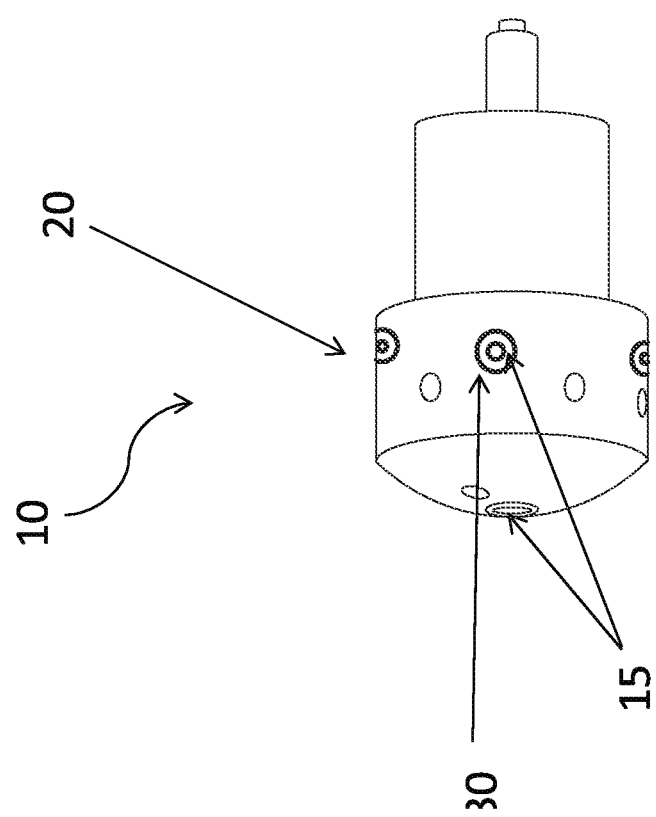
FIG. 24B is a schematic view of the antenna electrode of FIG. 23A.

FIG. 24 shows a coaxial antenna electrode of the invention with sensitivity on the sides. The positive of the antenna 15 has nodes on the side of the cylindrical side of the electrode to provide sensitivity to the distal spherical surface and the cylindrical side surface (similar to the slotted shield antenna embodiment). One of more positive nodes 15 can be located on the sides separated from rest of the ground plane 20 by a dielectric section 30. This imparts sensitivity to the sides of the electrode so that RF ablation can be monitored from all sides of the electrode. The five positive nodes, for reflection properties measurement may be connected to a single coaxial cable or each to an individual coaxial cable with a common ground plane, or each to a cable with five cores and a common ground shield. The output of each node may be monitored simultaneously or intermittently. For intermittent measurement, each node may be routed via a digital/analog switch to facilitate measurement and recording the reflection S11 properties in the frequency domain.

FIG. 25 shows a coaxial antenna electrode of the invention with a spiral on the ground plane on the hemispherical surface. The positive plane 15 is separated by a dielectric 30 from the ground plane 20. The ground plane is configured as a spiral 50.

One of the limitations of the coaxial sensor with one node or multiples nodes as described in FIGS. 23 and 24 is that the return loss profile will be fairly flat in the frequency domain and there is not a distinct resonant frequency/phase reversal frequency to track during the ablation procedure, affecting the sensitivity and specificity of measurements. In order to create a distinct resonant frequency the coaxial sensors described in FIGS. 23 and 24 can be configured with a spiral structure 50 in the ground plane 20 adjacent to the positive nodes 15 as shown in FIG. 25. The spirals 50 in the ground plane 20 are connected to the ground plane 20 from the outside of the spiral and the inner end of the spiral is left open. This adds inductance to the electrode ground plane, thus creating a resonance frequency which can be monitored and tracked during the procedure. For the coaxial antenna electrode designs the ablation RF is delivered from the ground plane of the electrode, but the sensing RF is transmitted from the core or the positive of the antenna electrode.

Figure 26A:
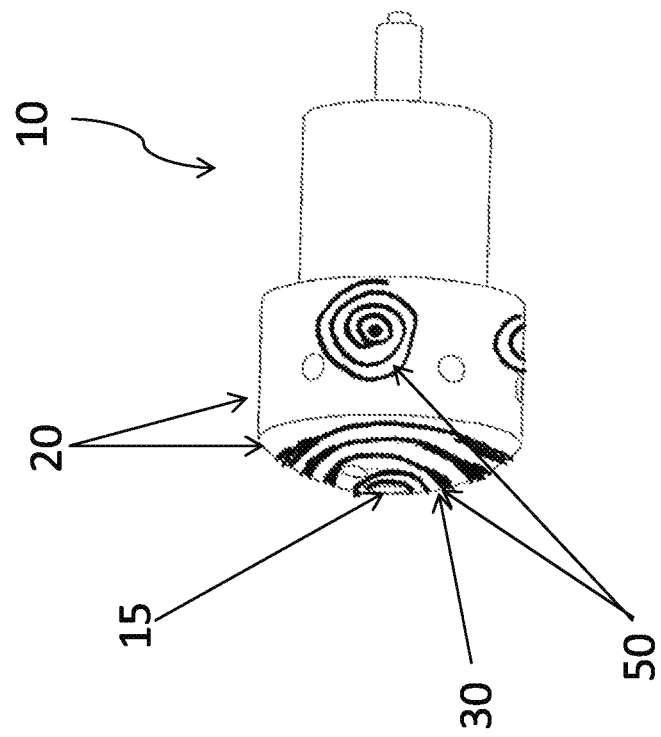
FIG. 26A is a schematic view of an antenna electrode in one embodiment of the invention.
Figure 26B:
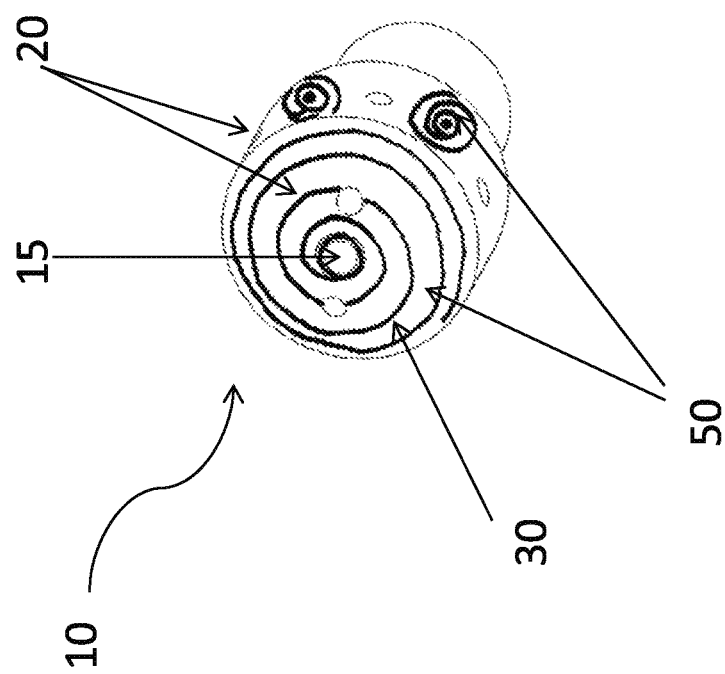
FIG. 26B is a schematic view of the antenna electrode of FIG. 26A.
Figure 27A:
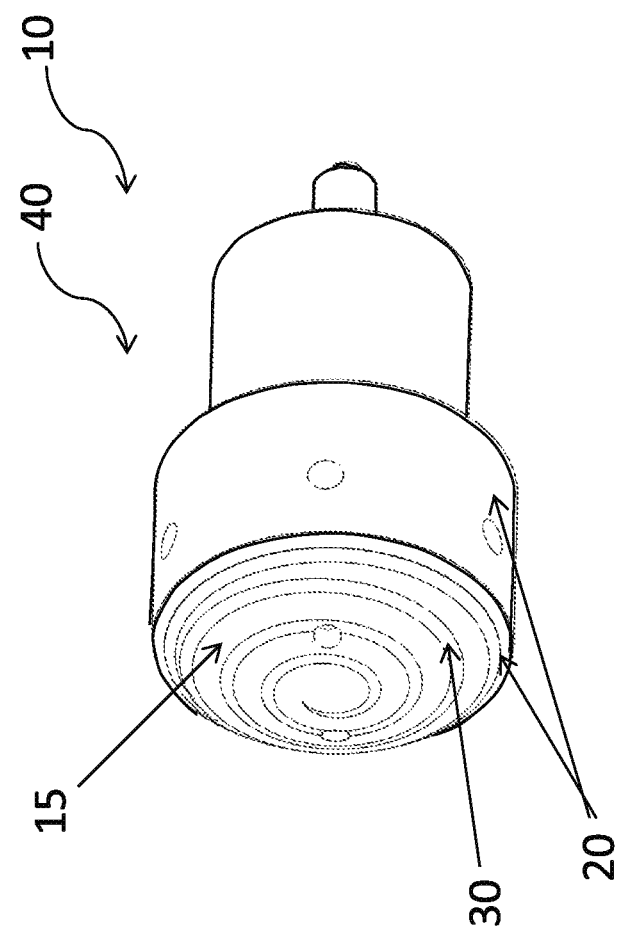
FIG. 27A is a schematic view of an antenna electrode in one embodiment of the invention.
Figure 27B:
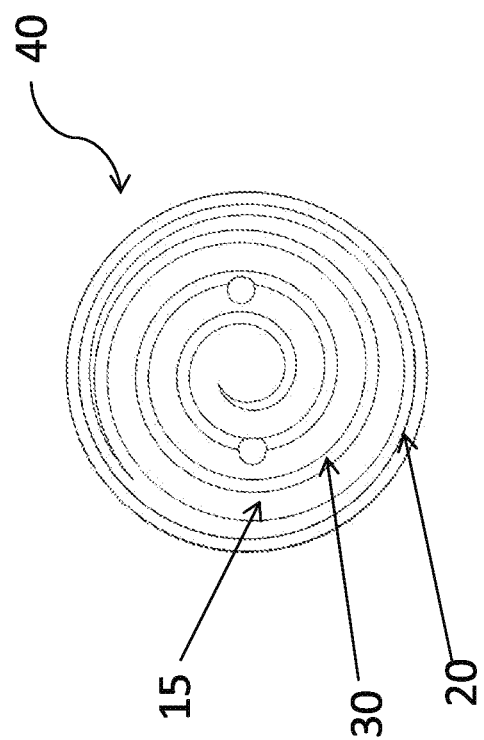
FIG. 27B is a schematic view of the antenna electrode of FIG. 27A.
Figure 27C:
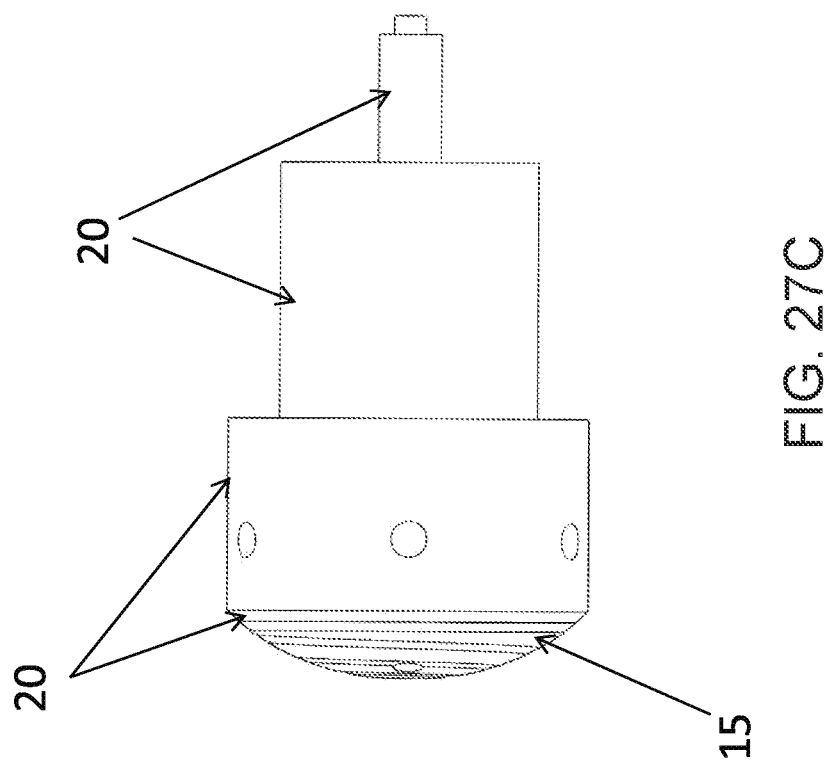
FIG. 27C is a schematic view of the antenna electrode of FIG. 27A.
Figure 27D:
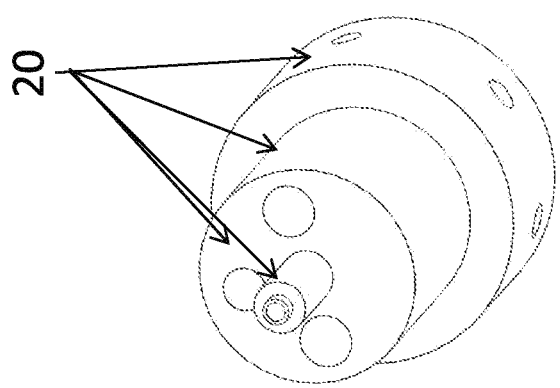
FIG. 27D is a schematic view of the antenna electrode of FIG. 27A.
Figure 27E:
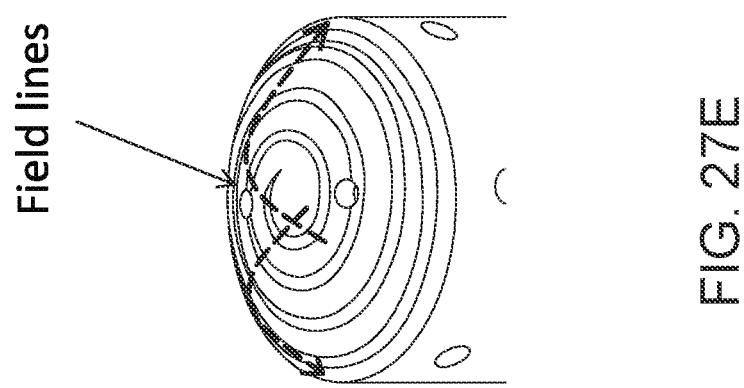
FIG. 27E is an expanded view of the tip of the antenna electrode of FIG. 27A.

FIG. 26 shows the coaxial antenna electrode of the invention with positive nodes 15 on the cylindrical side of the electrode, with the ground plane 20 configured as a spiral ground plane 50 around the positive node 15. This configuration imparts sensitivity to the sides of the electrode and a characteristic resonant frequency to monitor during ablation procedure. The positive nodes may be connected to one or more individual conductors in a single common ground cable configuration. The spirals on each side may have different number of turns, spacing and strut thickness to provide different electrical characteristics, to enable identify electrode-tissue contact orientation.

FIG. 27 shows an antenna electrode configuration of the invention, where the positive of the antenna electrode 15 on the hemispherical surface is configured as a spiral-helix where the positive 15 of the antenna is a helix-spiral 40, each turn is separated by a dielectric 15 and the entire helix-spiral is surrounded by the ground plane 20 on the distal hemispherical surface of the electrode. This creates field lines as shown in FIG. 27E and potentially increases field penetration in the tissue. The ground plane extends on all the sides of the antenna electrode assembly and continues to the proximal end for connecting to the coaxial cable. The spirals in the positive plane 40 can be configured in one or more layers, each spiral layer is separated by a dielectric layer and can be arranged one over the other wound in same or opposite directions to increase the penetration or sensitivity of the antenna electrode.

Figure 28B:
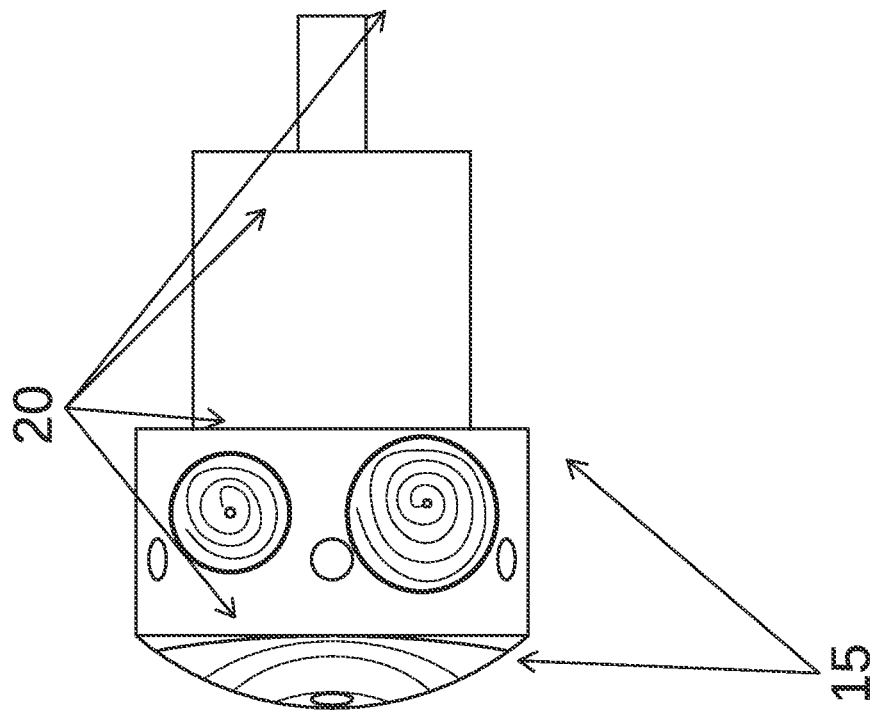
FIG. 28B is a schematic view of the antenna electrode of FIG. 28A.
Figure 28A:
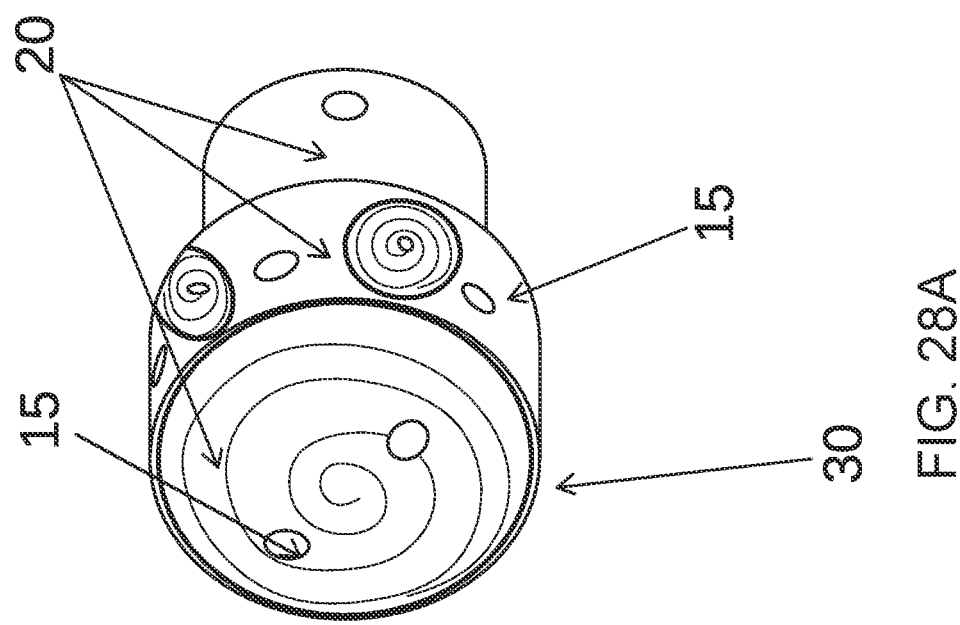
FIG. 28A is a schematic view of an antenna electrode in one embodiment of the invention.

FIG. 28 shows a spiral helix antenna electrode of the invention with one or more positive nodes 15 on the sides of the electrode as well as on the hemispherical surface, where the positive 15 of the antenna is arranged as a spiral-helix 40 on the sides of the cylinder and the hemispherical side. This antenna electrode design imparts sensitivity to distal hemispherical surface as well as to the sides of the electrode. Ablation RF may be delivered to the tissue by the positive plane 15 or the ground plane 20 or both the positive plane 15 and the ground plane 20. The low pass filter will be configured to attenuate non-ablating frequencies on the core and the shield accordingly. Spiral antenna electrode with multiple positive nodes on the side; with spiral on the core/positive on the sides. Each positive node may be connected to the same coaxial cable core (positive) or to different coaxial cables, or to a single shielded cable with multiple cores or a multilayer cable (triaxial cable, quadaxial cable, and the like).

Figure 29C:
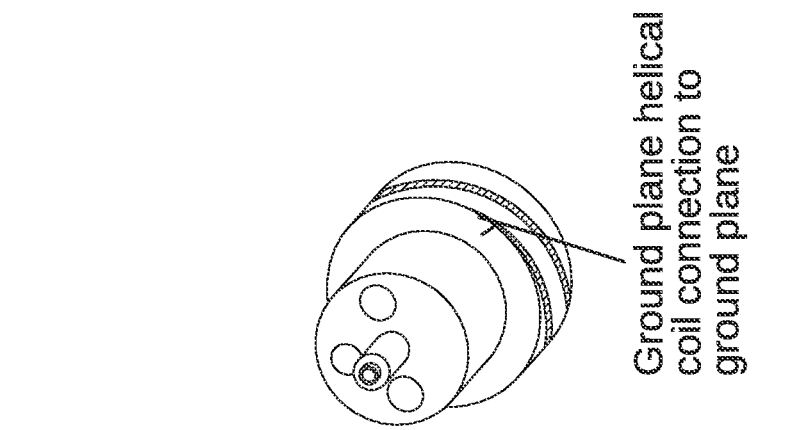
FIG. 29C is a schematic view of the antenna electrode of FIG. 29A.
Figure 29B:
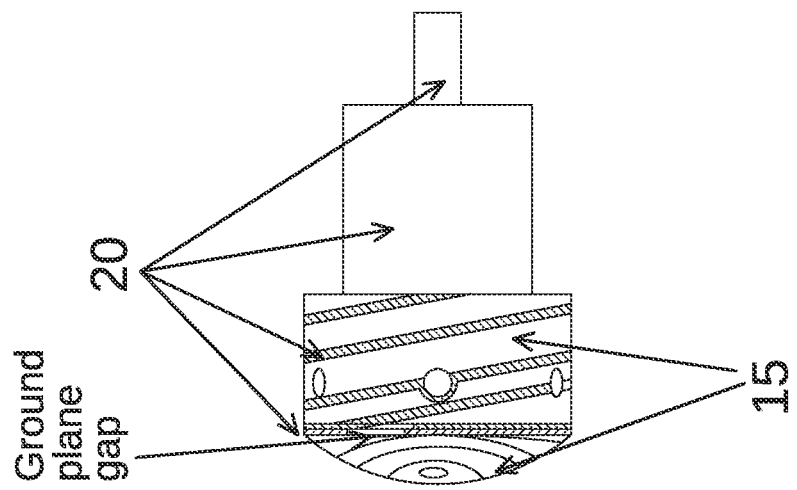
FIG. 29B is a schematic view of the antenna electrode of FIG. 29A.
Figure 29A:
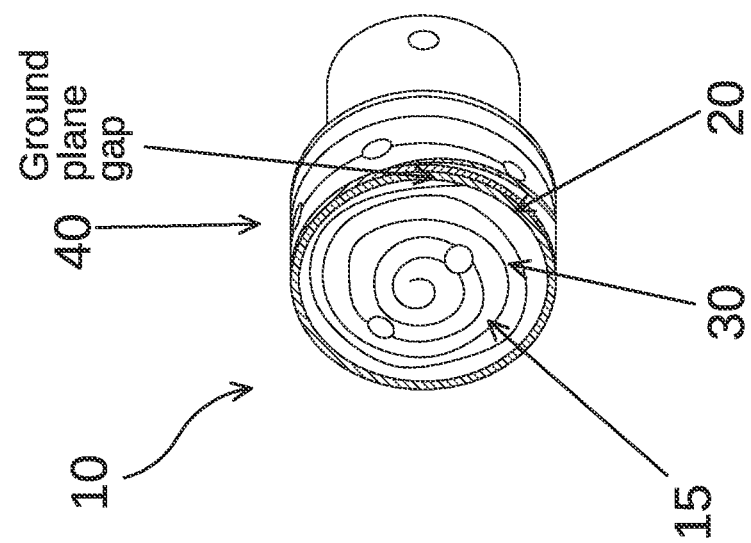
FIG. 29A is a schematic view of an antenna electrode in one embodiment of the invention.

FIG. 29 shows an embodiment of the invention in which the antenna electrode has the positive of the antenna 15 configured as a spiral-helix 40 and the positive of the antenna 15 on the distal hemispherical surface is a helical-spiral surrounded by a ground plane 20 with a gap in the circumference. The positive helical spiral 40 continues out of the hemispherical surface in this gap in the ground plane and continues as a helix on the sides of the electrode where the positive 15 is co-wound helically with the ground plane 20. This structure provides sensitivity to the entire electrode including the sides. This antenna structure attributes distinct electrical properties due to the helical spiral on the distal hemispherical surface and helical coil antenna structure by the co-wound positive plane and the ground plane spirals on the sides; this enables to characterize orientation of the antenna electrode as it is in contact with the tissue and assess lesion formation.

Figure 30B:
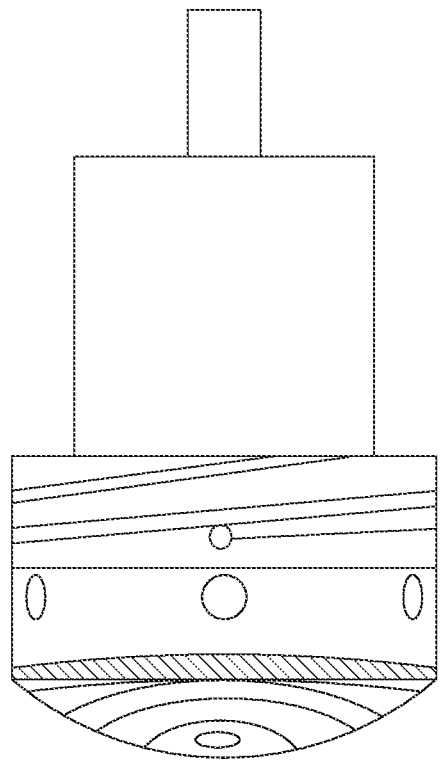
FIG. 30B is a schematic view of the antenna electrode of FIG. 30A.
Figure 30A:
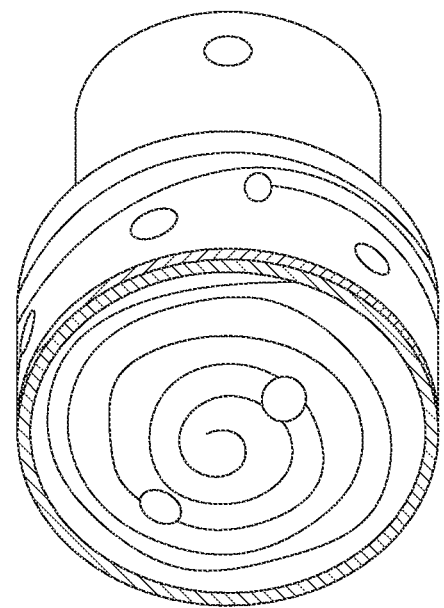
FIG. 30A is a schematic view of an antenna electrode in one embodiment of the invention.

FIG. 30 shows a spiral helical antenna of the invention with two antennae structures; one connected to the distal hemispherical spiral helical antenna and the other connected to the helical coil dipole antenna on the side of the electrode. Both antennae may have one common ground or separate ground planes. Each antennae may be connected by one or more coaxial cables or triaxial cable. On the distal hemispherical surface positive of the antenna 15 coiled in a spiral surrounded by the ground plane ring 20. On the sides of the electrode, a positive node 15 is connected to the core of the coaxial cable (as the positive plane 15 on the distal hemispherical surface) and is coiled in a helix to form a helical antenna. A common ground plane 20 is on the circumference of the distal hemispherical surface and the circular side edge of the cylindrical side of the electrode. On the cylindrical side, the ground plane is under the helical positive plane and the two are separated by an insulator/dielectric layer. This antenna electrode structure is sensitive on the sides of the electrode and on the distal hemispherical surface.

Figure 31A:
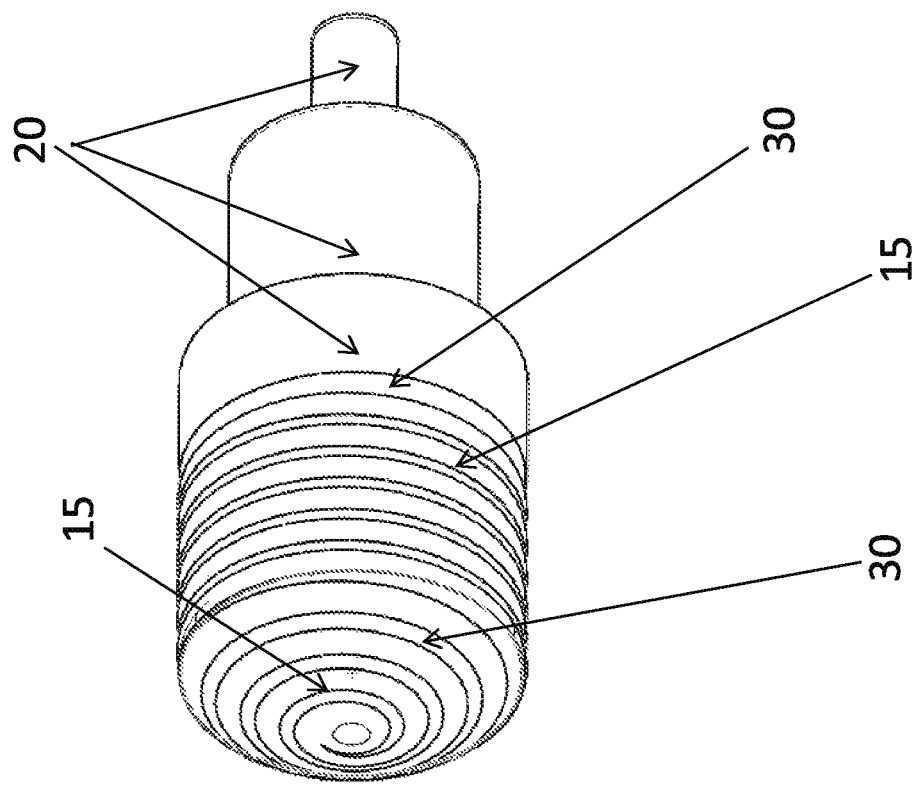
FIG. 31A is a schematic view of an antenna electrode in one embodiment of the invention.
Figure 31B:
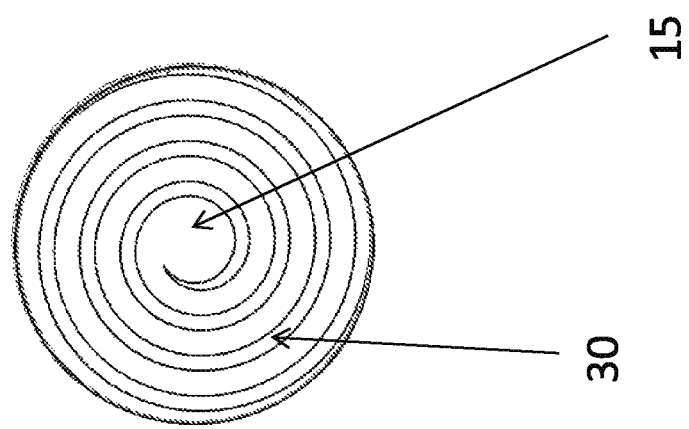
FIG. 31B is a schematic view of the antenna electrode of FIG. 31A.
Figure 31C:
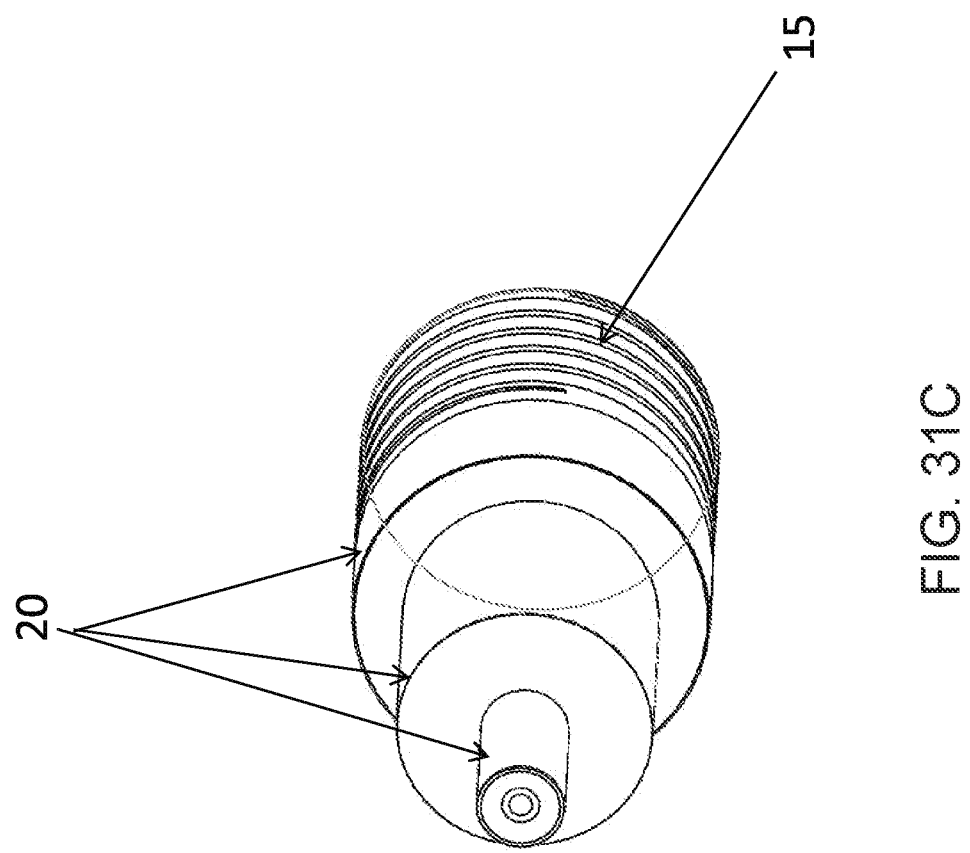
FIG. 31C is a schematic view of the antenna electrode of FIG. 31A.

FIG. 31 provides yet another embodiment of the antenna electrode design in which the positive 15 is configured as a spiral helix which starts on the distal hemispherical surface, then continues on the side for some distance. Separated by a dielectric 30 is a circular ground plane 20. A similar design where the positive spiral helix starts on the sides and ends on the hemispherical surface can be implemented. This antenna electrode has sensitivity on the distal hemispherical surface and the sides of the electrode. The pitch, turns and width of the spiral struts and gaps in the spiral struts can be configured to provide a fairly isotropic sensitivity region. This design could be modified by co-winding the ground plane with the positive helical coil on the sides of the electrode in a preferred embodiment.

In another configuration of the spiral helix embodiment, the positive and the ground of the antenna are co-wound in an Archimedean spiral helical coil configuration on the hemispherical surface and the sides of the electrode. The positive of the antenna 15 and the ground of the antenna 20 are co-wound in a spiral in the hemispherical section of the electrode and then as a co-wound helix on the sides of the antenna. Alternate designs would include, one where both the ground and the positive/core are connected to the coaxial cable at the distal tip; or the core is connected at the distal surface and the ground is connected to the shield at the proximal end.

Figure 32B:
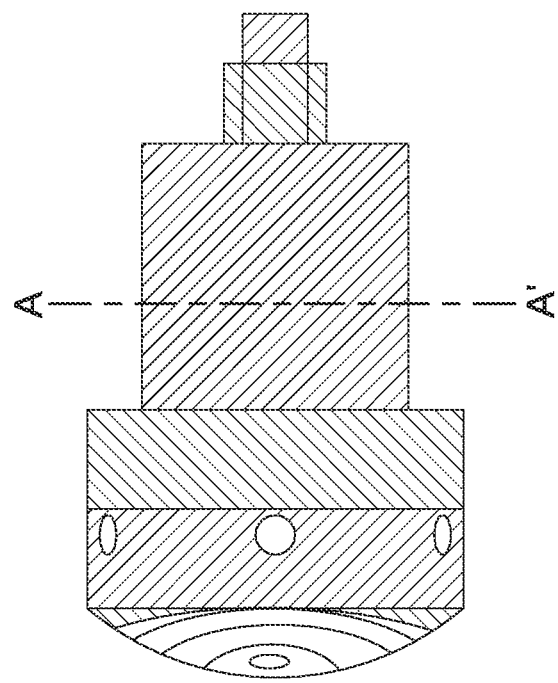
FIG. 32B is a schematic view of the antenna electrode of FIG. 32A.
Figure 32A:
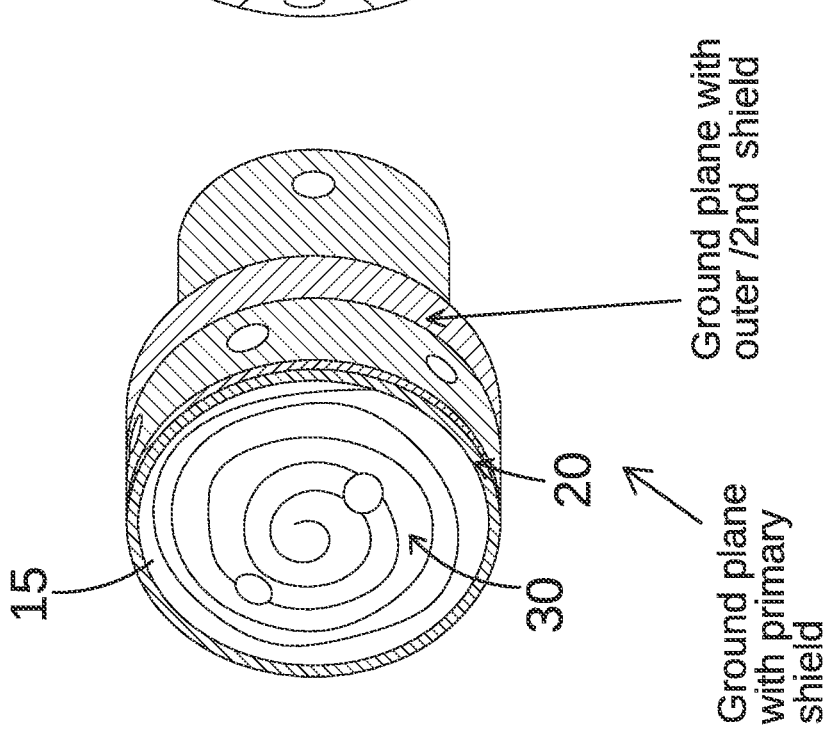
FIG. 32A is a schematic view of an antenna electrode in one embodiment of the invention.
Figure 32C:
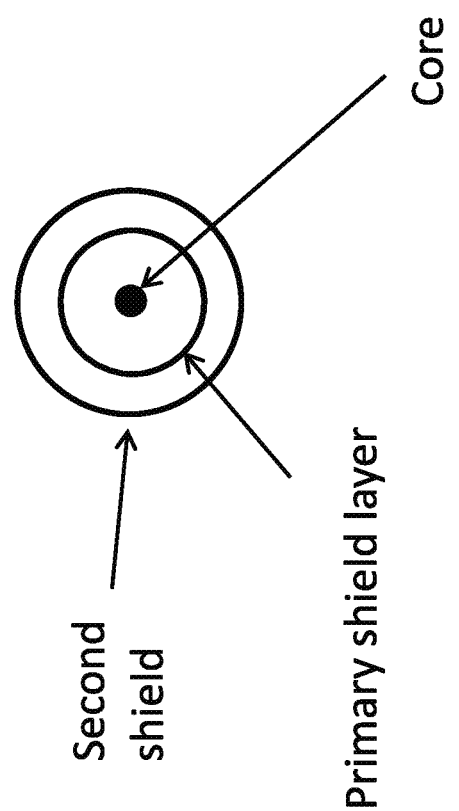
FIG. 32C is a cross-sectional view of the antenna electrode of FIG. 31A along line A-A'.

FIG. 32 shows an electrode of the invention which is configured in a triaxial design with the inner core and the first/primary shield layer being incorporated in the electrode forming one antenna, and the primary/first shield and the second shield forming the other antenna. Each antenna can have the positive or the ground/shield in a coiled, singular meandering configuration.

Figure 33B:
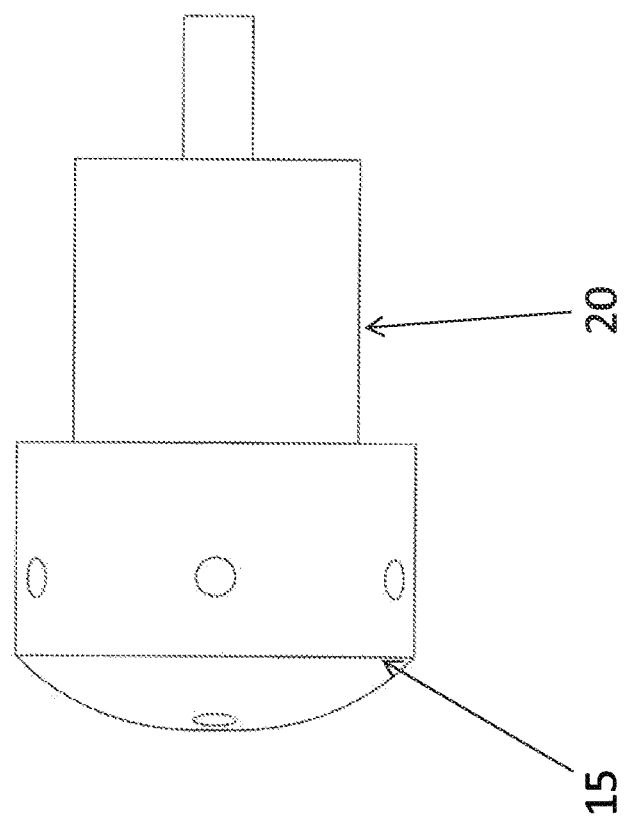
FIG. 33B is a schematic view of the antenna electrode of FIG. 33A.
Figure 33A:
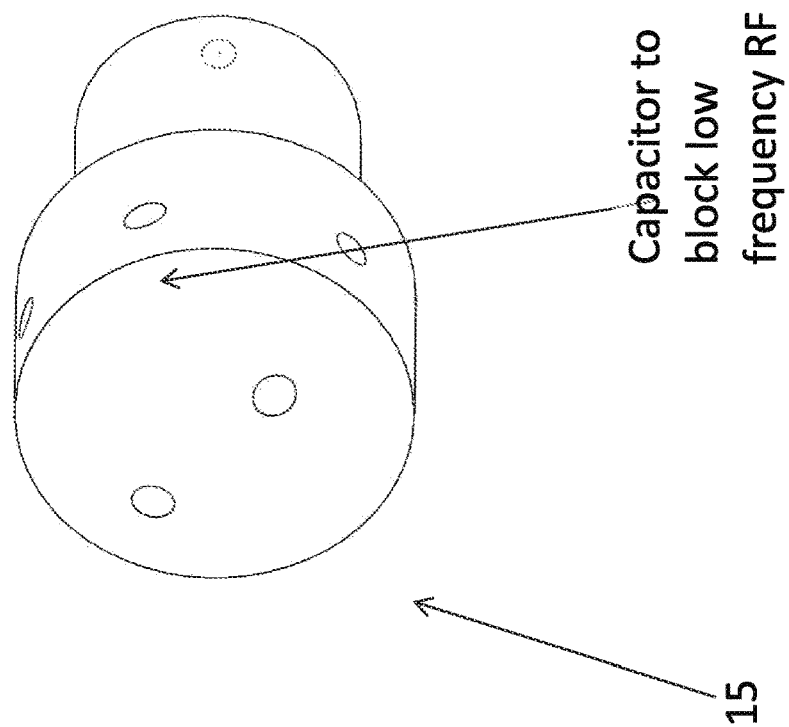
FIG. 33A is a schematic view of an antenna electrode in one embodiment of the invention.

FIG. 33 depicts an embodiment of the invention wherein the antenna electrode is a solenoid coil antenna with a spiral-helix combination. The core of the coaxial cable is connected to the solenoid spiral-helix coil at the distal hemispherical surface (at the center). The positive of the antenna is then coiled in a spiral on the distal hemispherical surface of the electrode and then continues as a helix along the sides of the electrode-antenna and connects to the ground plane via a capacitor less than 200 pF to block the ablation RF from entering the shield. This capacitor can be placed on the ground plane at other locations as well. This antenna electrode exhibits different resonant characteristics in response to the RF progression. On onset of ablation, the return loss at the resonant frequency gradually increases and flattens to zero as the lesion progresses. The capacitor blocks the ablation RF from going on the ground plane and tunes to a desired frequency.

Figure 34B:
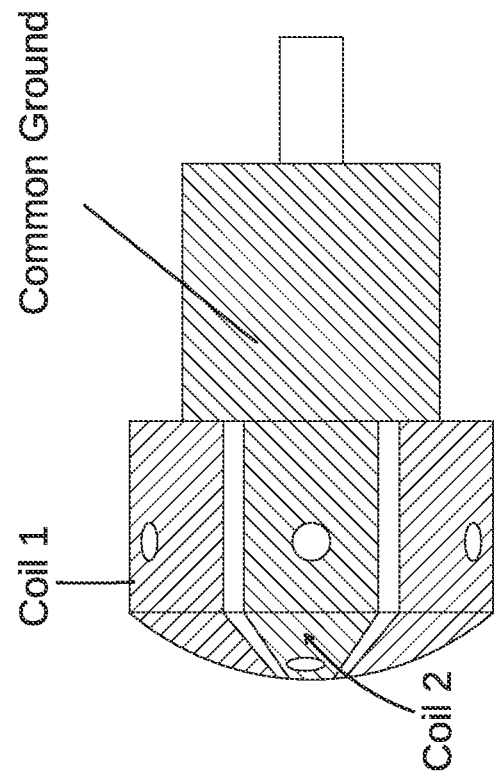
FIG. 34B is a schematic view of the antenna electrode of FIG. 34A.
Figure 34A:
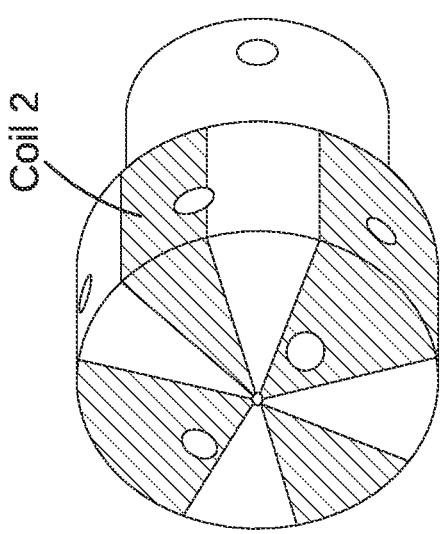
FIG. 34A is a schematic view of an antenna electrode in one embodiment of the invention.

FIG. 34 depicts an embodiment of the invention having two loop coil antennae electrodes in a quadrature arrangement. The antenna traces on the distal surface can be spiraled to provide resonance or add to the inductance. These antennae can be saddle coils with an overlapping section and other antenna configurations. With these antennae coil electrodes ablation assessment can be carried out in S11/S22 reflection mode and S21/S12 transmission mode simultaneously. Other coil configurations with similar arrangements can be envisioned, e.g. with coiled traces, zig-zag traces, co-wound/coiled traces, traces in opposite directions, and the like to increase connecting field lines and coupling. Each coil may be connected by separate coaxial cables; or a triaxial cable with common ground conductor.

In the various embodiments described herein, the ablation antenna electrode of the invention having positive and ground planes incorporated on the surface of the electrode in close proximity, the base of the antenna electrode is constructed out of dielectric materials. These can be polymeric materials, e.g. polyether ether ketone (PEEK), polyimide, and the like, or ceramic materials, such as alumina, aluminum nitride, and the like, which have poor electrical conductivity (very high electrical resistivity) and low dielectric constant (dielectric constant <20), to impart electric and magnetic field penetration in the medium surrounding the antennae. During the ablation procedure, as tissue in contact with the electrode heats, this thermal energy is conducted to the electrode as well, causing the electrode to heat. Electrode temperatures over 43° C. can cause blood coagulation on the surface of the electrode causing high impedance to RF current, preventing tissue ablation. To avoid blood coagulation on the electrode, the electrode needs to be cooled during RF ablation which is achieved by closed loop saline irrigation or open flush saline irrigation. Open flush saline irrigation is preferred due to its relatively better temperature control because of the constant saline flow, which also maintains the tissue surrounding the electrode cool, thus potentially increasing lesion depth.

Figure 35:
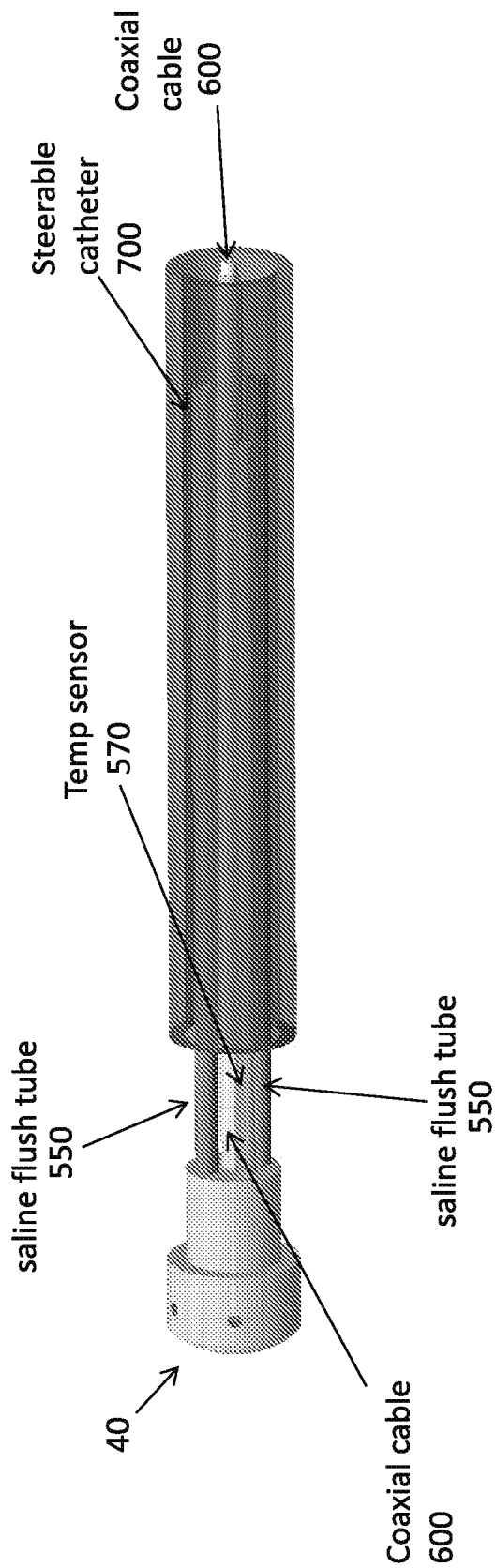
FIG. 35 is a schematic view of an ablation system in one embodiment of the invention.

In various embodiments, the ablation electrode base component is fabricated out of ceramics or polymers, or composite construction involving metal and dielectric layers with lumens for saline flush. The antenna structures are then build on this dielectric base structure. The base part comprises a cylindrical electrode base structure with a hemispherical distal surface to provide smooth contact with the tissue to be ablated. As shown in FIG. 35, saline flush lumens are fabricated to provide open saline irrigation. The saline flow is induced by a pump placed externally (typically a closed loop with the RF ablation generator so that the pump turns on when RF is applied) and delivered to the electrode via saline flush input ports. A thru lumen in the center provides access to connect the coaxial cable to the positive of the antenna. The ground plane of the antenna extends thought out the outer surface of the base component where the coaxial cable is connected. The distal surface and the side are typically in contact with the electrode to deliver ablation RF into the tissue.

The antenna electrode is fabricated in multiple steps/stages; initially a base structure out of a dielectric is machined or fabricated. The saline flush lumens, lumen to connect the positive of the antenna and the ground plane to the coaxial cable provided. Ports and lumens to house the thermocouple, positive plane nodes, and the like will be incorporated in the base structure. The ground plane and the positive plane components are then created on the substrate of conductive biocompatible metals, e.g. gold, SS316, and the like, by various means.

In one method the conductive elements of the antenna are sputtered, coated. In another method they are fabricated, machined, cast, or electrodeposited and then assembled on the ceramic/polymeric base. Open saline flush irrigation are utilized to cool the electrode and adjacent tissue during ablation. Since saline is a conductive solution (due to Na+ and Cl− ions) flowing saline solution can act as a long conducting wire and induce noise in high frequency measurement. To overcome this, the inner surfaces of the saline flush lumens have a dielectric coating and the exit ports on the surface of the electrode have a dielectric rim around them. This prevents direct saline contact with the conductive surfaces when held against the tissue.

With reference to FIG. 35, the antenna electrodes are then assembled in a steerable catheter body 700 which includes a braided tubing with varying stiffness, and a pull wire anchored in the distal section and connected to the actuation mechanism in the handle section at the proximal end to enable deflect and steer the catheter in desired orientation. A fiberoptic temperature sensor 570 or a thermocouple is embedded in the electrode and bonded with thermally conductive but dielectric adhesives. Similarly the tubing to deliver saline flush 550 to the electrode are connected/bonded to the proximal end of the electrode. The core of the coaxial cable 600 is connected to the positive of the antenna via a hypotubing subassembly which runs in the electrode central lumen and the shield is connected to the ground plane and may be crimped to the ground plane structure. The entire electrode, thermocouple, potentially contact force sensing structures are incorporated in the steerable catheter then connected to a connector comprising pins for thermocouple and other sensing electrodes and a coaxial connector for the ablation electrode. The system is ready for use after appropriate sterilization processes.

Figure 36:
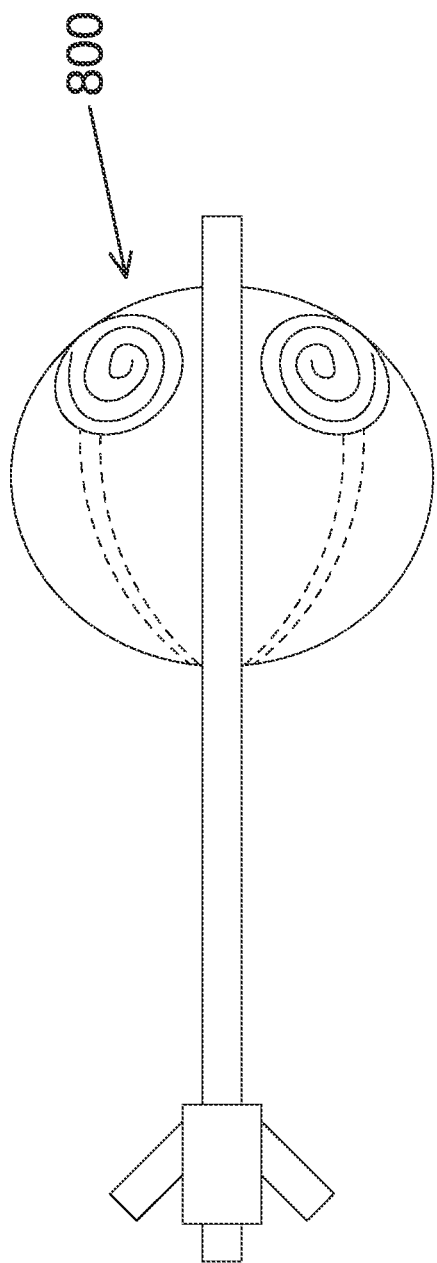
FIG. 36 is a schematic view of an ablation system having a distally disposed balloon in one embodiment of the invention.

In another embodiment as shown in FIG. 36, the spiral antenna electrode may be deposited on a balloon 800 of a balloon catheter. The circuit may be deposited directly on the balloon by sputtering or chemical vapor deposition methods; or fabricated and bonded to balloons. During clinical use the balloon may be advanced to the location of therapy, dilated with a fluid medium, e.g. oil, fat, gas, to open the balloon and to position the antenna electrode structure against the tissue to be ablated.

Figure 37:
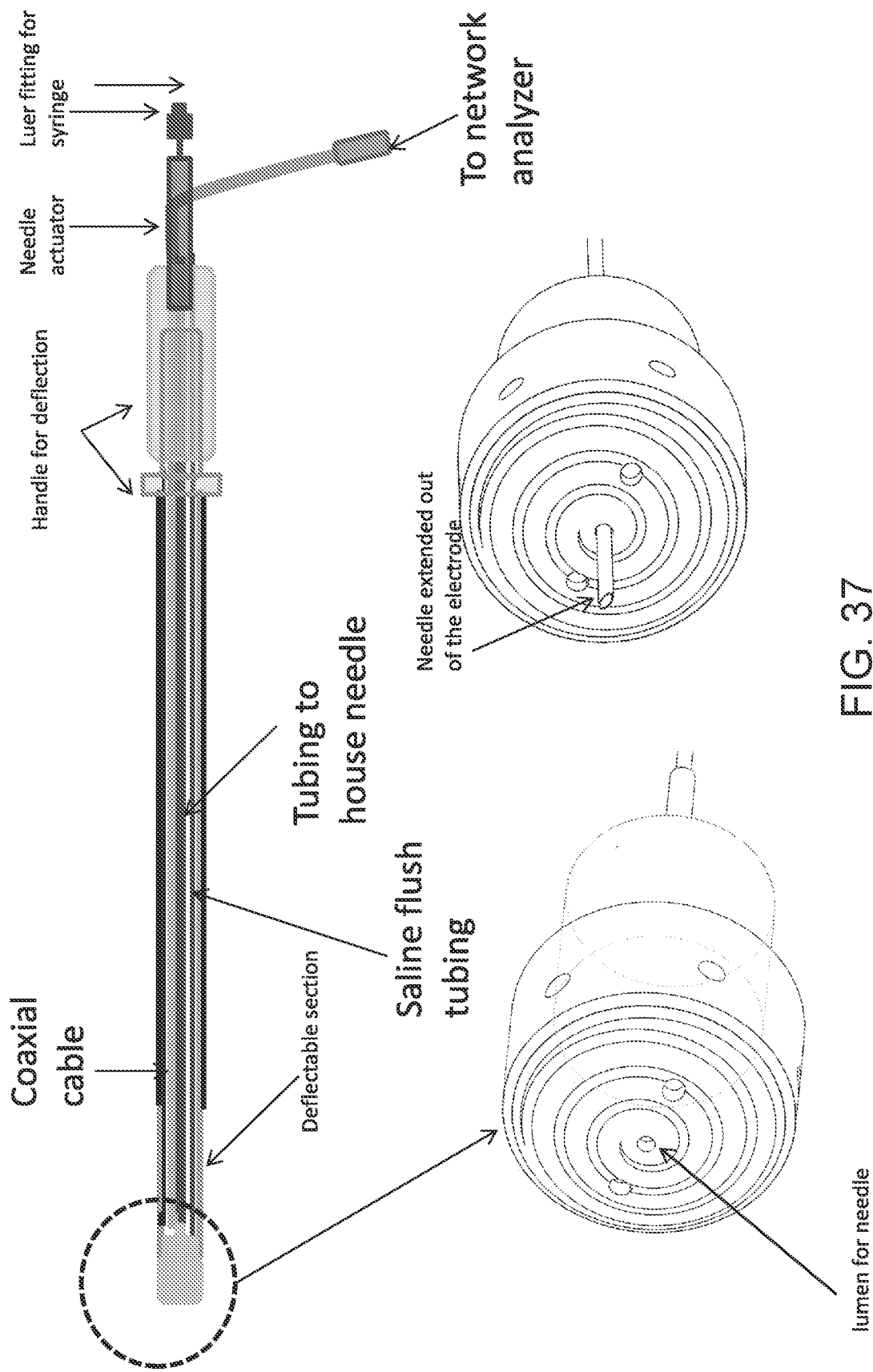
FIG. 37 is an illustration depicting an ablation system in one embodiment of the invention.

In another embodiment as shown in FIG. 37, intramyocardial/transendocardial injection catheters are used to deliver therapeutics to the cardiac tissue, e.g. warm saline for ablation, cell therapies, ablative agents, simultaneously injecting warm saline and ablation RF for creating deeper ablation lesions, and the like. The antenna electrodes can be modified by incorporating a central lumen to house the injection needle. The needle may or may not be electrically a part of the antenna electrode. It may be inductively or capacitively coupled to the antenna electrode.

As shown in FIG. 37, the catheter includes a proximal section made of stiffer braided tubing for imparting longitudinal stiffness, and a softer distal section. A pull wire runs along the length of the catheter, to enable deflect the distal section. The distal end of the pull wire is anchored towards the distal end of the distal section of the catheter. At the proximal end, the pull wire is fixed to the actuator in the handle section. The actuation mechanism moves the catheter body with respect to the pull wire deflecting the softer distal section of the catheter.

The antenna electrode design for use with an intramyocardial injection catheter is shown in FIG. 37 also. A central needle lumen in the electrode houses the needle, at the proximal end of the electrode, the central lumen is connected to a polymeric nonconductive tubing which runs along the length of the catheter and houses the needle. The needle is a composite metal-polymer tubing, with the distal 0.5-2 cm of the needle being metallic and the remaining length being a non-conductive material, e.g., polymeric. This is so that, the needle and the tubing are not a part of the antenna and do not influence return loss and phase angle measurements. The inner surface of the needle may be coated with a polymeric layer to prevent direct saline contact and prevent electrical conductivity of the saline from affecting antenna properties. The needle tip position with respect to the distal tip of the catheter can be manipulated by moving the needle at the proximal end of the catheter.

During an intramyocardial injection procedure, the catheter will be advanced into the cardiac chambers via suitable vascular access using imaging guidance. The distal tip of the catheter is placed opposed to the tissue so that the distal surface of the antenna electrode is in contact with the myocardial wall. This will be confirmed by monitoring the return loss, phase angle and resonant frequency of the antenna electrode. After the catheter tip is positioned at the location against the tissue, as confirmed by the return loss, phase angle resonant frequency, the needle is advanced out of the catheter and catheter-wall contact is ensured. When needle placement in the tissue and depth of needle in the tissue is confirmed, a contrast test injection may be delivered. The therapy/injectate is then delivered into the myocardium, and depending on the electrical properties of the injectate, the injection in the wall can be confirmed by changes in return loss, phase angle profiles of the antenna electrode. The intramyocardial injection catheter with antenna electrode may be used to simultaneously perform RF ablation and inject saline or other injectate at the same time using monitoring techniques described earlier.

The antenna electrodes implemented in cardiac RF ablation catheters and intramyocardial injection catheters as disclosed herein, can be modified for use in MRI environment to enable MRI guided procedures with design, material and layout changes. The antenna electrode will be configured as a receive-only or transmit-receive coil by matching tuning of the antenna electrode to the MRI's Larmor frequency.

Since MRI involves obtaining signal from the hydrogen proton in water molecules, interventional devices are not conspicuous in MRI. Transmit-receive or receive only antennae may be incorporated in the devices to render them conspicuous in MRI. For use in MRI, all the antennae will be tuned to the Larmor frequency of MRI, e.g. 64 MHz for 1.5 Tesla field strength, 128 MHz for 3 Tesla field strength. This enables the antennae to receive or transmit-receive NMR signal generated by the hydrogen proton during a scan. These signals picked up by the antennae are transferred to the scanners receiver amplifiers via an interface circuitry, which includes a matching tuning and decoupling circuitry. The MRI scanner's signal processing system displays these signals into images which are then seen on the scanner consoles.

The static magnetic field and RF fields generated during MRI imaging process pose significant safety hazards and interventional devices need to be designed to make them safe for use in MRI. To make the devices safe for use in MRI's static magnetic field environment, the catheters and its components are fabricated out of non-ferromagnetic/magnetic materials. This eliminates the undue/undesired mechanical forces being exerted on the catheters due to the static magnetic field, which could pose hazards to the patients and the operators.

During MR imaging, in order to obtain an image, the subject/patient is subjected to intense RF fields at Larmor frequencies, e.g. 64 MHz for 1.5 Tesla and 128 MHz for 3 Tesla. This applied RF induces local electric fields in the patient's body. An interventional device having a long linear metallic/conductive component, when placed in this electric field couples to the E-fields, voltage is induced in the device, which in turn drives a current which is deposited in the tissue in contact with the device, typically at the ends of the device, causing irreversible thermal injury. To render interventional devices safe in MRI the long linear components of the catheters/devices need to be replaced with nonconductive polymeric or ceramic components. If long metallic components are required, they need to be designed in a way to impart high impedance at MRI's Larmor frequencies.

For the RF ablation catheters and intramyocardial injection catheters of the invention, the long linear components which will pose MRI safety risks are the pull wire, coaxial cables, wires which connect to the ablation antenna electrode, sensing electrodes and the braiding in the catheter body. The coaxial cables may be arranged with intermittent chokes or windings such that the impedance on the shield of the wound coaxial cables exceeds 50 ohms/cm at Larmor frequencies when measured by a common mode measurement. The diameter, pitch and turns of the coaxial cable chokes can be adjusted to obtain this impedance. In embodiments, one or more coaxial cable chokes will be incorporated along the length of the catheter; typically the length of each choke will be shorter than 10 cm for 1.5 Tesla and 5 cm for 3 Tesla field strengths to minimize coupling to local E-fields. The length of the chokes, diameter and pitch should be adjusted so as to get over 300 ohms impedance over the entire length of the choke, but keeping the overall length shorter than 9 cm for 1.5 T and 4.5 cm for 3 T field strengths. The overall length of the coaxial cables will typically be an odd multiple of $\lambda/4$ (quarter wavelength) for ease of decoupling by a pin diode.

Figure 38:
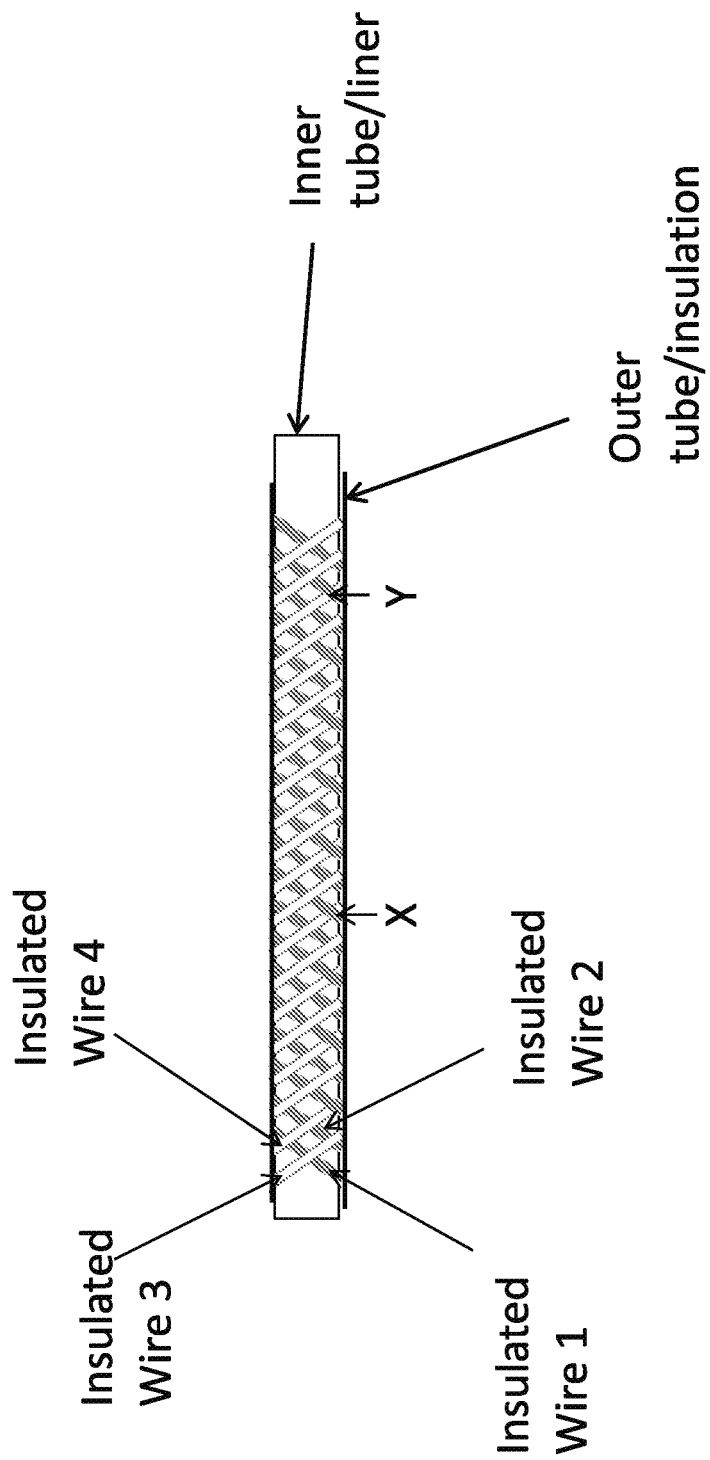
FIG. 38 is a schematic view of a portion of an ablation system in one embodiment of the invention which includes a metal braided catheter.

FIG. 38 illustrates a braided section of catheter tubing in one embodiment of the invention. The metal braiding used in catheter tubing includes two or more flat or round wires braided in sets of two such that wires crisscross and overlap one over the other, creating a thick weave and impart longitudinal column strength, rigidity and longitudinal flexibility at the same time. Such a braided wire structure acts as a long linear conductor, since all the wires are electrically connecting each other on every wind, posing significant RF safety risks when used in MRI. To make the braided section of the catheter safe for use in MRI, a braiding with 2 or more wires where at least half the number of wires have an insulating/dielectric coating on them to prevent electrical contact with each other, are wound/braided with pitch and diameter such that each individual wire in a braided section will have an impedance exceeding 25 ohms/cm at the Larmor frequency when measured in the common mode. Further, in a length shorter than quarter wavelength for a bare wire, i.e. shorter than 10 cm for 1.5 T and 5 cm for 3 T, an individual braided wire will have an impedance peak exceeding 300 ohms at Larmor frequencies, i.e. 64 MHz for 1.5 T and 128 MHz for 3 T. No wires in the braid are in direct electrical contact with each other and the overall assembly is insulated in a dielectric coating. The insulating coating could be varnish, lacquer, polyimide and other polymers. Another method, would be to create a dissipative shield, where a section of the braiding may be completely uninsulated, so that it is in direct contact with tissue. This dissipates the induced currents over a large surface area causing minimal tissue thermal injury.

Figure 39:
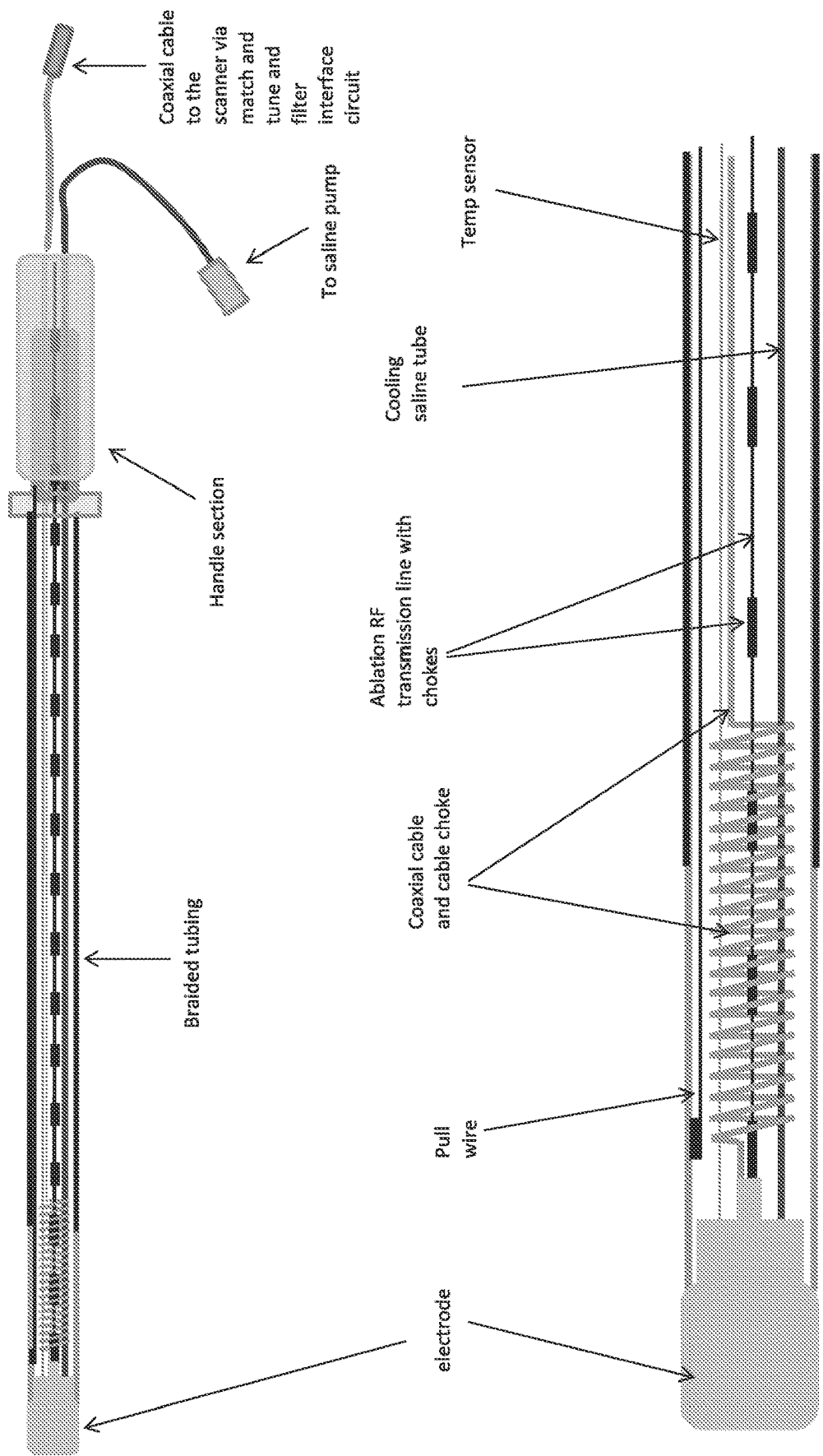
FIG. 39 is an illustration depicting an ablation system in one embodiment of the invention.

FIG. 39 illustrates an MRI active cardiac ablation catheter of the invention. The catheter includes an antenna electrode, connected to a coaxial cable with one or more intermittent chokes to transmit and/or receive NMR signals. The catheter includes a wire with multiple RF suppression chokes for transmitting ablation RF or a polymeric tube to house the injection needle. The assembly is housed in a metallic braided tubing or a polymeric tubing; where each braid wire is individually insulated and the braid wires arrange in a pitch and diameter such that each wire has an impedance over 50 ohms at NMR frequencies. Alternately an entirely polymeric steerable catheter may be implemented as well. A non-polymeric pull wire enables deflect the distal section and steer and torque. The match and tune circuit interfaces the output of the antenna to scanner receivers frequencies and can be incorporated in the distal section close to the antenna electrode or in the proximal handle section of the catheter. Since, it is known that tissue under ablation changes electrical properties during the ablation processes; different matching-tuning strategies can be implemented so that the electrode MRI signal changes with tissue contact, RF delivery to tissue and lesion progression. Auto tuning approaches may be implemented; which may better enable monitor and assess lesion formation. Monitoring reflection electrical characteristics of the antenna-electrode by a network analyzer during RF ablation can be done by filtering out all frequencies little over the Larmor frequency.

Figure 40:
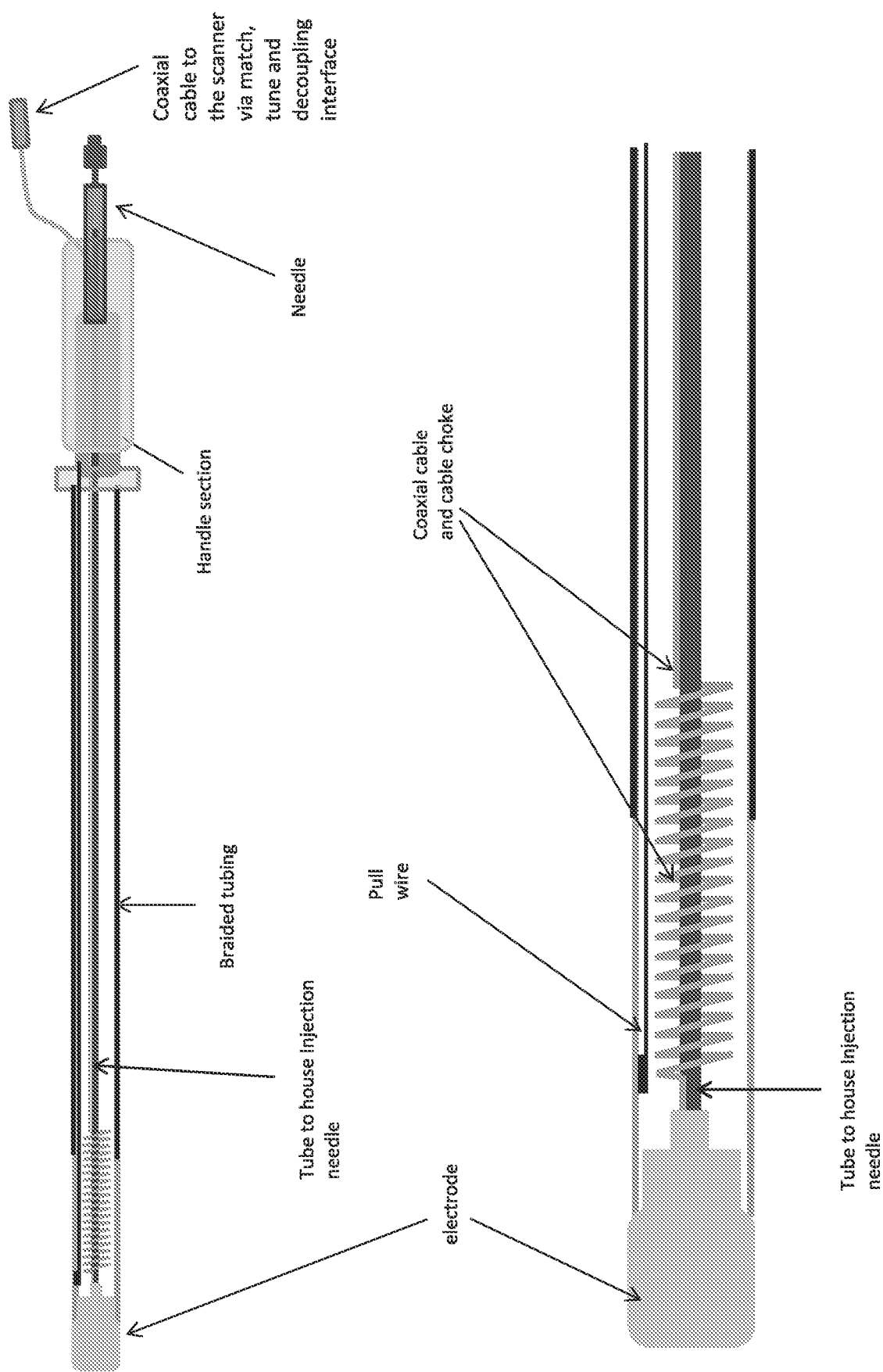
FIG. 40 is an illustration depicting an ablation system in one embodiment of the invention.

FIG. 40 illustrates an MRI active injection catheter of the invention. The antenna electrode 10 is connected to a coaxial cable with one or more intermittent chokes, where each choke has an average impedance of over 50 ohms/cm when measured on the shield in the common mode at MRI frequencies. The center of the electrode is connected to a polymeric tubing which houses the injection needle assembly. The injection needle assembly may be permanently incorporated in the catheter or may be removable to function as a guidewire lumen to facilitate advancing the catheter in the left ventricle. The needle is a composite needle, where the distal 0.5 to 2 cm of the needle is made of an MRI compatible metal and rest of the length is made of a polymeric tube; this is to prevent the needle component from acting as an MRI antenna and confounding the signal. The conductive end of the needle may be in direct electrical contact with the antenna electrode so as to visualize the needle in the MRI image as it advances out of the catheter and retracts back in the catheter.

During use in MRI, the intramyocardial injection catheter, the ablation catheter and other needle-electrode catheters may be used in combination with other external coils to receive NMR signals. Since these catheter coils will be connected to separate receiver channels, the signals from these devices may be color coded to make the devices conspicuous in MRI and trackable as well.

Figure 41:
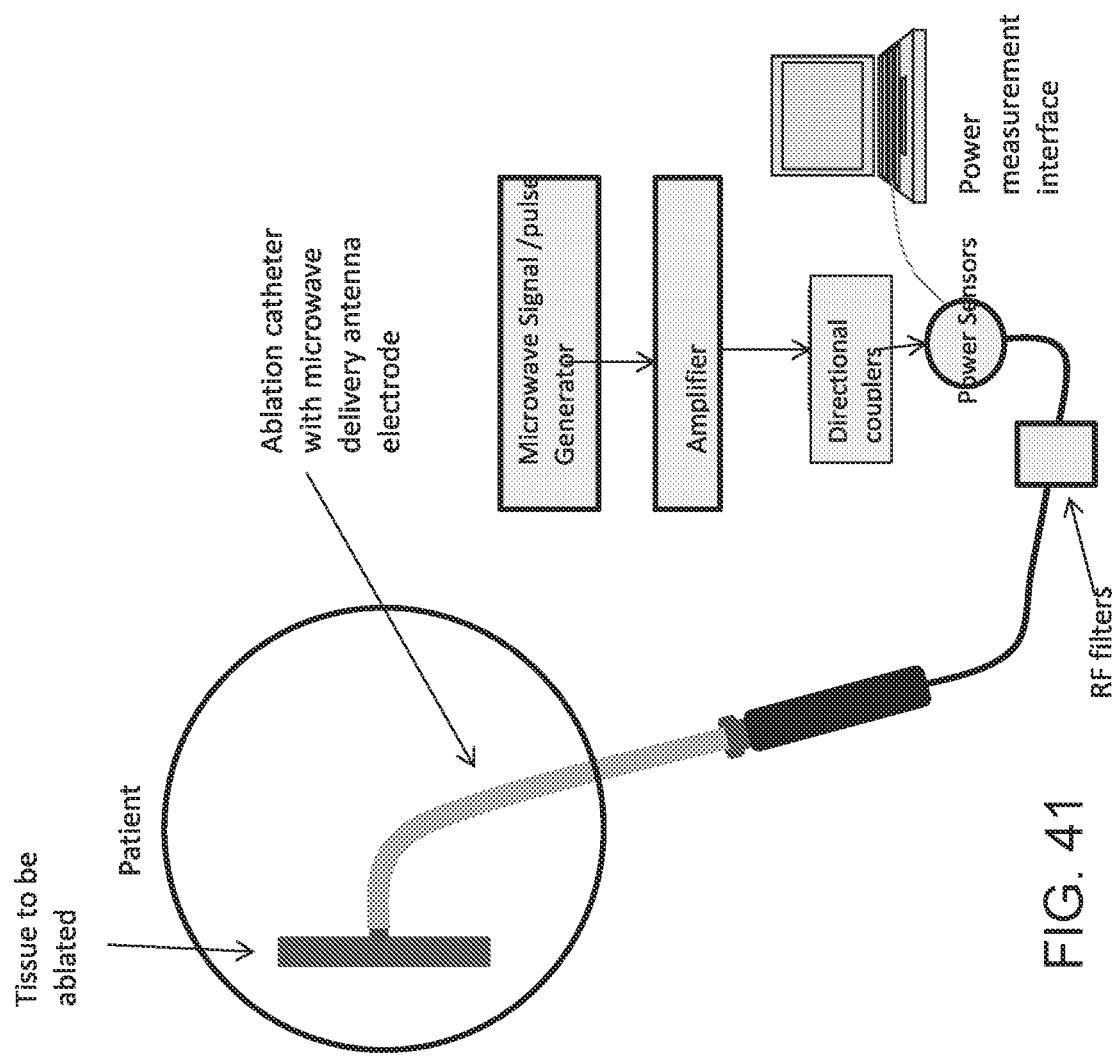
FIG. 41 is an illustration depicting an ablation system in one embodiment of the invention.

FIG. 41 is a schematic of a layout using the antenna electrode catheters for microwave ablation. The ablation catheter with the antenna electrode is connected to a signal generator, which generates an electromagnetic signal in a narrow band or a broad frequency range which may remain constant during the ablation procedure or change as the ablation progresses. The output of the signal generator is amplified by the amplifier and the directional coupler measures the amplitude of transmitted and reflected frequencies to and back from the antenna electrode. A controller may be implemented to adjust the ablation signal frequency as the ablation progresses so as to minimize reflected energy and deposit maximum energy in the tissue to create deeper necrotic lesions. Since microwave energy ablation is not based on ohmic heating, as like low frequency RFA, adjusting the input frequency to match the antenna electrode's resonant frequency, will enable deposit more energy in the tissue. This will be safer, since ablation can be carried out at lower power levels.

Figure 42:
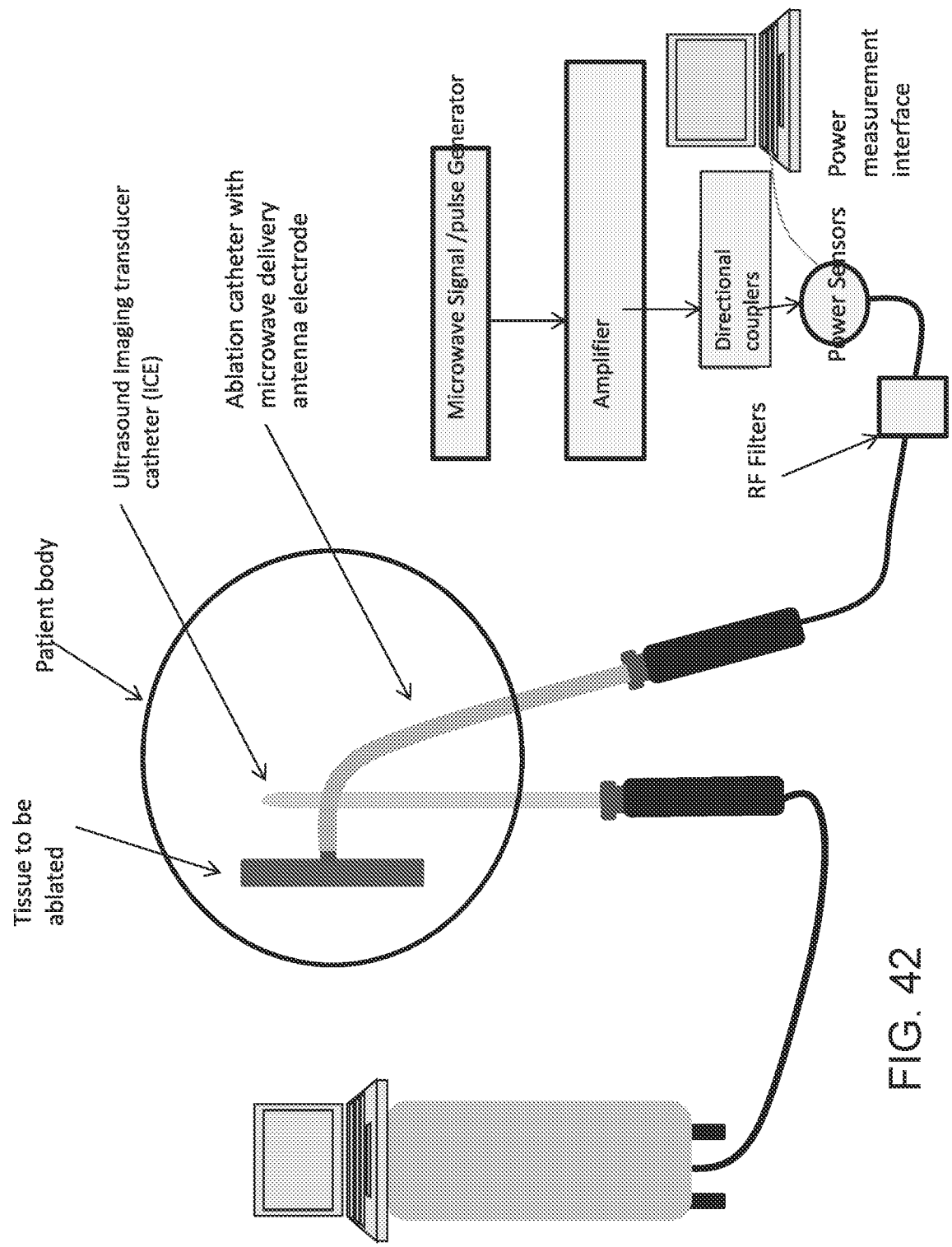
FIG. 42 is an illustration depicting an ablation system in one embodiment of the invention.

FIG. 42 is a schematic of a thermoacoustic imaging system, where microwave energy pulse of a short duration may be delivered alongside low frequency RF current. A high frequency microwave pulse over 900 MHz frequency will generate acoustic noise in the tissue. This acoustic noise may be intercepted by intracardiac or external ultrasound transducer devices, e.g. intracardiac ultrasound imaging and sensing catheter, transesophageal catheter, and the like. Signal processing algorithms will analyze the thermoacoustic signals to distinguish between ablated and non-ablated tissue.

Although the invention has been described with reference to the above example, it will be understood that modifications and variations are encompassed within the spirit and scope of the invention. Accordingly, the invention is limited only by the following claims.

What is claimed is:

1. A system for assessing the state of a biological tissue comprising:

an ablation signal generator configured to generate an ablation signal having a frequency of 1 MHz or less;
at least one antenna configured to:
i) transmit an assessment signal having a frequency of at least 1 MHz to the tissue;
ii) receive the assessment signal having a frequency of at least 1 MHz from the tissue; and
iii) transmit an ablation signal to the tissue produced by the ablation signal generator, the ablation signal having a frequency of 1 MHz or less;
a network analyzer and signal processing device; and
a high frequency output configured to output the received assessment signal to the network analyzer and signal processing device.

2. The system of claim 1, further comprising a high frequency input configured to receive the received signal from the tissue via the at least one antenna.

3. The system of claim 1, wherein the ablation signal has a higher wattage than the transmitted or received assessment signal.

4. The system of claim 1, further comprising a low frequency input configured to receive the ablation signal from the ablation generator.

5. The system of claim 1, wherein the at least one antenna is further configured to receive a low frequency signal from the tissue.

6. The system of claim 5, further comprising a low frequency output configured to output the received low frequency signal to the network analyzer and signal processing device.

7. The system of claim 1, wherein the at least one antenna comprises a coaxial antenna comprising at least two electrodes separated by a dielectric.

8. The system of claim 1, wherein the at least one antenna comprises a spiral antenna comprising:
an inner electrode wound as a spiral;
an outer electrode surrounding the outside of the spiral; and
at least one dielectric separating turns of the spiral and separating the inner electrode and the outer electrode.

9. A method for determining a property of a tissue, the method comprising:
transmitting, with at least one antenna of a catheter, a transmitted assessment signal having a frequency of at least 1 MHz to tissue;
receiving, with the at least one antenna, a received assessment signal having a frequency of at least 1 MHz from the tissue;
detecting, with a processor of a network analyzer and signal processing device, an electrical property of the received assessment signal;
determining, with the processor, a property of the tissue based on the detected electrical property of the received assessment signal; and
transmitting an ablation signal to the tissue with the at least one antenna of the catheter, the ablation signal being produced by an ablation signal generator and having a frequency of 1 MHz or less.

10. The method of claim 9, further comprising generating, with a signal generator of the network analyzer and signal processing device, the transmitted assessment signal.

11. The method of claim 9, wherein the ablation signal has a higher wattage than the assessment signals.

12. The method of claim 9, further comprising:
receiving, with the at least one antenna, a low frequency signal from the tissue; and
analyzing, with the processor, the low frequency signal to determine an endocardial potential of the tissue.

13. The method of claim 9, wherein determining the property of the tissue comprises performing a reflection S11 measurement on the received assessment signal, performing a transmission S21 or S12 measurement on the received electrical signal, or a combination thereof.

14. The method of claim 9, wherein:
the detected electrical property of the received assessment signal is indicative of a change in an electrical property of an antenna of the catheter; and
determining the property of the tissue comprises inferring a change in a property of the tissue corresponding to the change in the electrical property of the antenna.

15. The method of claim 9, wherein the property of the tissue comprises an electrode-tissue contact quality, a rate of ablation, a degree of ablation, a temperature, a progression of lesion formation, an extent of lesion formation, a thermoacoustic image, or a combination thereof.

16. An ablation device comprising:
an ablation signal generator configured to generate an ablation signal having a frequency of 1 MHz or less;
at least one antenna on the ablation device configured to:
i) transmit an assessment signal having a frequency of at least 1 MHz to the tissue;
ii) receive the assessment signal having a frequency of at least 1 MHz from the tissue; and
iii) transmit an ablation signal to the tissue produced by the ablation signal generator, the ablation signal having a frequency of 1 MHz or less;
a network analyzer and signal processing device; and
a high frequency output configured to output the received assessment signal to the network analyzer and signal processing device.

17. The device of claim 16, further comprising a high frequency input configured to receive the received assessment signal from the tissue via the at least one antenna of the catheter.

18. The device of claim 16, wherein the ablation signal has a higher wattage than the transmitted or received assessment signal.

* * * * *